United States Patent
Manoharan et al.

(10) Patent No.: US 12,023,383 B2
(45) Date of Patent: *Jul. 2, 2024

(54) LIPID COMPOSITIONS

(71) Applicant: ARBUTUS BIOPHARMA CORPORATION, Warminster, PA (US)

(72) Inventors: Muthiah Manoharan, Cambridge, MA (US); Kallanthottathil G. Rajeev, Cambridge, MA (US); Muthusamy Jayaraman, Cambridge, MA (US); David Butler, Medford, MA (US); Michael E. Jung, Cambridge, MA (US)

(73) Assignee: ARBUTUS BIOPHARMA CORPORATION, Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,654

(22) Filed: Feb. 16, 2023

(65) Prior Publication Data

US 2024/0066129 A1    Feb. 29, 2024

Related U.S. Application Data

(63) Continuation of application No. 17/200,230, filed on Mar. 12, 2021, now abandoned, which is a continuation of application No. 16/593,661, filed on Oct. 4, 2019, now Pat. No. 10,953,095, which is a continuation of application No. 15/594,244, filed on May 12, 2017, now Pat. No. 10,456,473, which is a continuation of application No. 14/508,805, filed on Oct. 7, 2014, now Pat. No. 9,694,077, which is a continuation of application No. 13/318,600, filed as application No. PCT/US2010/033777 on May 5, 2010, now Pat. No. 8,883,202.

(60) Provisional application No. 61/299,291, filed on Jan. 28, 2010, provisional application No. 61/175,770, filed on May 5, 2009.

(51) Int. Cl.
| | |
|---|---|
| *A61K 47/22* | (2006.01) |
| *A61K 9/127* | (2006.01) |
| *C07D 295/13* | (2006.01) |
| *C12N 15/113* | (2010.01) |

(52) U.S. Cl.
CPC ........... *A61K 47/22* (2013.01); *A61K 9/1272* (2013.01); *C07D 295/13* (2013.01); *C12N 15/113* (2013.01); *C12N 15/1137* (2013.01); *C12N 2310/14* (2013.01); *Y02A 50/30* (2018.01)

(58) Field of Classification Search
CPC .... A61K 47/22; A61K 9/1272; C07D 295/13; C12N 15/113; C12N 15/1137; C12N 2310/14; Y02A 50/30
See application file for complete search history.

(56) References Cited

U.S. PATENT DOCUMENTS

| | | |
|---|---|---|
| 3,646,037 A | 2/1972 | Schindler et al. |
| 3,931,430 A | 1/1976 | Tada et al. |
| 4,743,304 A | 5/1988 | Gilmore et al. |
| 5,891,468 A | 4/1999 | Martin et al. |
| 6,022,874 A | 2/2000 | Wheeler |
| 6,291,423 B1 | 9/2001 | Bischoff et al. |
| 6,835,395 B1 | 12/2004 | Semple et al. |
| 8,883,202 B2 | 11/2014 | Manoharan et al. |
| 9,694,077 B2 | 7/2017 | Manoharan et al. |
| 10,456,473 B2 | 10/2019 | Manoharan et al. |
| 10,953,095 B2 | 3/2021 | Manoharan et al. |
| 2002/0156085 A1 | 10/2002 | Anand et al. |
| 2003/0175966 A1 | 9/2003 | Wang et al. |
| 2004/0009216 A1 | 1/2004 | Rodrigueza et al. |
| 2009/0023673 A1 | 1/2009 | Manoharan et al. |
| 2022/0040308 A1 | 2/2022 | Manoharan et al. |

FOREIGN PATENT DOCUMENTS

| | | |
|---|---|---|
| JP | 6032780 A | 2/1985 |
| JP | H01301364 A | 12/1989 |
| WO | 2000049125 A1 | 8/2000 |
| WO | 2007130073 A2 | 11/2007 |
| WO | 2008113364 A2 | 9/2008 |
| WO | 2010053572 A2 | 5/2010 |

OTHER PUBLICATIONS

Jenning, V , et al., "Vitamin A—loaded solid lipid nanoparticles for topical use: drug release properties", Journal of Controlled Release 66(2), 115-126 (2000).
Love , et al., "Lipid-like materials for low-dose, in vivo gene silencing", PNAS 107(5), 1864-1869 (2010).
Love , et al., "Lipid-llike materials for low-dose, in vivo gene silencing", PNAS 107(5), 1864-1869, Supporting information, Love et al., 10.1073/pnas.0910603106, 5 pages (2010).
Patent Cooperation Treaty, International Searching Authority, Search Report and Written Opinion for PCT/2010/033777, 11 pages, Aug. 20, 2016.

*Primary Examiner* — Snigdha Maewall

(74) *Attorney, Agent, or Firm* — Viksnins Harris Padys Malen LLP

(57) ABSTRACT

Disclosed herein are lipid compositions comprising a cationic lipid of formula (I), a neutral lipid, a sterol and a PEG or PEG-modified lipid, wherein formula (I) is (F). Also disclosed are methods of producing the cationic lipid of formula (I).

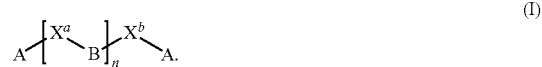

(I)

20 Claims, 18 Drawing Sheets

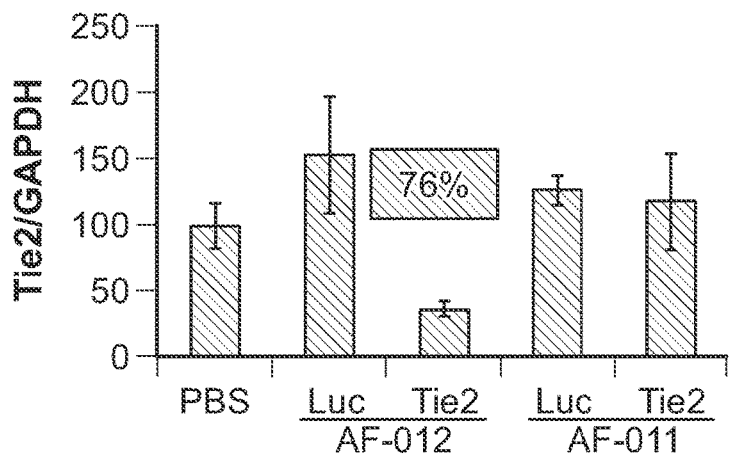
FIG. 10A. Heart
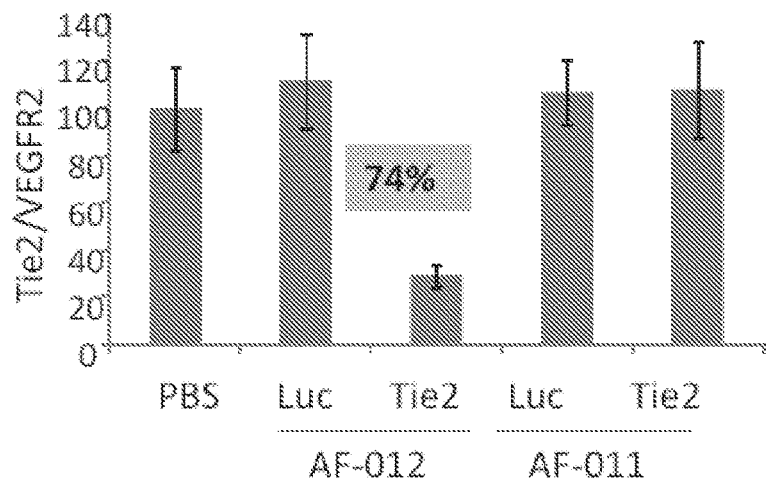
FIG. 10B
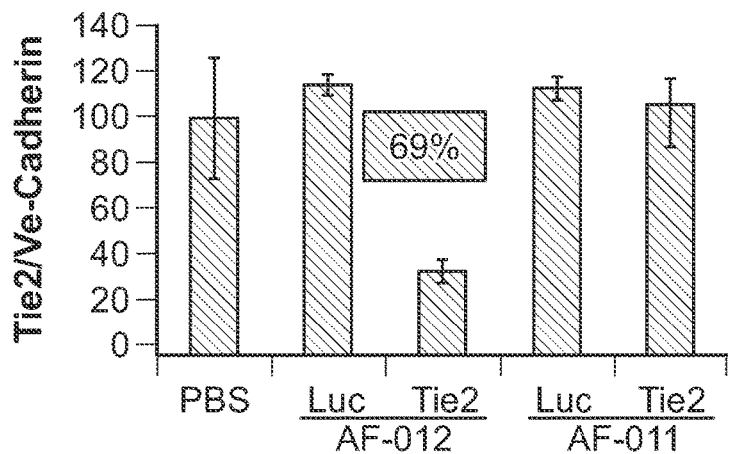
FIG. 10C

FIG. 11A. Liver
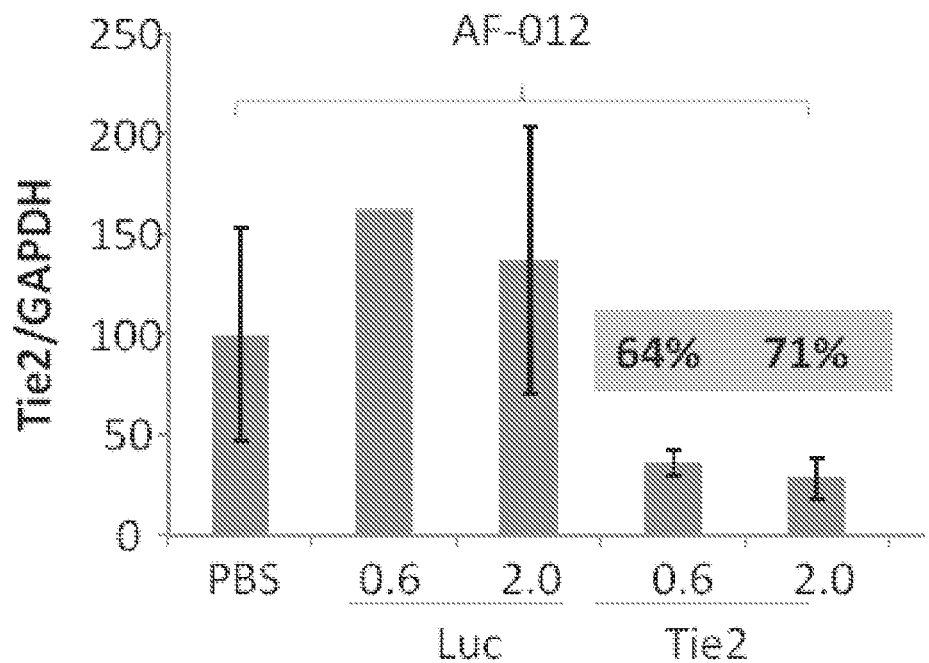
FIG. 11B
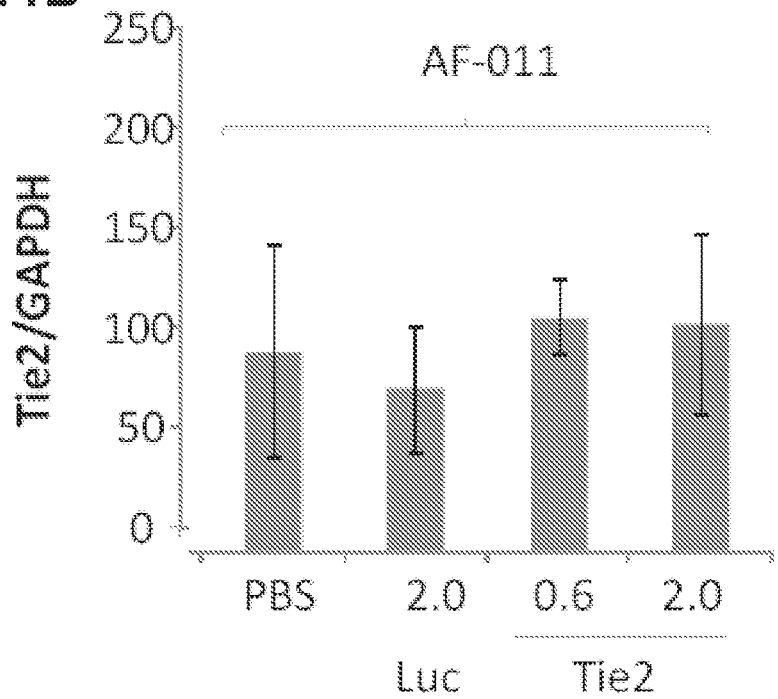

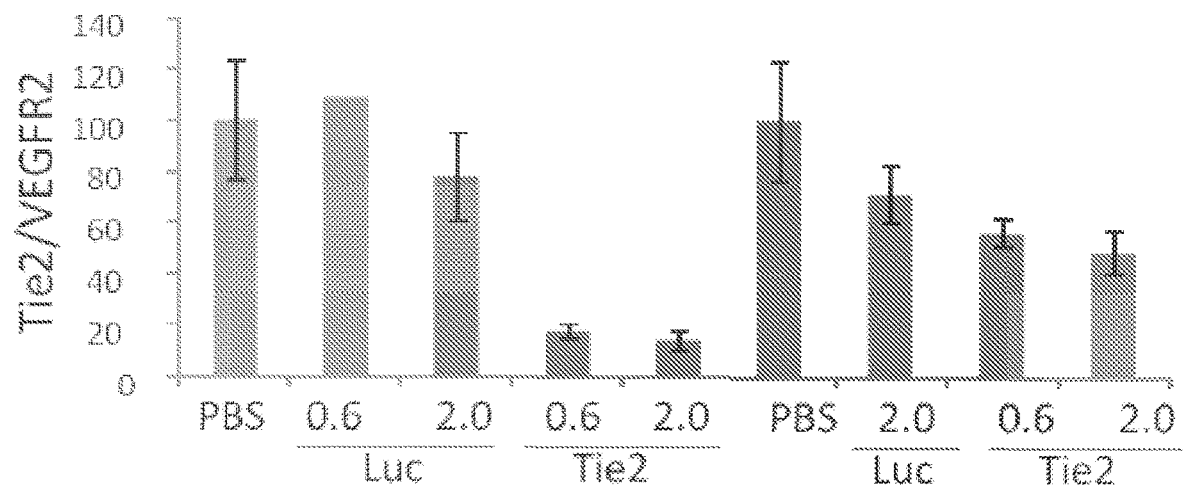
FIG. 12A. Liver
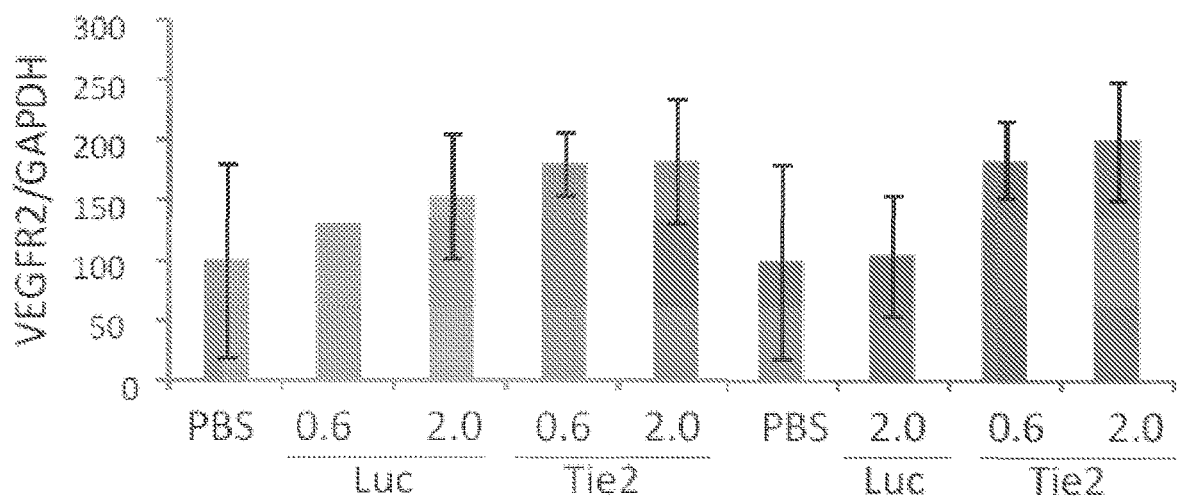
FIG. 12B. Liver

FIG. 13A. Lung
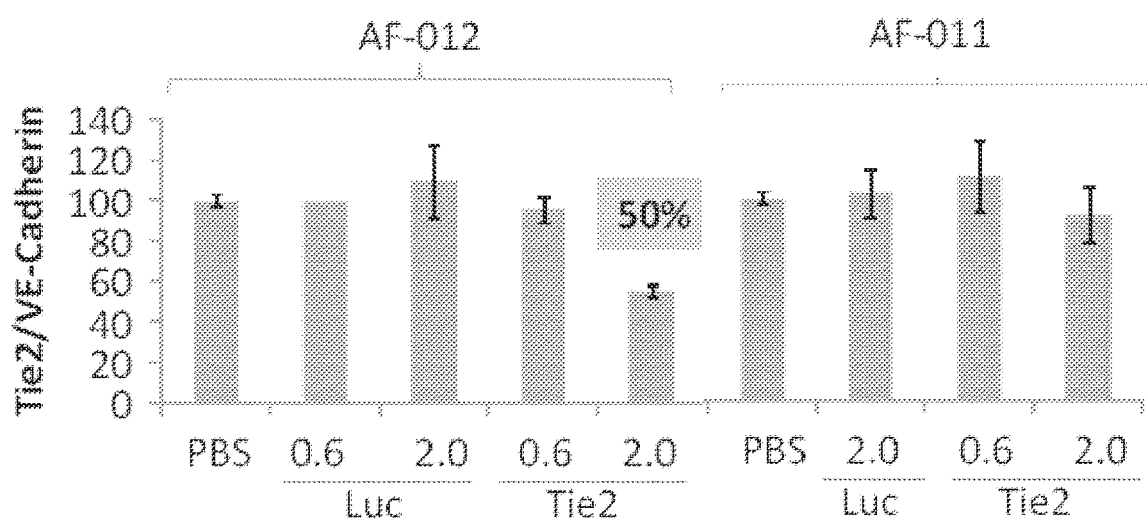
FIG. 13B
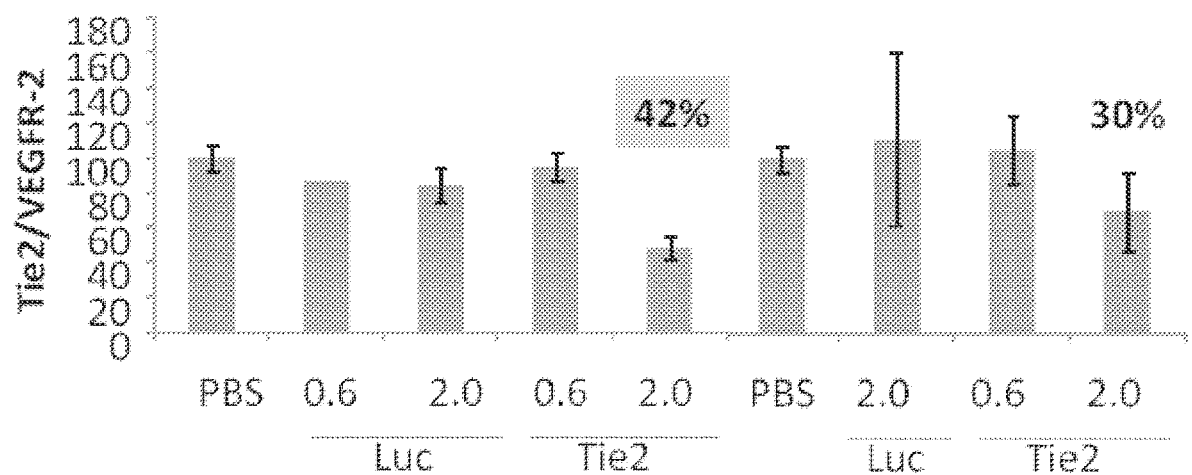

LIPID COMPOSITIONS

CROSS-REFERENCE TO RELATED APPLICATIONS

This application is a continuation application of U.S. application Ser. No. 17/200,230, filed Mar. 12, 2021, which is continuation application of U.S. application Ser. No. 16/593,661, filed Oct. 4, 2019, now U.S. Pat. No. 10,953,095, issued Mar. 23, 2021, which is a continuation application of U.S. application Ser. No. 15/594,244, filed May 12, 2017, now U.S. Pat. No. 10,456,473, issued Oct. 29, 2019, which is a continuation application of U.S. application Ser. No. 14/508,805, filed Oct. 7, 2014, now U.S. patent Ser. No. 9/694,077, issued Jul. 4, 2017, which is a continuation application of U.S. application Ser. No. 13/318,600, now U.S. Pat. No. 8,883,202, issued Nov. 11, 2014, which is a 35 U.S.C. § 371 application of International Application No. PCT/US2010/033777, filed May 5, 2010, which claims priority to U.S. Provisional Application Ser. No. 61/299,291, filed Jan. 28, 2010 and U.S. Provisional Application Ser. No. 61/175,770, filed May 5, 2009, the contents of each of which is incorporated herein by reference.

TECHNICAL FIELD

The invention relates to the field of therapeutic agent delivery using lipid particles. In particular, the invention provides cationic lipids and lipid particles comprising these lipids, which are advantageous for the in vivo delivery of nucleic acids, as well as nucleic acid-lipid particle compositions suitable for in vivo therapeutic use. Additionally, the invention provides methods of preparing these compositions, as well as methods of introducing nucleic acids into cells using these compositions, e.g., for the treatment of various disease conditions.

DESCRIPTION OF THE RELATED ART

Therapeutic nucleic acids include, e.g., small interfering RNA (siRNA), micro RNA (miRNA), antisense oligonucleotides, ribozymes, plasmids, and immune stimulating nucleic acids. These nucleic acids act via a variety of mechanisms. In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind RISC when administered systemically as the free siRNA or miRNA. These double-stranded constructs can be stabilized by incorporation of chemically modified nucleotide linkers within the molecule, for example, phosphothioate groups. However, these chemical modifications provide only limited protection from nuclease digestion and may decrease the activity of the construct. Intracellular delivery of siRNA or miRNA can be facilitated by use of carrier systems such as polymers, cationic liposomes or by chemical modification of the construct, for example by the covalent attachment of cholesterol molecules. However, improved delivery systems are required to increase the potency of siRNA and miRNA molecules and reduce or eliminate the requirement for chemical modification.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA. Advanced human clinical assessments of several antisense drugs are currently underway. Targets for these drugs include the bcl2 and apolipoprotein B genes and mRNA products.

One well known problem with the use of therapeutic nucleic acids relates to the stability of the phosphodiester internucleotide linkage and the susceptibility of this linker to nucleases. The presence of exonucleases and endonucleases in serum results in the rapid digestion of nucleic acids possessing phosphodiester linkers and, hence, therapeutic nucleic acids can have very short half-lives in the presence of serum or within cells. (Zelphati, O., et al., Antisense. Res. Dev. 3:323-338 (1993); and Thierry, A. R., et al., pp147-161 in Gene Regulation: Biology of Antisense RNA and DNA (Eds. Erickson, R P and Izant, JG; Raven Press, NY (1992)). Therapeutic nucleic acid being currently being developed do not employ the basic phosphodiester chemistry found in natural nucleic acids, because of these and other known problems.

This problem has been partially overcome by chemical modifications that reduce serum or intracellular degradation. Modifications have been tested at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130). Other changes have been attempted. However, none of these solutions have proven entirely satisfactory, and in vivo free therapeutic nucleic acids still have only limited efficacy.

In addition, as noted above relating to siRNA and miRNA, problems remain with the limited ability of therapeutic nucleic acids to cross cellular membranes (see, Vlassov, et al., Biochim. Biophys. Acta 1197:95-1082 (1994)) and in the problems associated with systemic toxicity, such as complement-mediated anaphylaxis, altered coagulatory properties, and cytopenia (Galbraith, et al., Antisense Nucl. Acid Drug Des. 4:201-206 (1994)).

In spite of recent progress, there remains a need in the art for improved lipid-therapeutic nucleic acid compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these lipid-nucleic acid particles should be well-tolerated and provide an adequate therapeutic index, such that patient treatment at an effective dose of the nucleic acid is not associated with significant toxicity and/or risk to the patient. The invention provides such compositions, methods of making the compositions, and methods of using the compositions to introduce nucleic acids into cells, including for the treatment of diseases.

SUMMARY OF INVENTION

The invention provides lipid compositions comprising a cationic lipid of formula (I), a neutral lipid, a sterol and a PEG or PEG-modified lipid, wherein formula (I) is

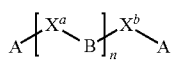

wherein
each $X^a$ and $X^b$, for each occurrence, is independently $C_{1-6}$ alkylene;
n is 0, 1, 2, 3, 4, or 5;
A for each occurrence is $NR_2$ or a cyclic moiety optionally substituted with 1-3 R;
B is NR or a cyclic moiety optionally substituted with 1-2 R;
each R is independently H, alkyl,

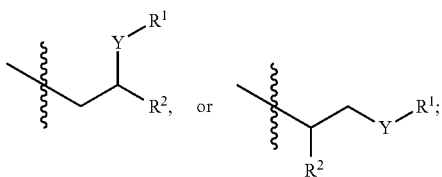

provided that at least one R is

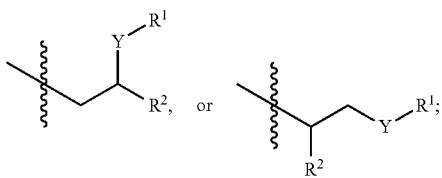

$R^1$, for each occurrence, is independently H, $R^3$,

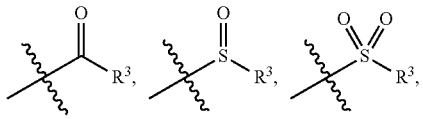

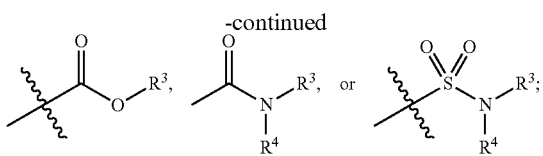

$R^2$, for each occurrence, is independently, alkyl, alkenyl, alkynyl, heteroalkyl, heteroalkenyl, or heteroalkynyl; each of which is optionally substituted with one or more substituent;

$R^3$, for each occurrence, is independently, alkyl, alkenyl, alkynyl, heteroalkyl, heteroalkenyl, or heteroalkynyl; each of which is optionally substituted with one or more substituent (e.g., a hydrophilic substituent);

Y, for each occurrence, is independently O, $NR^4$, or S;

$R^4$, for each occurrence is independently H alkyl, alkenyl, alkynyl, heteroalkyl, heteroalkenyl, or heteroalkynyl; each of which is optionally substituted with one or more substituent.

The invention further provides methods of formulation the compositions and methods of treating diseases using the lipid compositions.

In another aspect, a method of making a compound of formula (IV)

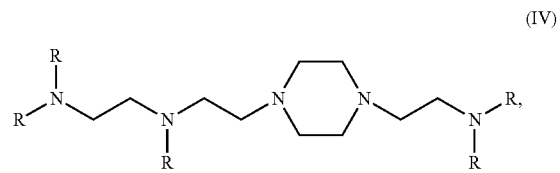

wherein each R is independently H, alkyl,

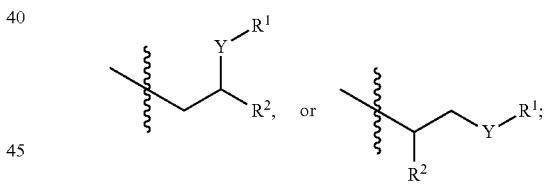

provided that at least one R is

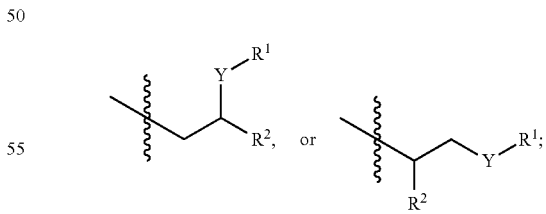

wherein $R^1$, for each occurrence, is independently H, $R^3$,

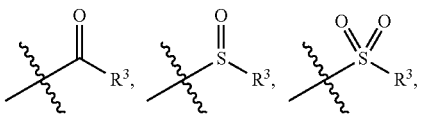

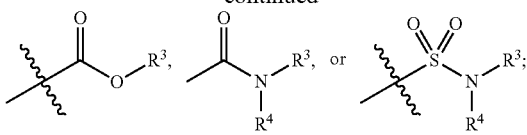

wherein $R^3$ is optionally substituted with one or more substituent;

- $R^2$, for each occurrence, is independently, alkyl, alkenyl, alkynyl, heteroalkyl, heteroalkenyl, or heteroalkynyl; each of which is optionally substituted with one or more substituent;
- $R^3$, for each occurrence, is independently, alkyl, alkenyl, alkynyl, heteroalkyl, heteroalkenyl, or heteroalkynyl; each of which is optionally substituted with one or more substituent;
- Y, for each occurrence, is independently, O, $NR^4$, or S;
- $R^4$, for each occurrence, is independently, H alkyl, alkenyl, alkynyl, heteroalkyl, heteroalkenyl, or heteroalkynyl; each of which is optionally substituted with one or more substituent;
- the method including contacting an enantiomerically enriched β-hydroxyalkyl synthetic equivalent, the β-hydroxyalkyl group being optionally substituted with one or more substituent, with a compound of formula (VIII)

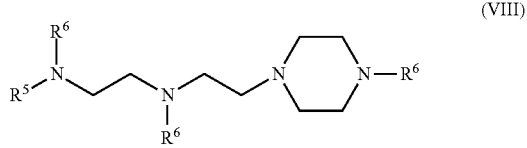

(VIII)

wherein $R^5$, for each occurrence, is independently, H, alkyl, or an amine protecting group, wherein alkyl is optionally substituted with one or more substituent; and $R^6$, for each occurrence, is independently, H, —$(CH_2)_2N(R^5)_2$, or an amine protecting group.

The β-hydroxyalkyl synthetic equivalent can be a precursor to R. In other words, functional groups provided by the β-hydroxyalkyl synthetic equivalent can undergo further reactions to afford the final R group(s) in the compound of formula (IV).

The compound of formula (VIII) can be

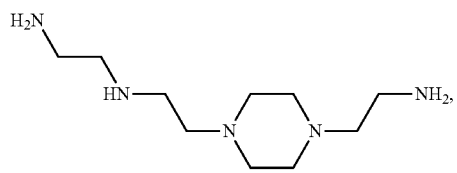

1

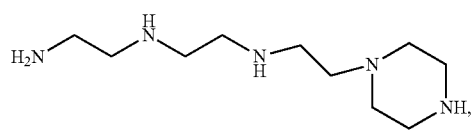

2

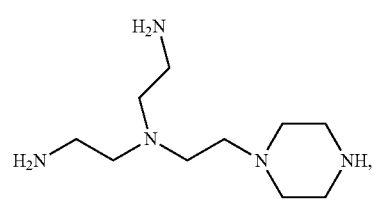

8 or a mixture thereof.

The enantiomerically enriched β-hydroxyalkyl synthetic equivalent can include an enantiomerically enriched 1,2-epoxyalkane, such as, for example, (R)-1,2-epoxydodecane. The enantiomerically enriched β-hydroxyalkyl synthetic equivalent can include a protected α-hydroxyaldehyde, such as, for example, 2-(O-Pg)-dodecanal, wherein O-Pg represents a protected hydroxyl group.

The method can further include contacting a primary alcohol trapping reagent with a product of a reaction between the enantiomerically enriched β-hydroxyalkyl synthetic equivalent and the compound of formula (VIII).

In another aspect, a method of making a compound includes contacting 1-(2-(phthalimido)ethyl)-piperazine with 1-(2-chloroethyl)imidazolidin-2-one.

In another aspect, the compound having the formula:

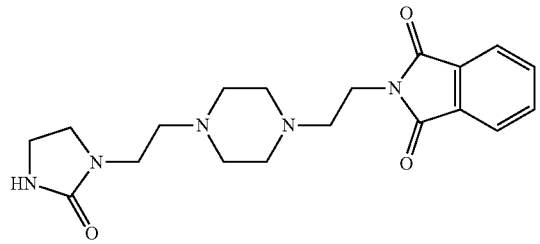 [SMILES: O=C1NCCN1CCN1CCN(CCN2C(=O)c3ccccc3C2=O)CC1]

and salts thereof.

In another aspect, the compound having the formula:

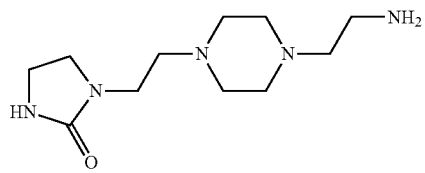 [SMILES: NCCN1CCN(CCN2CCNC2=O)CC1]

and salts thereof.

In another aspect, a method of making a compound, includes contacting 1-cyanomethyl-4-(2-((cyanomethyl)amino)ethyl)piperazine with a reducing agent.

The reducing agent can be other than $H_2$. The reducing agent can include $NaBH_4$. The method can include simultaneously contacting cyanomethyl-4-(2-((cyanomethyl)amino)ethyl)piperazine with a reducing agent and an amino group protecting reagent. The amino group protecting reagent can include $(Boc)_2O$.

BRIEF DESCRIPTION OF THE FIGURES

FIGS. 10A to 10C are graphs illustrating the knockdown (1(D) of Tie2 expression in the heart, as compared to GAPDH (FIG. 10A), VEFG Receptor 2 (VEGFR2) (FIG. 10B), and Ve-Cadherin (FIG. 10C) expression.

FIGS. 11A and 11B are graphs illustrating the KD of Tie2 expression in the liver by siRNA formulated with AF-012 (FIG. 11A), but not AF-011 (FIG. 11B).

FIGS. 12A and 12B are graphs illustrating the KD of Tie2 expression in the liver by siRNA formulated with AF-012 (FIG. 12A), and activation of VEGFR2 expression in response to the Tie2 siRNA formulated with AF-012 (FIG. 12B).

FIGS. 13A and 13B are graphs illustrating the KD of Tie2 expression in the lung by siRNA formulated with AF-012. Tie2 expression was compared with VE-Cadherin (FIG. 13A) and VEGFR-2 (FIG. 13B) expression.

DETAILED DESCRIPTION

Figure 1:
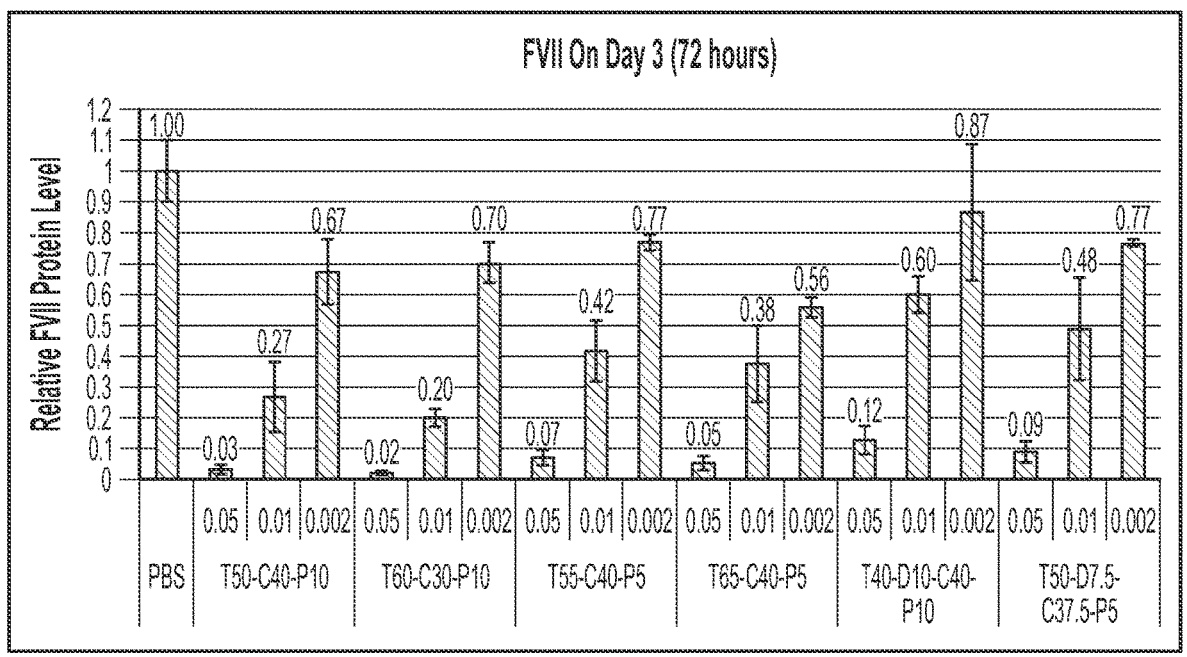
FIG. 1 is a graph showing the relative FVII protein with various lipid ratios.

The invention provides a lipid composition disclosed herein for its suitability for delivering an agent, e.g., a nucleic acid-based agent, such as an RNA-based construct, to a cell or subject. The method of administering the lipid compositions containing an RNA-based construct to an animal, and evaluating the expression of the target gene.

The invention provides a composition comprising a compound of formula (I)

formula (I)

wherein
each $X^a$ and $X^b$, for each occurrence, is independently $C_{1-6}$ alkylene;
n is 0, 1, 2, 3, 4, or 5;
A for each occurrence is $NR_2$ or a cyclic moiety optionally substituted with 1-3 R;
B is NR or a cyclic moiety optionally substituted with 1-2 R;
each R is independently H, alkyl,

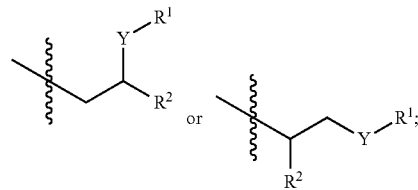

provided that at least one R is

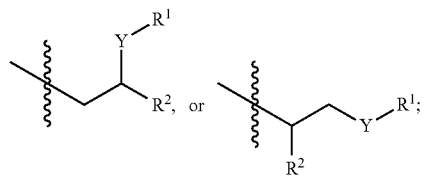

$R^1$, for each occurrence, is independently H, $R^3$,

[structures]

$R^2$, for each occurrence, is independently, alkyl, alkenyl, alkynyl, heteroalkyl, heteroalkenyl, or heteroalkynyl; each of which is optionally substituted with one or more substituent;

$R^3$, for each occurrence, is independently, alkyl, alkenyl, alkynyl, heteroalkyl, heteroalkenyl, or heteroalkynyl; each of which is optionally substituted with one or more substituent (e.g., a hydrophilic substituent);

Y, for each occurrence, is independently O, $NR^4$, or S;

$R^4$, for each occurrence is independently H alkyl, alkenyl, alkynyl, heteroalkyl, heteroalkenyl, or heteroalkynyl; each of which is optionally substituted with one or more substituent;

a sterol; and a PEG or a PEG-modified lipid.

In one embodiment, the compound of formula (I) includes at least 2 nitrogens. In one embodiment, the compound of formula (I) includes at least 3 nitrogens.

In one embodiment, n is 1, 2, or 3.

In one embodiment, at least one A is a cyclic moiety. In one embodiment, at least one A is a nitrogen containing cyclic moiety. In one embodiment, at least one A is a piperidinyl or piperizinyl moiety.

In one embodiment, n is 2 and at least one A is a cyclic moiety.

In one embodiment, at least one B is a cyclic moiety. In one embodiment, at least one B is a nitrogen containing cyclic moiety. In one embodiment, at least one B is a piperidinyl or piperizinyl moiety.

In one embodiment, n is 2 and at least one B is a cyclic moiety.

In one embodiment, $X^a$ is $C_2$ or $C_3$ alkylene. In one embodiment, $X^b$ is $C_2$ or $C_3$ alkylene.

In one embodiment, each of $X^a$ and $X^b$ are $C_2$ or $C_3$ alkylene. In one embodiment, each of $X^a$ and $X^b$ are $C_2$ alkylene.

In one embodiment, R, for at least 3 occurrences, is

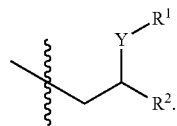

In one embodiment, n is 2 or 3 and R, for at least 3 occurrences, is

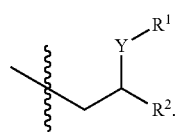

In one embodiment, n is 3 and wherein R, for 5 occurrences, is

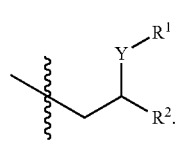

In one embodiment, R for at least 1 occurrence (e.g., 1 or 2 occurrences) is H.

In one embodiment, Y is O or $NR^4$.

In one embodiment, Y is O. In one embodiment, Y is O for each occurrence.

In one embodiment, $R^1$ is H. In one embodiment, $R^1$ is H for each occurrence.

In one embodiment, $R^1$ is

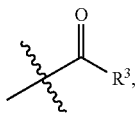

wherein $R^3$ alkyl, alkenyl, alkynyl, heteroalkyl, heteroalkenyl, or heteroalkynyl, each of which is optionally substituted with one or more substituent (e.g., a hydrophilic substituent).

In one embodiment, $R^1$ is

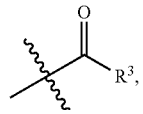

and $R^3$ alkyl optionally substituted with one or more substituent (e.g., a hydrophilic substituent).

In one embodiment, $R^3$ is substituted with —OH.

In one embodiment, $R^1$ is $R^3$,

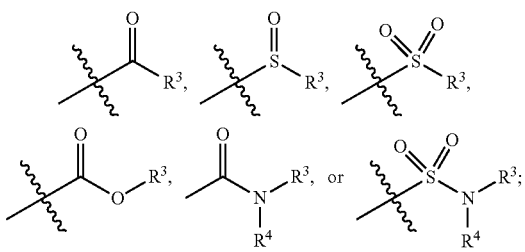

wherein $R^3$ alkyl is optionally substituted with one or more substituent.

In one embodiment, $R^3$ is substituted with a hydrophilic substituent. In one embodiment, $R^3$ is substituted with —OH.

In one embodiment, $R^2$ is alkyl, alkenyl, or alkynyl. In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, R for at least 3 (e.g., at least 4 or 5) occurrences is

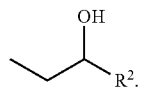

In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, the composition comprises a compound of formula (II)

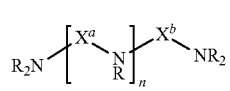

formula (II)

wherein, each $X^a$ and $X^b$, for each occurrence, is independently $C_{1-6}$ alkylene;

n is 0, 1, 2, 3, 4, or 5;

each R is independently H, alkyl,

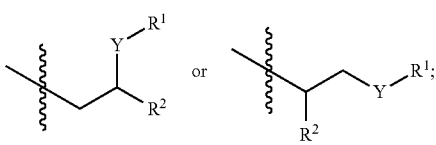

provided that at least one R is

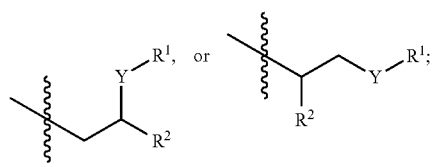

or two Rs, together with the nitrogen to which they are attached form a ring;

$R^1$, for each occurrence, is independently H, $R^3$,

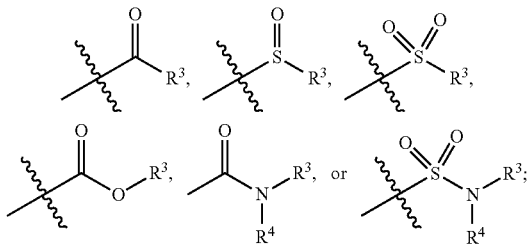

wherein $R^3$ is optionally substituted with one or more substituent;

$R^2$, for each occurrence, is independently, alkyl, alkenyl, alkynyl, heteroalkyl, heteroalkenyl, or heteroalkynyl; each of which is optionally substituted with one or more substituent;

$R^3$, for each occurrence, is independently, alkyl, alkenyl, alkynyl, heteroalkyl, heteroalkenyl, or heteroalkynyl; each of which is optionally substituted with one or more substituent;

Y, for each occurrence, is independently O, $NR^4$, or S; a sterol;

$R^4$, for each occurrence is independently H alkyl, alkenyl, alkynyl, heteroalkyl, heteroalkenyl, or heteroalkynyl; each of which is optionally substituted with one or more substituent; and a PEG or a PEG-modified lipid.

In one embodiment, r is $C_2$ or $C_3$ alkylene. In one embodiment, $X^b$ is $C_2$ or $C_3$ alkylene.

In one embodiment, each of $X^a$ and $X^b$ are $C_2$ or $C_3$ alkylene. In one embodiment, each of $X^a$ and $X^b$ are $C_2$ alkylene.

In one embodiment, n is 2 or 3.

In one embodiment, n is 3.

In one embodiment, R, for at least 3 occurrences, is

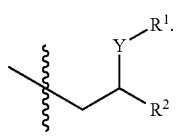

In one embodiment, n is 2 or 3 and wherein R, for at least 3 occurrences, is

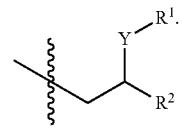

In one embodiment, n is 3 and wherein R, for 5 occurrences, is

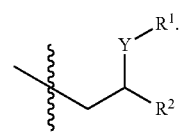

The composition of claim, x, wherein two Rs, together with the nitrogen to which they are attached form a ring. In one embodiment, the two Rs, together with the nitrogens to which they are attached forming a ring are positioned on adjacent nitrogens.

In one embodiment, Y is O or $NR^4$. In one embodiment, Y is O. In one embodiment, Y is O for each occurrence.

In one embodiment, $R^1$ is H. In one embodiment, $R^1$ is H for each occurrence.

In one embodiment, $R^1$ is

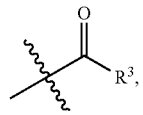

wherein $R^3$ alkyl, alkenyl, alkynyl, heteroalkyl, heteroalkenyl, or heteroalkynyl, each of which is optionally substituted with one or more substituent (e.g., a hydrophilic substituent). In one embodiment, $R^1$ is

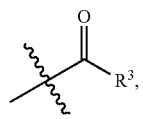

and $R^3$ alkyl optionally substituted with one or more substituent (e.g., a hydrophilic substituent).

In one embodiment, $R^3$ is substituted with —OH.

In one embodiment, $R^1$ is $R^3$,

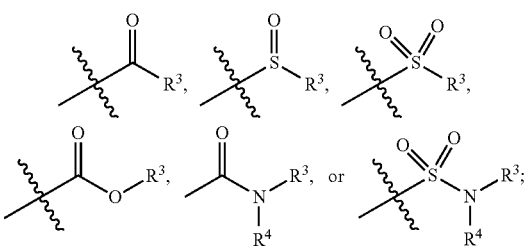

wherein $R^3$ alkyl is optionally substituted with one or more substituent.

In one embodiment, $R^3$ is substituted with a hydrophilic substituent. In one embodiment, $R^3$ is substituted with —OH.

In one embodiment, $R^2$ is alkyl, alkenyl, or alkynyl. In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, R for at least 3 (e.g., at least 4 or 5) occurrences is

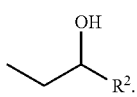

In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, R for at least 1 occurrence (e.g., 1 or 2 occurrences) is H.

In one embodiment, the composition comprises a compound of formula (III), (VI), or mixture thereof, formula (III)

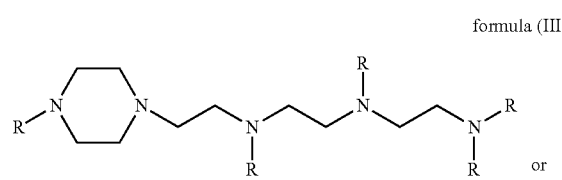

or formula (IV)

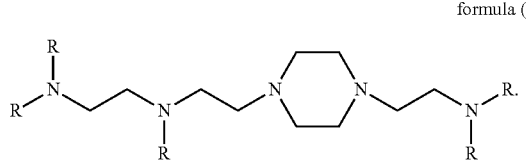

In one embodiment, R, for at least 3 occurrences, is

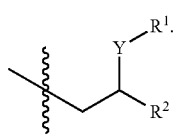

In one embodiment, n is 2 or 3 and wherein R, for at least 3 occurrences, is

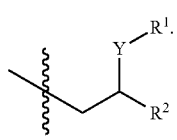

In one embodiment, n is 3 and wherein R, for 5 occurrences, is

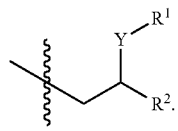

In one embodiment, Y is O or $NR^4$. In one embodiment, Y is O. In one embodiment, Y is O for each occurrence.

In one embodiment, $R^1$ is H. In one embodiment, $R^1$ is H for each occurrence. In one embodiment, $R^1$ is

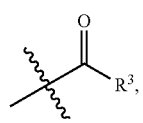

wherein $R^3$ alkyl, alkenyl, alkynyl, heteroalkyl, heteroalkenyl, or heteroalkynyl, each of which is optionally substituted with one or more substituent (e.g., a hydrophilic substituent). In one embodiment, $R^1$ is

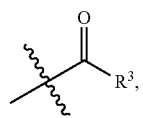

and $R^3$ alkyl optionally substituted with one or more substituent (e.g., a hydrophilic substituent).

In one embodiment, $R^3$ is substituted with —OH.

In one embodiment, $R^1$ is $R^3$,

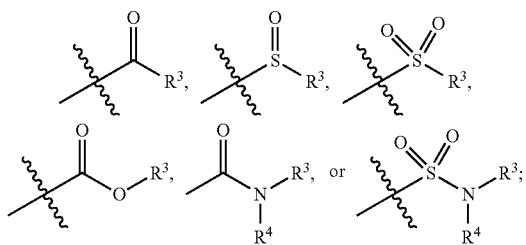

wherein $R^3$ alkyl is optionally substituted with one or more substituent.

In one embodiment, $R^3$ is substituted with a hydrophilic substituent. In one embodiment, $R^3$ is substituted with —OH.

In one embodiment, $R^2$ is alkyl, alkenyl, or alkynyl. In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, R for at least 3 (e.g., at least 4 or 5) occurrences is

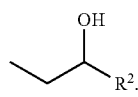

In one embodiment, $R^2$ is alkyl (e.g., $C_6$-$C_{18}$ alkyl, e.g., $C_8$-$C_{12}$ alkyl, e.g., $C_{10}$ alkyl). In one embodiment, $R^2$ is alkyl (e.g., $C_6$-$C_{18}$ alkyl, e.g., $C_8$-$C_{12}$ alkyl, e.g., $C_{10}$ alkyl).

In one embodiment, R for at least 1 occurrence (e.g., 1 or 2 occurrences) is H.

In one embodiments, the composition comprises a compound of formula (V)

formula (V). In one embodiment, the composition comprises a compound of formula (VI)

formula (VI)

In one embodiment, the composition includes a compound of formula (VII):

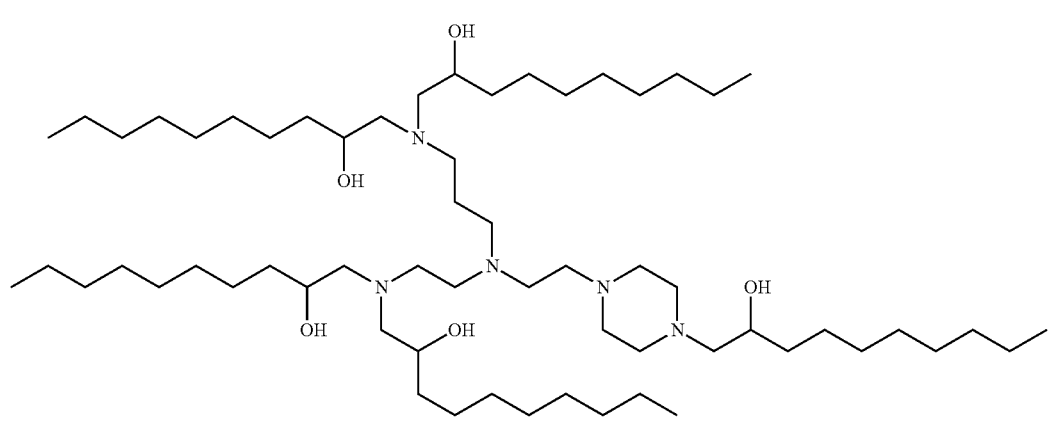

(VII)

In one embodiment, the compound of formula (I), (II), (III), (IV), (V), (VI) or (VII) is an inorganic or organic salt thereof, e.g., a hydrohalide salt thereof, such as a hydrochloride salt thereof. In one embodiment, the compound of formula (I), (II), (III), (IV), (V), (VI) or (VII) is salt of an organic acid, e.g., an acetate or formate. In one embodiment, the compound of formula (I), (II), (III), (IV), (V), (VI) or (VII) is in the form of a hydrate.

In one embodiment, the sterol is cholesterol. In one embodiment, the lipid is a PEG-modified lipid. In one embodiment, the PEG-modified lipid is PEG-DMG.

In one embodiment, the composition further comprises a neutral lipid. In one embodiment, the neutral lipid is DSPC.

In one embodiment, the composition comprises about 25-75% of the compound of formula (I) (e.g., a compound of formula (II), (III), (IV), (V), (VI) or (VII)), about 5-50% of the sterol, and about 0.5-20% of the PEG or PEG-modified lipid. In one embodiment, the composition further comprises about 0.5-15% of the neutral lipid.

In one embodiment, the composition comprises about 35-65% the compound of formula (I) (e.g., a compound of formula (II), (III), (IV), (V), (VI) or (VII)), about 15-45% of the sterol, and about 0.5-10% of the PEG or PEG-modified lipid.

In one embodiment, the composition further comprises about 3-12% of the neutral lipid.

In one embodiment, the composition comprises about 45-65% of the compound of formula (I) (e.g., a compound of formula (II), (III), (IV), (V), (VI) or (VII)), about 25-40% of the sterol, and about 0.5-5% of the PEG or PEG-modified lipid.

In one embodiment, the composition further comprises about 5-10% of the neutral lipid, In one embodiment, the composition comprises about 60% of the compound of formula (I) (e.g., a compound of formula (II), (III), (IV), (V), (VI) or (VII)), about 31% of the sterol, and about 1.5% of the PEG or PEG-modified lipid. In one embodiment, the composition further comprises about 7.5% of the neutral lipid.

In one embodiment, the compositions of the inventions include about 57.5% of cationic lipid of formula (I) (e.g., a compound of formula (II), (III), (IV), (V), (VI) or (VII)), about 7.5% of the neutral lipid, about 31.5% of the sterol, and about 3.5% of the PEG or PEG-modified lipid. In one preferred embodiment, the cationic lipid of formula (I) is the compound of formula V, the neutral lipid is DSPC, the sterol is cholesterol and the PEG lipid is PEG-DMG.

In one embodiment, the compositions of the inventions include about 50% of cationic lipid of formula (I) (e.g., a lipid of formula (II), (III), (IV), (V), (VI) or (VII)), about 10% of the neutral lipid, about 38.5% of the sterol, and about 1.5% of the PEG or PEG-modified lipid. In one preferred embodiment, the cationic lipid of formula (I) is a lipid of formula V, the neutral lipid is DSPC, the sterol is cholesterol and the PEG lipid is PEG-DMG.

In one embodiment, the compositions of the inventions include about 50% of cationic lipid of formula (I) (e.g., a lipid of formula (II), (III), (IV), (V), (VI) or (VII)), about 10% of the neutral lipid, about 38.5% of the sterol, and about 1.5% of the PEG or PEG-modified lipid. In one preferred embodiment, the cationic lipid of formula (I) is a lipid of formula V, the neutral lipid is DSPC, the sterol is cholesterol and the PEG lipid is PEG-DSG.

In one embodiment, the compositions of the inventions include about 50% of cationic lipid of formula (I) (e.g., a lipid of formula (II), (III), (IV), (V), (VI) or (VII)), about 10% of the neutral lipid, about 38.5% of the sterol, and about 1.5% of the PEG or PEG-modified lipid. In one preferred embodiment, the cationic lipid of formula (I) is a lipid of formula VI, the neutral lipid is DSPC, the sterol is cholesterol and the PEG lipid is PEG-DMG.

In one embodiment, the compositions of the inventions include about 50% of cationic lipid of formula (I) (e.g., a lipid of formula (II), (III), (IV), (V), (VI) or (VII)), about 10% of the neutral lipid, about 38.5% of the sterol, and about 1.5% of the PEG or PEG-modified lipid. In one preferred embodiment, the cationic lipid of formula (I) is a lipid of formula VI, the neutral lipid is DSPC, the sterol is cholesterol and the PEG lipid is PEG-DSG.

In one embodiment, the composition is an association complex. In one embodiment, the composition is a liposome.

In one embodiment, the composition further comprises a nucleic acid agent (e.g., one or more nucleic acid agents).

In one embodiment, the composition further comprises an RNA agent. In one embodiment, the composition further comprises a single stranded RNA agent (e.g., one or more single stranded RNA agents). In one embodiment, the composition further comprises a double stranded RNA agent (e.g., one or more double stranded RNA agents).

In one embodiment, the lipid composition may comprise more than one siRNA. In some embodiments, the lipid composition comprises two or more different siRNAs. In some embodiments, the lipid composition comprises five or more different siRNAs. In some embodiments, the lipid composition comprises ten or more differents siRNAs. In some embodiment, the lipid composition comprises twenty or more different siRNAs.

A composition, the composition comprising a compound of formula (III) or (VI) or a mixture thereof

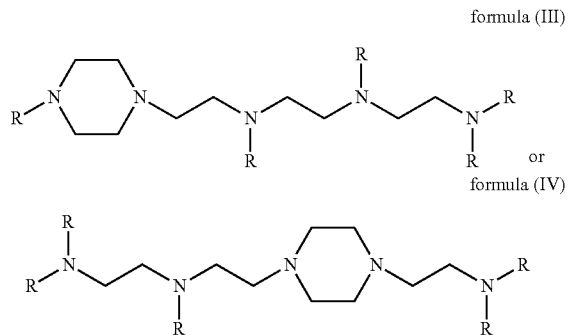

formula (III)

formula (IV)

wherein
each R is independently H, alkyl,

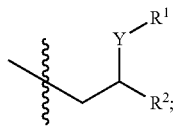

$R^1$, for each occurrence, is independently H, $R^3$,

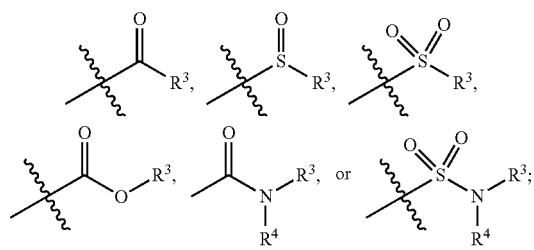

$R^2$, for each occurrence, is independently, alkyl, alkenyl, alkynyl, heteroalkyl, heteroalkenyl, or heteroalkynyl; each of which is optionally substituted with one or more substituent;

$R^3$, for each occurrence, is independently, alkyl, alkenyl, alkynyl, heteroalkyl, heteroalkenyl, or heteroalkynyl; each of which is optionally substituted with one or more substituent (e.g., a hydrophilic substituent);

Y, for each occurrence, is independently O, $NR^4$, or S;

$R^4$, for each occurrence is independently H alkyl, alkenyl, alkynyl, heteroalkyl, heteroalkenyl, or heteroalkynyl; each of which is optionally substituted with one or more substituent;

a sterol; and
a PEG or a PEG-modified lipid.

A method of producing a composition described herein, the method comprising an extrusion method or an in-line mixing method.

In one embodiment, the compositions of the inventions include 25-75% of cationic lipid of formula (I) (e.g., a lipid of formula (II), (III), (IV), (V), (VI) or (VII)), of the neutral lipid, 5-50% of the sterol, and 0.5-20% of the PEG or PEG-modified lipid.

In one embodiment, the compositions of the inventions include 35-65% of cationic lipid of formula (I) (e.g., a lipid of formula (II), (III), (IV), (V), (VI) or (VII)), 3-12% of the neutral lipid, 15-45% of the sterol, and 0.5-10% of the PEG or PEG-modified lipid.

In one embodiment, the compositions of the inventions include 45-65% of cationic lipid of formula (I) (e.g., a lipid of formula (II), (III), (IV), (V), (VI) or (VII)), of the neutral lipid, 25-40% of the sterol, and 0.5-5% of the PEG or PEG-modified lipid.

In one embodiment, the compositions of the inventions include about 60% of cationic lipid of formula (I) (e.g., a lipid of formula (II), (III), (IV), (V), (VI) or (VII)), about 7.5% of the neutral lipid, about 31% of the sterol, and about 1.5% of the PEG or PEG-modified lipid. In one preferred embodiment, the cationic lipid of formula (I) is the compound of formula V, the neutral lipid is DSPC, the sterol is cholesterol and the PEG lipid is PEG-DMG.

In one embodiment, the compositions of the inventions include about 57.5% of cationic lipid of formula (I) (e.g., a lipid of formula (II), (III), (IV), (V), (VI) or (VII)), about 7.5% of the neutral lipid, about 31.5% of the sterol, and about 3.5% of the PEG or PEG-modified lipid. In one preferred embodiment, the cationic lipid of formula (I) is the compound of formula V, the neutral lipid is DSPC, the sterol is cholesterol and the PEG lipid is PEG-DMG.

In one embodiment, the ratio of lipid:siRNA is at least about 0.5:1, at least about 1:1, at least about 2:1, at least about 3:1, at least about 4:1, at least about 5:1, at least about 6:1, at least about 7:1, at least about 8:1, at least about 9:1, at least about or at least about 11:1. In one embodiment, the ratio of lipid:siRNA ratio is between about 1:1 to about 20:1, about 3:1 to about 15:1, about 4:1 to about 15:1, about 5:1 to about 13:1. In one embodiment, the ratio of lipid:siRNA ratio is between about 0.5:1 to about 12:1.

In one aspect, the lipid composition also includes a targeting lipid. In some embodiments, the targeting lipid includes a GalNAc moiety (i.e., an N-galactosamine moiety). For example, a targeting lipid including a GalNAc moiety can include those disclosed in U.S. Ser. No. 12/328, 669, filed Dec. 4, 2008, which is incorporated herein by reference in its entirety. A targeting lipid can also include any other lipid (e.g., targeting lipid) known in the art, for example, as described in U.S. Ser. No. 12/328,669 or International Publication No. WO 2008/042973, the contents of each of which are incorporated herein by reference in their entirety. In some embodiments, the targeting lipid includes a plurality of GalNAc moieties, e.g., two or three GalNAc moieties. In some embodiments, the targeting lipid contains a plurality, e.g., two or three N-acetylgalactosamine (GalNAc) moieties. In some embodiments, the lipid in the targeting lipid is 1,2-Di-O-hexadecyl-sn-glyceride (i.e., DSG). In some embodiments, the targeting lipid includes a PEG moiety (e.g., a PEG moiety having a molecular weight of at least about 500 Da, such as about 1000 Da, 1500 Da, 2000 Da or greater), for example, the targeting moiety is connected to the lipid via a PEG moiety.

In some embodiments, the targeting lipid includes a folate moiety. For example, a targeting lipid including a folate moiety can include those disclosed in U.S. Ser. No. 12/328, 669, filed Dec. 4, 2008, which is incorporated herein by reference in its entirety. In another embodiment, a targeting lipid including a folate moiety can include the compound of formula 5.

Exemplary targeting lipids are represented by formula L below:

(Targeting group)$_n$-L-Lipid             formula L wherein:

Targeting group is any targeting group that known by one skilled in the art and/or described herein (e.g., a cell surface receptor);

n is an integer from 1 to 5, (e.g., 3)

L is a linking group; and

Lipid is a lipid such as a lipid described herein (e.g., a neutral lipid such as DSG).

In some embodiments, the linking group includes a PEG moiety. In another embodiment, the PEG moiety can vary in size from a molecular weight of about 1,000 to about 20,000 daltons (e.g., from about 1,500 to about 5,000 daltons, e.g., about 1000 daltons, about 2000 daltons, about 3400 daltons, or about 5000 daltons.

In some embodiments, the targeting lipid is a compound of formula 2, 3, 4, 5, 6 or 7 as provided below:

Formula 2

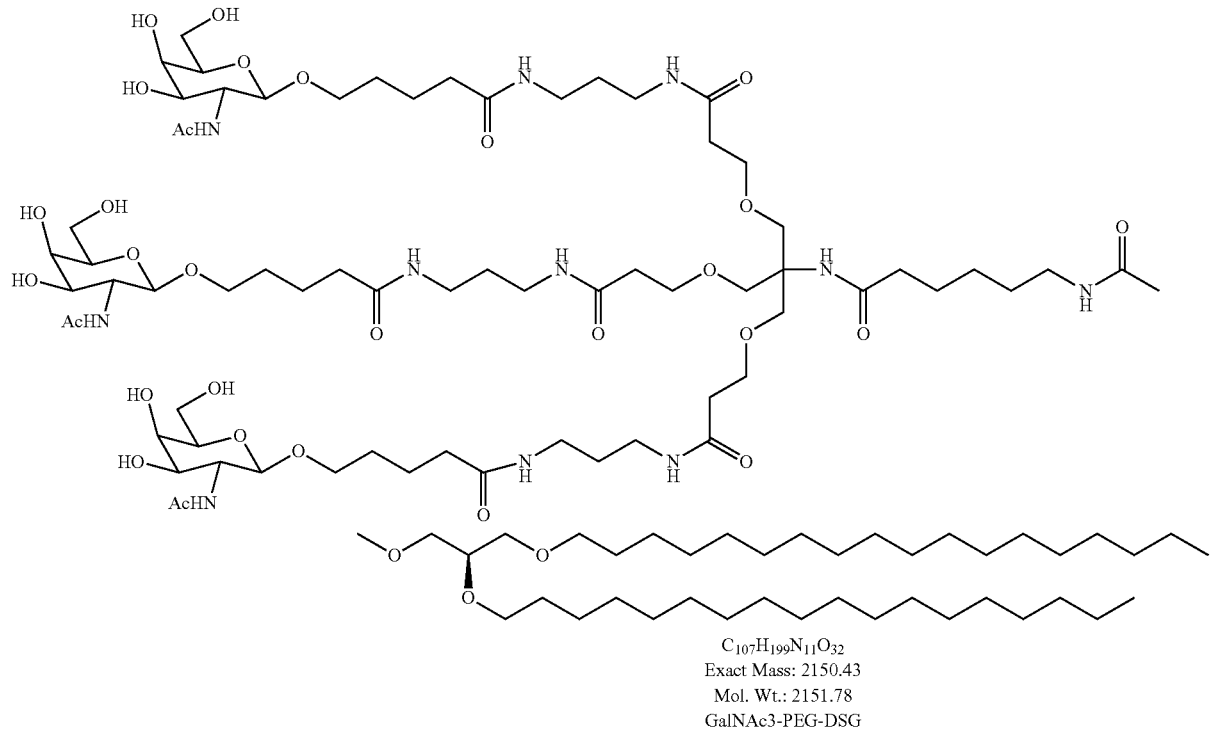

$C_{107}H_{199}N_{11}O_{32}$
Exact Mass: 2150.43
Mol. Wt.: 2151.78
GalNAc3-PEG-DSG Formula 3

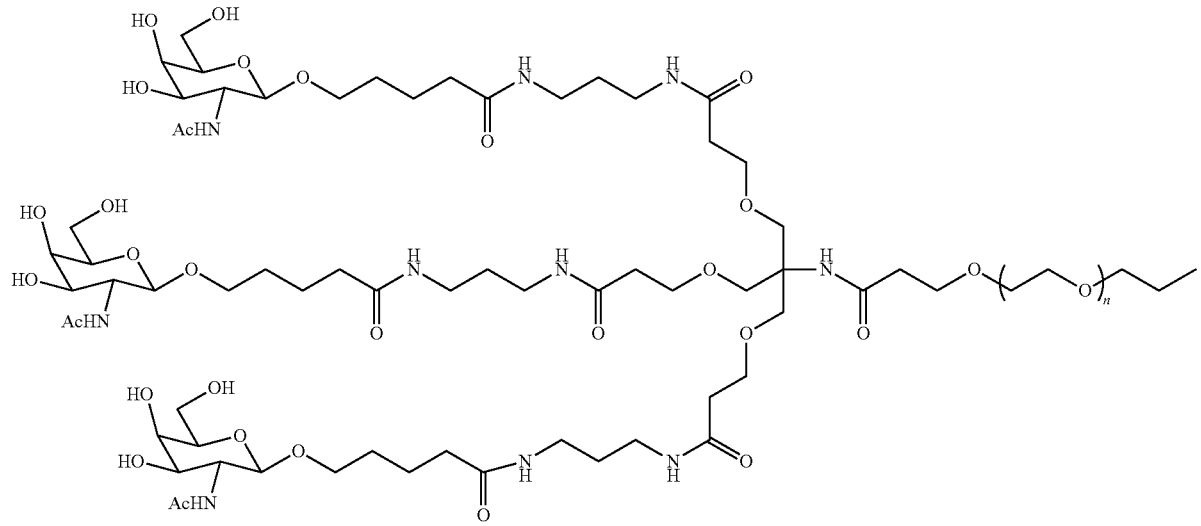

-continued
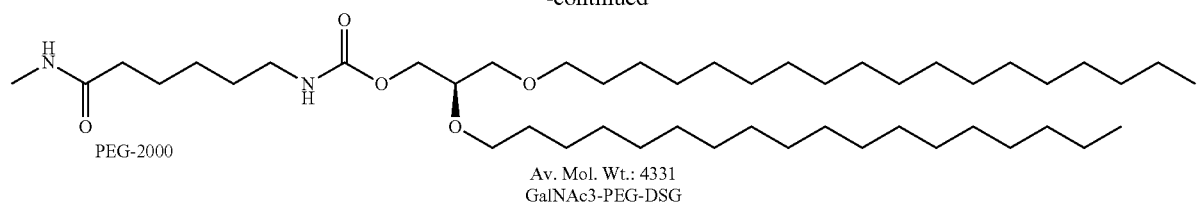
Formula 4
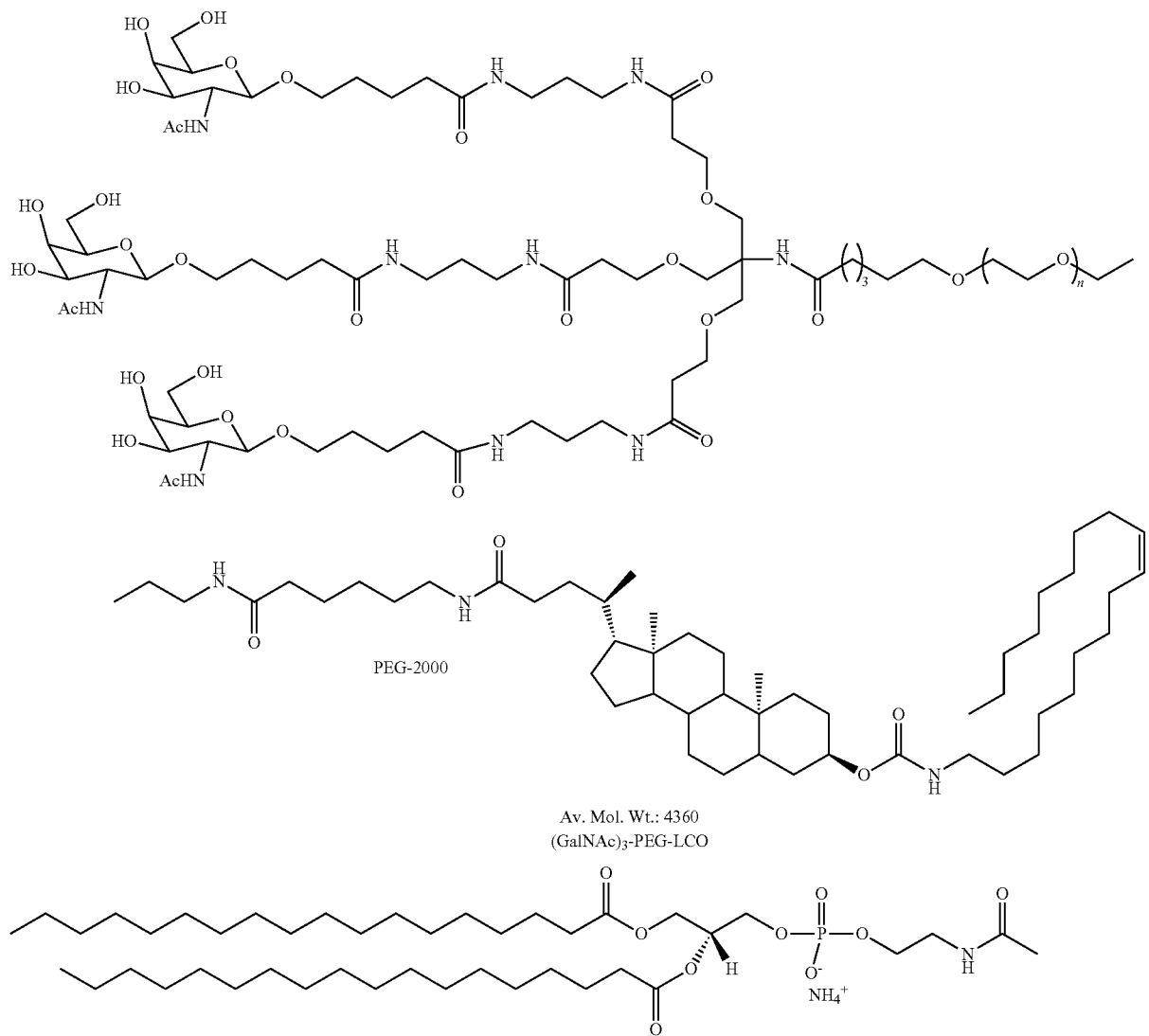
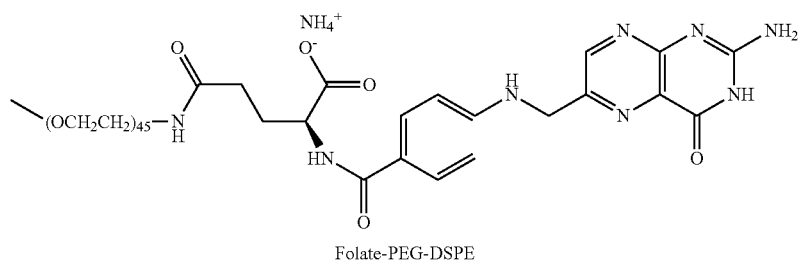

1,2-distearoyl-sn-glycero-3-phosphoethanolamine-N-[folate(polyethylene glycol)-2000] (Ammonium Salt)

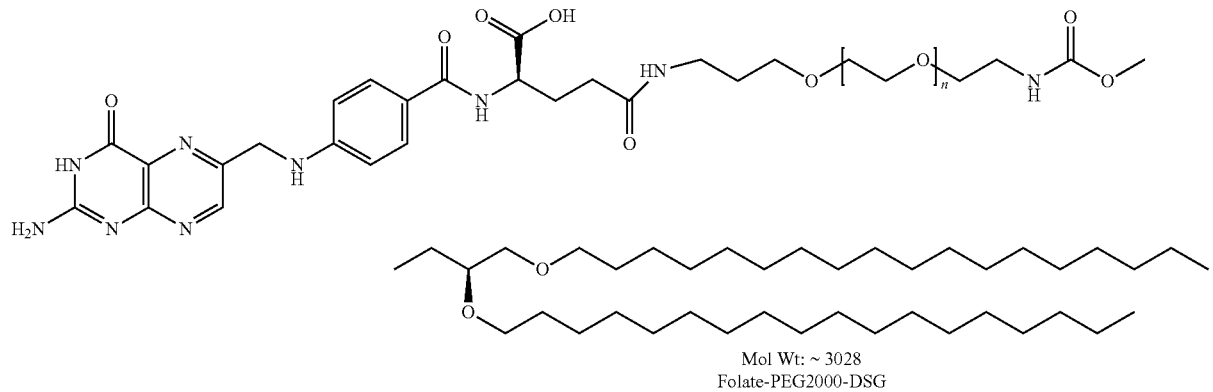

Formula 6

Mol Wt: ~ 3028
Folate-PEG2000-DSG

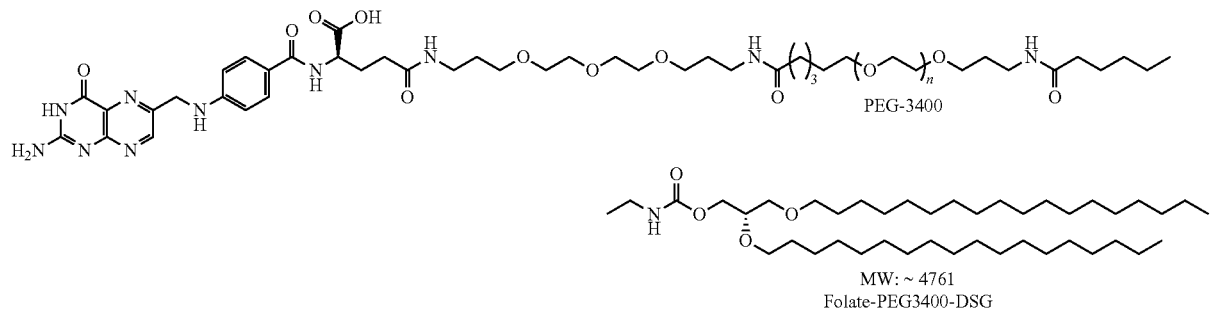

Formula 7

MW: ~ 4761
Folate-PEG3400-DSG

In some embodiments, the targeting lipid is present in the composition in an amount of from about 0.001% to about 5% (e.g., about 0.005%, 0.15%, 0.3%, 0.5%, 1.5%, 2%, 2.5%, 3%, 4%, or 5%) on a molar basis. In some embodiments, the targeting lipid is included in a composition described herein.

In some embodiments, the lipid composition also included an antioxidant (e.g., a radical scavenger). The antioxidant can be present in the composition, for example, at an amound from about 0.01% to about 5%. The antioxidant can be hydrophobic or hydrophilic (e.g., soluble in lipids or soluble in water). In some embodiments, the antioxidant is a phenolic compound, for example, butylhydroxytoluene, resveratrol, coenzyme Q10, or other flavinoids, or a vitamin, for example, vitamin E or vitamin C. Other exemplary antioxidants include lipoic acid, uric acid, a carotene such as beta-carotene or retinol (vitamin A), glutathione, melatonin, selenium, and ubiquinol.

In some embodiments, the receptor for the targeting lipid (e.g., a GalNAc containing lipid) is the asialoglycoprotein receptor (i.e., ASGPR).

In one embodiment, the compositions of the invention are produced via an extrusion method or an in-line mixing method.

The extrusion method (also refer to as preformed method or batch process) is a method where the empty liposomes (i.e. no nucleic acid) are prepared first, followed by the addition of nucleic acid to the empty liposome. Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing. These methods are disclosed in the U.S. Pat. Nos. 5,008,050; 4,927,637; 4,737,323; Biochim Biophys Acta. 1979 Oct. 19; 557(1):9-23; Biochim Biophys Acta. 1980 Oct. 2; 601(3):559-7; Biochim Biophys Acta. 1986 Jun. 13; 858(1):161-8; and Biochim. Biophys. Acta 1985 812, 55-65, which are hereby incorporated by reference in their entirety.

The in-line mixing method is a method wherein both the lipids and the nucleic acid are added in parallel into a mixing chamber. The mixing chamber can be a simple T-connector or any other mixing chamber that is known to one skill in the art. These methods are disclosed in U.S. Pat. Nos. 6,534,018 and 6,855,277; US publication 2007/0042031 and Pharmaceuticals Research, Vol. 22, No. 3, March 2005, p. 362-372, which are hereby incorporated by reference in their entirety.

It is further understood that the compositions of the invention can be prepared by any methods known to one of ordinary skill in the art.

In a further embodiment, representative compositions prepared via the extrusion method or in-line mixing method are delineated in Table 1, wherein Lipid T is

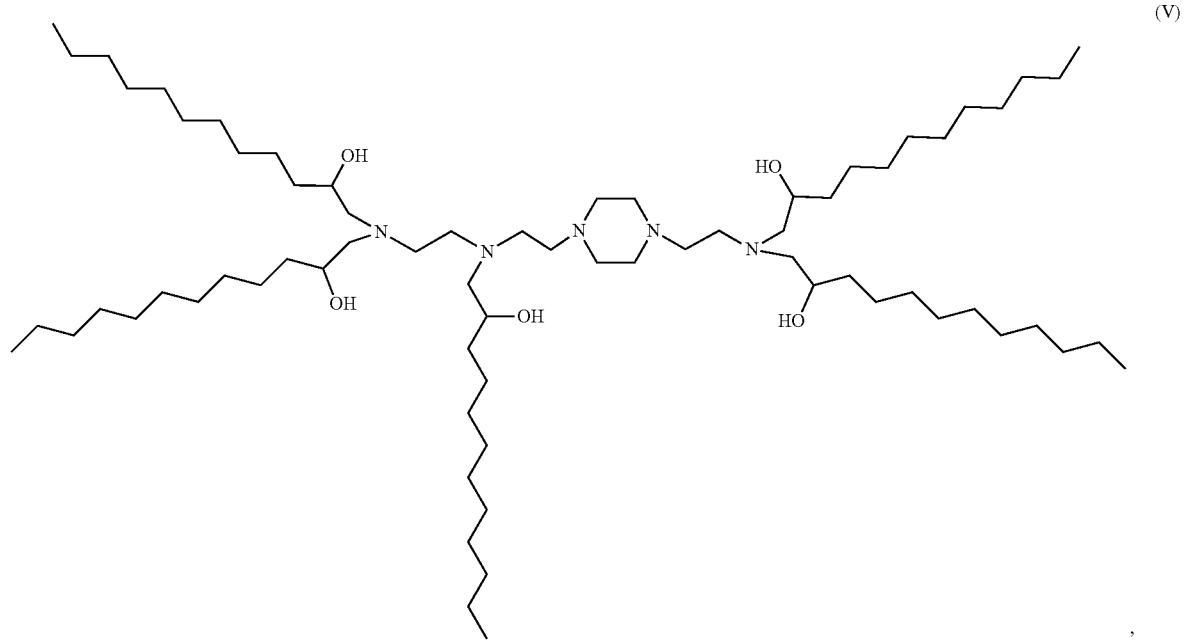 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]
(V)
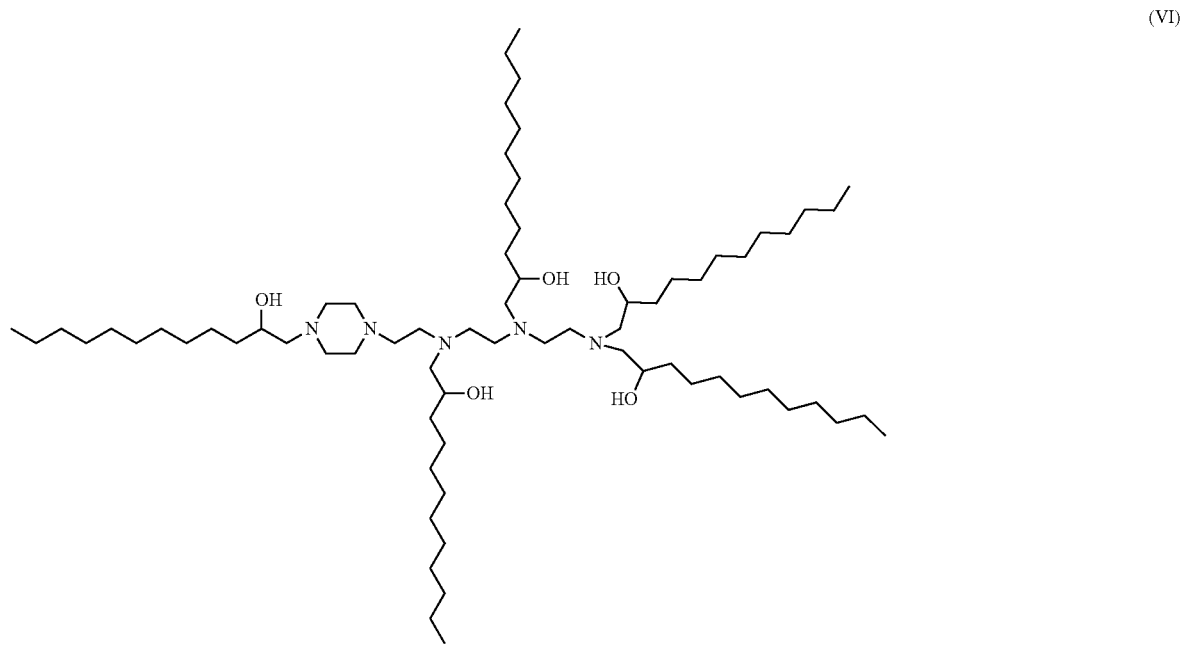
(VI)

or a combination thereof:

TABLE 1

| Theoretical Composition (mole %) | | | | | Initial | | | Final (Entrapped) | | particle size (nm) | | |
|---|---|---|---|---|---|---|---|---|---|---|---|---|
| Lipid T | DSPC | Chol | PEG (C14) | siRNA | Lipid T/ siRNA | Total Lipid/ siRNA | Entrapment (%) | Lipid T/ siRNA | Total Lipid/ siRNA | Peak | width | PDI |
| 42 | 0 | 28 | 10 | 1661 | 4.75 | 9 | 58 | 8.19 | 15.52 | 89.6 | 31.7 | 0.133 |
| 42 | 0 | 28 | 10 | 1661 | 4.75 | 9 | 77 | 6.17 | 11.69 | 126 | 43.6 | 0.07 |
| 42 | 0 | 28 | 10 | 1661 | 4.75 | 9 | 24 | 19.79 | 37.50 | 37.3 | 13.4 | 0.194 |
| 50 | 0 | 40 | 10 | 1661 | 4.75 | 8.19 | 58 | 8.19 | 14.12 | 121 | 47.5 | 0.109 |
| 60 | 0 | 30 | 10 | 1661 | 4.75 | 7.35 | 43 | 11.05 | 17.09 | 117 | 48.1 | 0.095 |
| 55 | 0 | 40 | 5 | 1661 | 4.75 | 6.9 | 62 | 7.66 | 11.13 | 160 | 64.2 | 0.096 |
| 65 | 0 | 30 | 5 | 1661 | 4.75 | 6.32 | 41 | 11.59 | 15.41 | 164 | 59 | 0.086 |
| 40 | 10 | 40 | 10 | 1661 | 4.75 | 9.05 | 72 | 6.60 | 12.57 | 118 | 46.4 | 0.113 |
| 50 | 7.5 | 37.5 | 5 | 1661 | 4.75 | 7.03 | 79 | 6.01 | 8.90 | 131 | 61.1 | 0.126 |
| 50 | 0 | 40 | 10 | 1661 | 4.75 | 8.19 | 57 | 8.33 | 14.37 | 88.3 | 28.9 | 0.068 |
| 60 | 0 | 30 | 10 | 1661 | 4.75 | 7.35 | 35 | 13.57 | 21.00 | 84.7 | 33.6 | 0.099 |
| 55 | 0 | 40 | 5 | 1661 | 4.75 | 6.9 | 49 | 9.69 | 14.08 | 136 | 33.3 | 0.029 |
| 65 | 0 | 30 | 5 | 1661 | 4.75 | 6.32 | 26 | 18.27 | 24.31 | 98.3 | 33.2 | 0.096 |
| 40 | 10 | 40 | 10 | 1661 | 4.75 | 9.05 | 70 | 6.79 | 12.93 | 80.2 | 30.4 | 0.14 |
| 50 | 7.5 | 37.5 | 5 | 1661 | 4.75 | 7.03 | 68 | 6.99 | 10.34 | 103 | 33.9 | 0.082 |
| 57.5 | 7.5 | 31.5 | 3.5 | 1661 | 4.75 | 6.29 | 66 | 7.20 | 9.53 | 101 | 19.4 | 0.344 |
| 57.5 | 7.5 | 31.5 | 3.5 | 1661 | 4.75 | 6.29 | 83 | 5.72 | 7.58 | 144 | 58.4 | 0.087 |
| 57.5 | 7.5 | 31.5 | 3.5 | 1661 | 4.75 | 6.29 | 90 | 5.28 | 6.99 | 181 | 58.6 | 0.042 |
| 57.5 | 7.5 | 31.5 | 3.5 | 1661 | 4.75 | 6.29 | 60 | 7.92 | 10.48 | 95.2 | 33.1 | 0.153 |
| 40 | 7.5 | 32.5 | 20 | 1661 | 4.75 | 11.43 | 74 | 6.42 | 15.45 | 77.8 | 34.2 | 0.131 |
| 50 | 7.5 | 22.5 | 20 | 1661 | 4.75 | 9.77 | 48 | 9.90 | 20.35 | 96.5 | 37.7 | 0.152 |
| 57.5 | 7.5 | 31.5 | 3.5 | 1661 | 4.75 | 6.29 | 54 | 8.80 | 11.65 | 86.9 | 34.9 | 0.094 |
| 40 | 7.5 | 32.5 | 20 | 1661 | 4.75 | 11.43 | 76 | 6.25 | 15.04 | 85.3 | 33.6 | 0.096 |
| 57.5 | 7.5 | 31.5 | 3.5 | 1661 | 4.75 | 6.29 | 10 | 47.50 | 62.90 | 107 | 58.4 | 0.148 |
| 57.5 | 7.5 | 31.5 | 3.5 | 1661 | 4.75 | 6.29 | 82 | 5.79 | 7.67 | 150 | 59.3 | 0.092 |
| 57.5 | 7.5 | 31.5 | 3.5 | 1661 | 4.75 | 6.29 | 73 | 6.51 | 8.62 | 113 | 37.1 | 0.094 |
| 57.5 | 7.5 | 31.5 | 3.5 | 1661 | 4.75 | 6.29 | 71 | 6.69 | 8.86 | 115 | 37.9 | 0.068 |
| 57.5 | 7.5 | 31.5 | 3.5 | 1661 | 4.75 | 6.72 | 13 | 36.54 | 51.69 | 39.9 | 12 | 0.265 |
| 57.5 | 7.5 | 31.5 | 3.5 | 1661 | 4.75 | 6.29 | 40 | 11.88 | 15.73 | 55.6 | 18.9 | 0.109 |
| 50 | 7.5 | 37.5 | 5 | 1955 | 4.75 | 7.03 | 93 | 5.11 | 7.56 | 122 | 45.7 | 0.083 |
| 50 | 7.5 | 37.5 | 5 | 3215 | 4.75 | 7.03 | 79 | 6.01 | 8.90 | 102 | 35 | 0.122 |
| 60 | 7.5 | 31 | 1.5 | 1661 | 4.75 | 6.26 | 79 | 6.01 | 7.92 | 191 | 70.5 | 0.096 |
| 55 | 7.5 | 32.5 | 5 | 1661 | 4.75 | 7.13 | 80 | 5.94 | 8.91 | 132 | 41 | 0.056 |
| 55 | 7.5 | 32.5 | 5 | 1661 | 4.75 | 7.13 | 40 | 11.88 | 17.83 | 73.2 | 24.6 | 0.096 |
| 55 | 7.5 | 32.5 | 5 | 1661 | 4.75 | 7.13 | 43 | 11.05 | 16.58 | 71.6 | 20 | 0.07 |
| 60 | 7.5 | 31 | 1.5 | 1661 | 4.75 | 6.26 | 60 | 7.92 | 10.43 | 61.9 | 19.7 | 0.064 |
| 60 | 7.5 | 31.5 | 1 | 1661 | 4.75 | 6.19 | 48 | 9.90 | 12.90 | 113 | 93.8 | 0.238 |
| 60 | 7.5 | 31 | 1.5 | 1661 | 4.75 | 6.26 | 41 | 11.59 | 15.27 | 156 | 81.1 | 0.132 |
| 60 | 7.5 | 31 | 1.5 | 1661 | 4.75 | 6.26 | 29 | 16.38 | 21.59 | 115 | 79.8 | 0.204 |
| 60 | 0 | 38.5 | 1.5 | 1661 | 4.75 | 6.05 | 17 | 27.94 | 35.59 | 139 | 77.8 | 0.184 |
| 60 | 7.5 | 31 | 1.5 | 1661 | 4.75 | 6.26 | 73 | 6.51 | 8.58 | 75.1 | 19.6 | 0.04 |
| 60 | 7.5 | 31 | 1.5 | 1661 | 4.75 | 6.26 | 74 | 6.42 | 8.46 | 71.3 | 25.7 | 0.091 |
| 60 | 7.5 | 31 | 1.5 | 1661 | 4.75 | 6.26 | 69 | 6.88 | 9.07 | 80.1 | 28 | 0.082 |
| 60 | 7.5 | 31 | 1.5 | 1661 | 9.5 | 12.53 | 70 | 13.57 | 17.90 | 69.8 | 22.5 | 0.09 |
| 50 | 10 | 38.5 | 1.5 | 1661 | 4.75 | 6.97 | 77 | 6.17 | 9.05 | 64 | 26.1 | 0.127 |
| 60 | 0 | 38.5 | 1.5 | 1661 | 4.75 | 6.05 | 51 | 9.31 | 11.86 | 64 | 21.9 | 0.088 |
| 40 | 20 | 38.5 | 1.5 | 1661 | 4.75 | 8.36 | 86 | 5.52 | 9.72 | 59.7 | 21.1 | 0.151 |
| 50 | 10 | 38.5 | 1.5 | 18747 | 4.75 | 6.97 | N/A | N/A | N/A | 70.3 | 22.6 | 0.034 |
| 45 | 15 (DOPC) | 38.5 | 1.5 | 1661 | 4.75 | 7.58 | 82 | 5.79 | 9.24 | 70 | 19.4 | 0.043 |
| 45 | 15 (DMPC) | 38.5 | 1.5 | 1661 | 4.75 | 7.43 | 81 | 5.86 | 9.17 | 57.2 | 17.1 | 0.081 |
| 45 | 15 | 38.5 | 1.5 | 1661 | 4.75 | 7.59 | 81 | 5.86 | 9.37 | 54.4 | 17.3 | 0.118 |
| 50 | 10 | 38.5 | 1.5 (C10) | 1661 | 4.75 | 6.97 | 79 | 6.01 | 8.82 | 75.5 | 45.2 | 0.2 |
| 50 | 10 | 38.5 | 1.5 (C18) | 1661 | 4.75 | 6.98 | 81 | 5.86 | 8.62 | 64.1 | 18.4 | 0.069 |

In one embodiment, the compositions of the invention are entrapped by at least 60%, at least 65%, at least 75%, at least 80% or at least 90%.

In one embodiment, the compositions of the invention further comprise a buffer (e.g. citrate, phosphate).

In one embodiment, the compositions of the invention further comprise an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-I$_M$) and ApoA-I Paris (ApoA-I$_P$) which contain one cysteine residue (Jia et al., 2002, Biochem. Biophys. Res. Comm. 297: 206-13; Bielicki and Oda, 2002, Biochemistry 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077-9083; and Rall, et al., "Structural basis for receptor binding heterogeneity of apolipoprotein E from type III hyperlipoproteinemic subjects," Proc. Nat. Acad. Sci. (1982) 79: 4696-4700. See also GenBank accession number K00396.

In certain embodiments, the apolipoprotein can be in its mature form, in its preproapolipoprotein form or in its proapolipoprotein form. Homo- and heterodimers (where feasible) of pro- and mature ApoA-I (Duverger et al., 1996, Arterioscler. Thromb. Vasc. Biol. 16(12):1424-29), ApoA-I Milano (Klon et al., 2000, Biophys. J. 79:(3)1679-87; Franceschini et al., 1985, J. Biol. Chem. 260: 1632-35), ApoA-I Paris (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-35), ApoA-IV (Duverger et al., 1991, Euro. J. Biochem. 201(2): 373-83), and ApoE (McLean et al., 1983, J. Biol. Chem. 258(14):8993-9000) can also be utilized within the scope of the invention.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as isoleucine, valine, leucine or methionine for another. Likewise, the present invention contemplates, for example, the substitution of at least one hydrophilic residue such as, for example, between arginine and lysine, between glutamine and asparagine, and between glycine and serine (see U.S. Pat. Nos. 6,004,925, 6,037,323 and 6,046,166). The term "isoform" refers to a protein having the same, greater or partial function and similar, identical or partial sequence, and may or may not be the product of the same gene and usually tissue specific (see Weisgraber 1990, J. Lipid Res. 31(8):1503-11; Hixson and Powers 1991, J. Lipid Res. 32(9):1529-35; Lackner et al., 1985, J. Biol. Chem. 260(2): 703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sacre et al., 2003, FEBS Lett. 540(1-3): 181-7; Weers, et al., 2003, Biophys. Chem. 100(1-3):481-92; Gong et al., 2002, J. Biol. Chem. 277(33):29919-26; Ohta et al., 1984, J. Biol. Chem. 259(23):14888-93 and U.S. Pat. No. 6,372,886).

In certain embodiments, the methods and compositions of the present invention include the use of a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2): 703-6; Hoeg et al, 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2):328-38: Thurberg et al., J. Biol. Chem. 271(11):6062-70; Dyer 1991, J. Biol. Chem. 266(23): 150009-15; Hill 1998, J. Biol. Chem. 273(47):30979-84).

Apolipoproteins utilized in the invention also include recombinant, synthetic, semi-synthetic or purified apolipoproteins. Methods for obtaining apolipoproteins or equivalents thereof, utilized by the invention are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711:97-109; U.S. Pat. Nos. 5,059,528, 5,834, 596, 5,876,968 and 5,721,114; and PCT Publications WO 86/04920 and WO 87/02062).

Apolipoproteins utilized in the invention further include apolipoprotein agonists such as peptides and peptide analogues that mimic the activity of ApoA-I, ApoA-I Milano (ApoA-I$_M$), ApoA-I Paris (ApoA-I$_P$), ApoA-II, ApoA-IV, and ApoE. For example, the apolipoprotein can be any of those described in U.S. Pat. Nos. 6,004,925, 6,037,323, 6,046,166, and 5,840,688, the contents of which are incorporated herein by reference in their entireties.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046,166. For example, the peptides may be prepared using the solid-phase synthetic technique initially described by Merrifield (1963, J. Am. Chem. Soc. 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et. al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides of the present invention might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions of the invention will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotien can be obtained from an animal source. In certain embodiments, the apolipoprotein can be obtained from a human source. In preferred embodiments of the invention, the apolipoprotein is derived from the same species as the individual to which the apolipoprotein is administered.

In one embodiment the target gene is a gene expressed in the liver, e.g., the Factor VII (FVII) gene. In other embodiments, the target gene is expressed in the endothelium (e.g., in the heart, the liver, the lung, the kidney, the hypothalamus or the skeletal muscle). The effect of the expression of the target gene, e.g., FVII, is evaluated by measuring FVII levels in a biological sample, such as a serum or tissue sample. For example, the level of FVII, e.g., as measured by assay of FVII activity, in blood can be determined. In one embodiment, the level of mRNA in the liver or endothelium can be evaluated. In another preferred embodiment, at least two types of evaluation are made, e.g., an evaluation of protein level (e.g., in blood), and a measure of mRNA level (e.g., in the liver) are both made.

In one embodiment, the agent is a nucleic acid, such as a double-stranded RNA (dsRNA).

In another embodiment, the nucleic acid agent is a single-stranded DNA or RNA, or double-stranded DNA or RNA, or DNA-RNA hybrid. For example, a double-stranded DNA can be a structural gene, a gene including control and termination regions, or a self-replicating system such as a viral or plasmid DNA. A double-stranded RNA can be, e.g., a dsRNA or another RNA interference reagent. A single-stranded nucleic acid can be, e.g., an antisense oligonucleotide, ribozyme, microRNA, or triplex-forming oligonucleotide.

In yet another embodiment, at various time points after administration of a candidate agent, a biological sample, such as a fluid sample, e.g., blood, plasma, or serum, or a tissue sample, such as a liver or endothelium (e.g., from the heart, kidney, lung, hypothalamus or skeletal muscle) sample, is taken from the test subject and tested for an effect of the agent on target protein or mRNA expression levels. In one particularly preferred embodiment, the candidate agent is a dsRNA that targets FVII, and the biological sample is tested for an effect on Factor VII protein or mRNA levels. In one embodiment, plasma levels of FVII protein are assayed, such as by using an immunohistochemistry assay or a chromogenic assay. In another embodiment, levels of FVII mRNA in the liver or endothelium (e.g., in the heart, the liver, the lung, the kidney, the hypothalamus or the skeletal muscle) are tested by an assay, such as a branched DNA assay, or a Northern blot or RT-PCR assay.

In one embodiment, the agent, e.g., a composition including the lipid composition, is evaluated for toxicity. In yet another embodiment, the model subject can be monitored for physical effects, such as by a change in weight or cageside behavior.

In one embodiment, the method further includes subjecting the agent, e.g., a composition comprising the lipid composition, to a further evaluation. The further evaluation can include, for example, (i) a repetition of the evaluation described above, (ii) a repetition of the evaluation described above with a different number of animals or with different doses, or (iii) by a different method, e.g., evaluation in another animal model, e.g., a non-human primate.

In another embodiment, a decision is made regarding whether or not to include the agent and the lipid composition in further studies, such as in a clinical trial, depending on the observed effect of the candidate agent on liver protein or mRNA levels or the endothelium. For example, if a candidate dsRNA is observed to decrease protein or mRNA levels by at least 20%, 30%, 40%, 50%, or more, then the agent can be considered for a clinical trial.

In yet another embodiment, a decision is made regarding whether or not to include the agent and the lipid composition in a pharmaceutical composition, depending on the observed effect of the candidate agent and amino lipid on liver protein, mRNA levels or endothelium. For example, if a candidate dsRNA is observed to decrease protein or mRNA levels by at least 20%, 30%, 40%, 50%, or more, then the agent can be considered for a clinical trial.

In another aspect, the invention features a method of evaluating the lipid composition for its suitability for delivering an RNA-based construct, e.g., a dsRNA that targets FVII. The method includes providing a composition that includes a dsRNA that targets FVII and a candidate amino lipid, administering the composition to a rodent, e.g., a mouse, evaluating the expression of FVII as a function of at least one of the level of FVII in the blood or the level of FVII mRNA in the liver, thereby evaluating the candidate amino lipid.

Compositions that include lipid containing components, such as a liposome, and these are described in greater detail below. Exemplary nucleic acid-based agents include dsR- NAs, antisense oligonucleotides, ribozymes, microRNAs, immunostimulatory oligonucleotides, or triplex-forming oligonucleotides. These agents are also described in greater detail below.

Compositions referred to as "LNP" compositions (e.g., LNP01, LNP02, etc.) are also known as "AF" compositions (e.g., AF01, AF02, etc.).

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$-NR$^x$R$^y$.

"Halogen" means fluoro, chloro, bromo and iodo.

In some embodiments, the methods of the invention may require the use of protecting groups. Protecting group methodology is well known to those skilled in the art (see, for example, PROTECTIVE GROUPS IN ORGANIC SYNTHESIS, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis

The compounds of the invention may be prepared by known organic synthesis techniques. In general, lipid of formula (I), (II), (III), (IV) and (V) can be prepared by reacting the amine compound with various epoxides. In one example, the lipid of formula (V) and VI) can be made by the following Reaction Scheme 1, wherein all substituents are as defined above unless indicated otherwise.

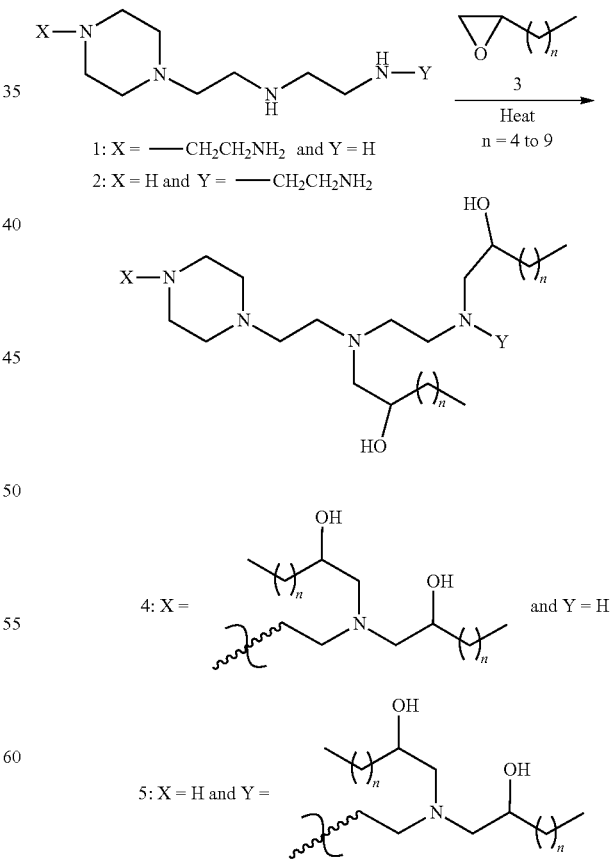

Compound 1 and 2 were synthesized according reported procedure described in WO/9318017.

Reaction of 1 with epoxide 3 at elevated temperature yielded compound 4, which was purified by standard silica gel column chromatography. Compound 5 was similarly obtained from the amine 2.

Other epoxides and amines suitable for forming amino lipids according to Scheme 1 are described in Love, K. T., et al., "Lipid-like materials for low-dose, in vivo gene silencing," PNAS Early Edition, www.pnas.org/cgi/doi/10.1073/pnas.0910603106, which is incorporated by reference in its entirety.

Some exemplary epoxides that may be used include:

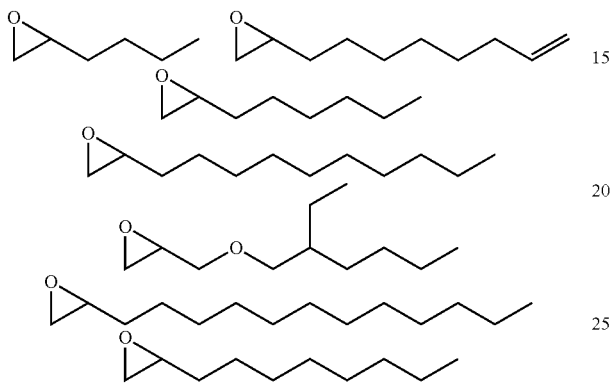

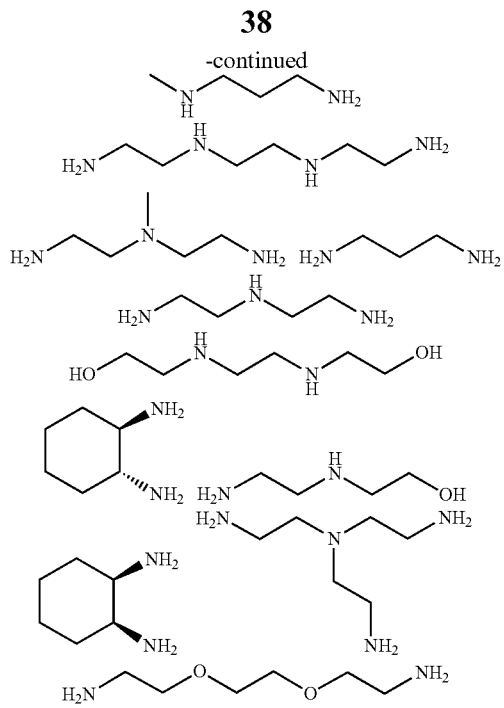

The compound of Formula (V),

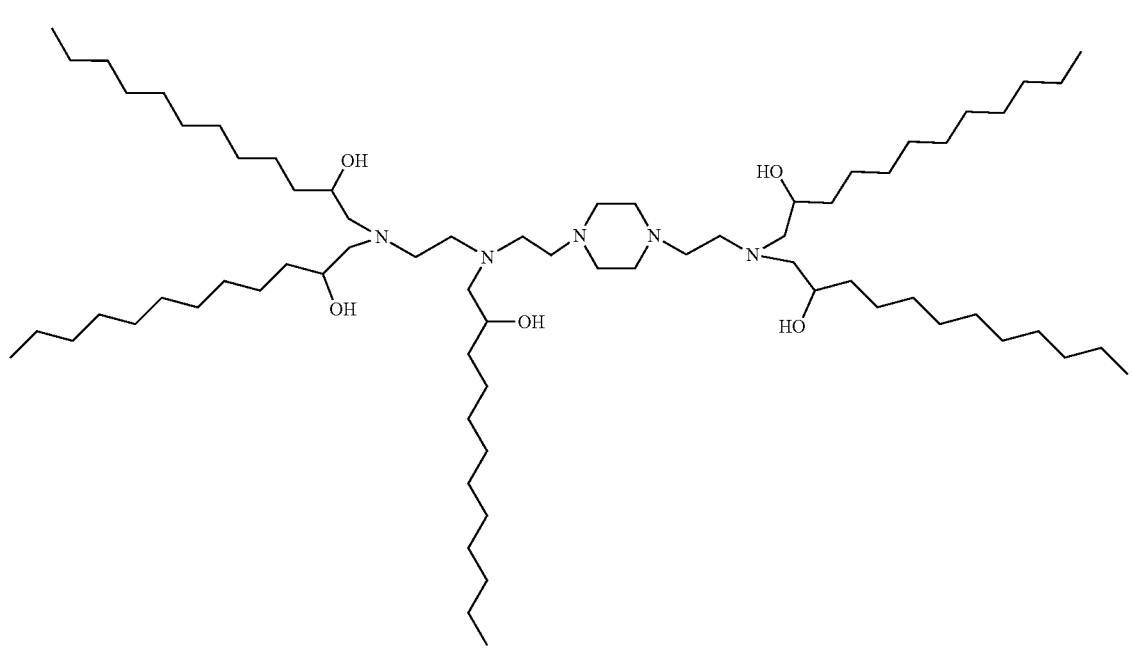

(V)

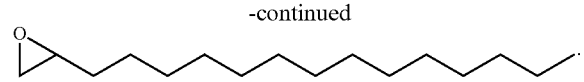

Some exemplary amines that may be used include:

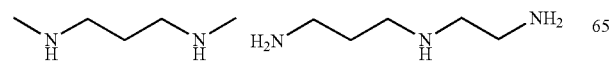

can be prepared from two precursors:

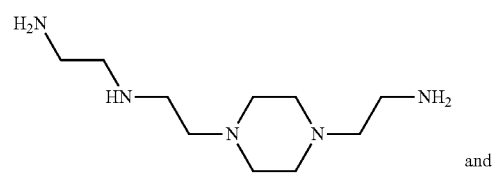

and

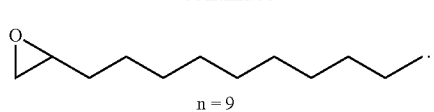

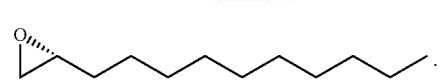

For example, the compound of formula (V) can be prepared from racemic 3. In this case, the initial product can include a mixture of diastereomers, which can optionally be further purified.

Compound (R)-6 is a stereocontrolled compound according to formula (V):

The corresponding (S)-6 compound can be prepared from 1 and (S)-7 (i.e., the enantiomer of (R)-7).

Structural isomers of 1 can also be used in the preparation of an amino lipid. Such structural isomers include.

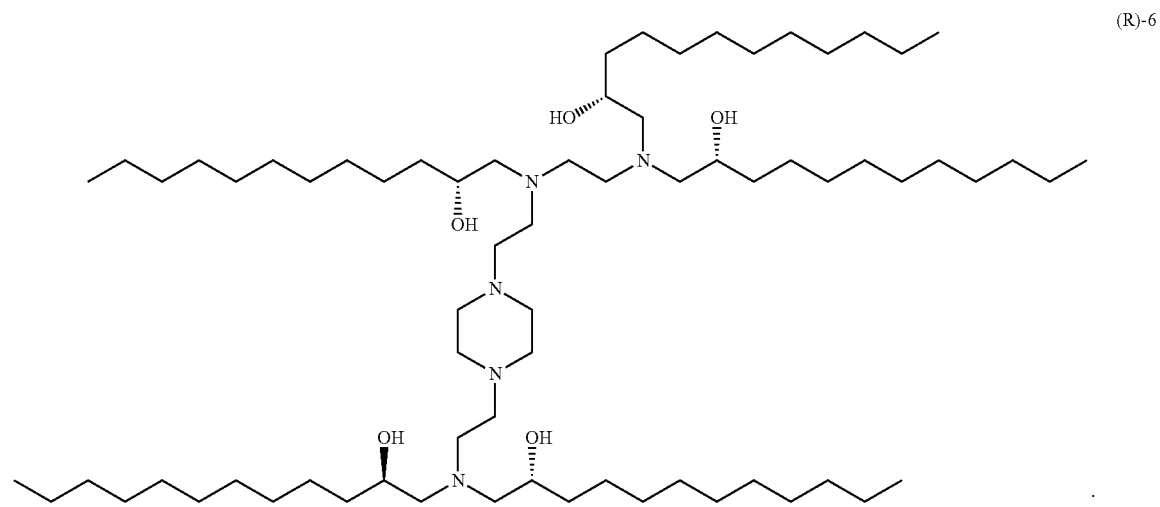 [SMILES: CCCCCCCCCC[C@@H](O)CN(CCN1CCN(CCN(C[C@H](O)CCCCCCCCCC)C[C@H](O)CCCCCCCCCC)CC1)CCN(C[C@H](O)CCCCCCCCCC)C[C@H](O)CCCCCCCCCC]

Compound (R)-6 can be prepared according to scheme 1 from two precursors:

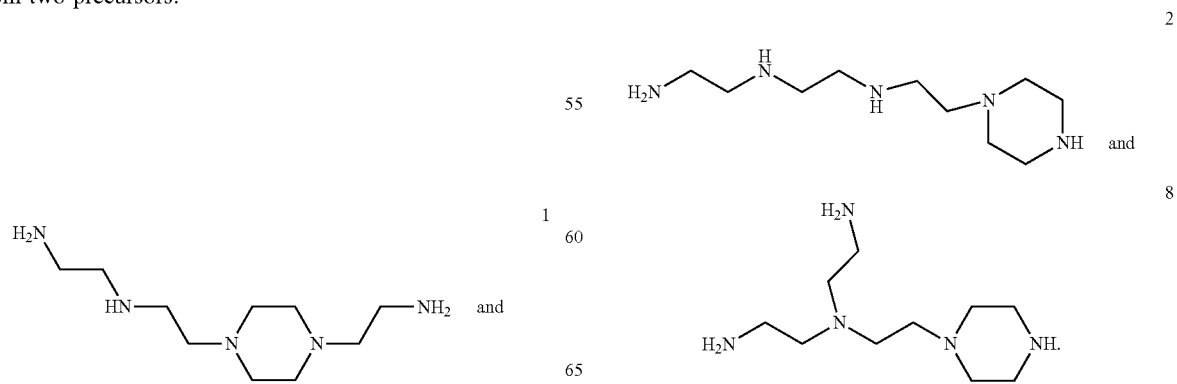

The compound of Formula (VI),
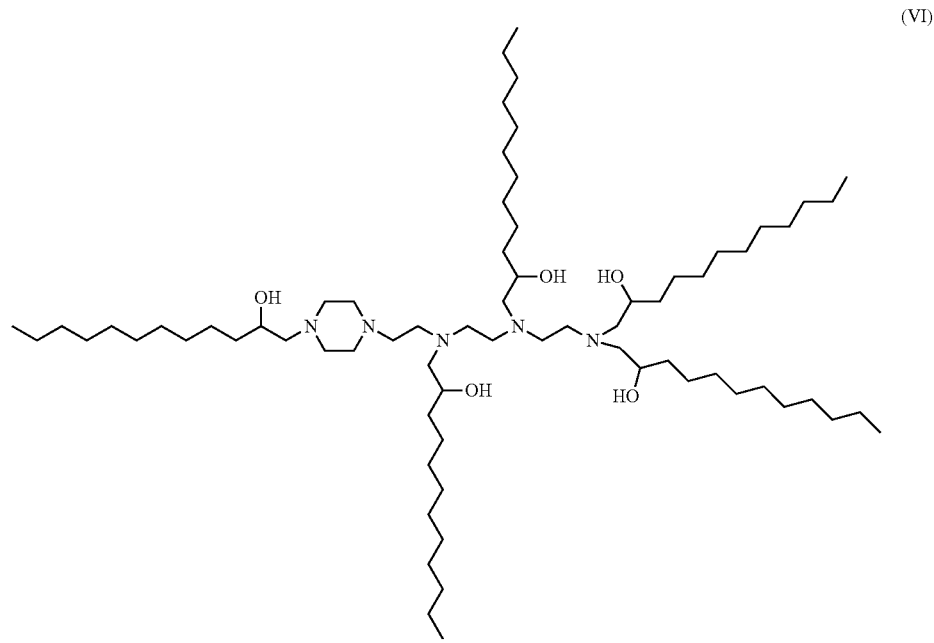 [SMILES: CCCCCCCCCCC(O)CN1CCN(CCN(CCN(CCN(CC(O)CCCCCCCCCC)CC(O)CCCCCCCCCC)CC(O)CCCCCCCCCC)CC(O)CCCCCCCCCC)CC1]
can be prepared from two precursors,
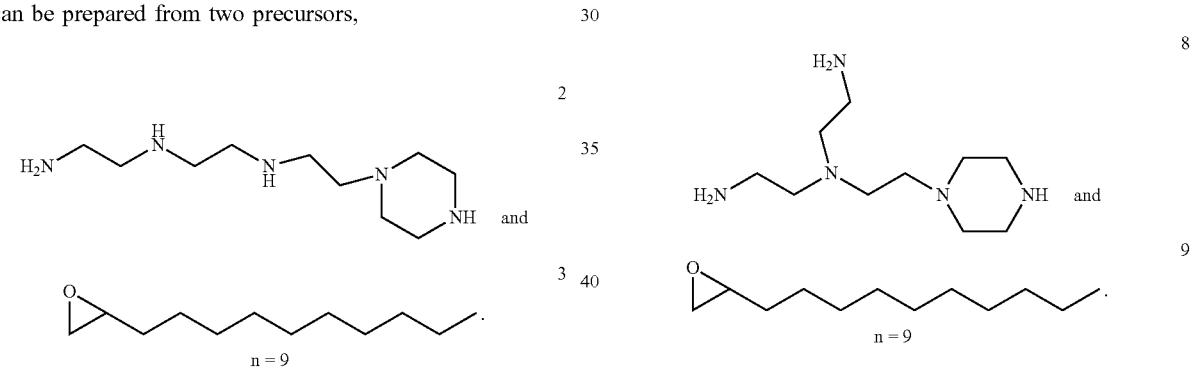
A substantially stereopure epoxide can be used to provide a stereocontrolled amino lipid.
The compound of Formula (VII),
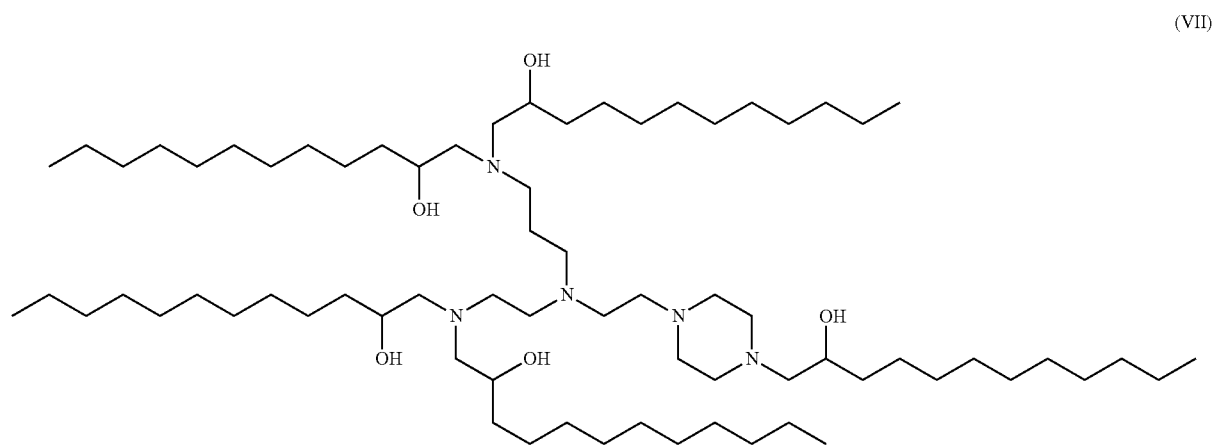 [SMILES: CCCCCCCCCCC(O)CN1CCN(CCN(CCCN(CC(O)CCCCCCCCCC)CC(O)CCCCCCCCCC)CCN(CC(O)CCCCCCCCCC)CC(O)CCCCCCCCCC)CC1]
can be prepared from two precursors, Scheme 2
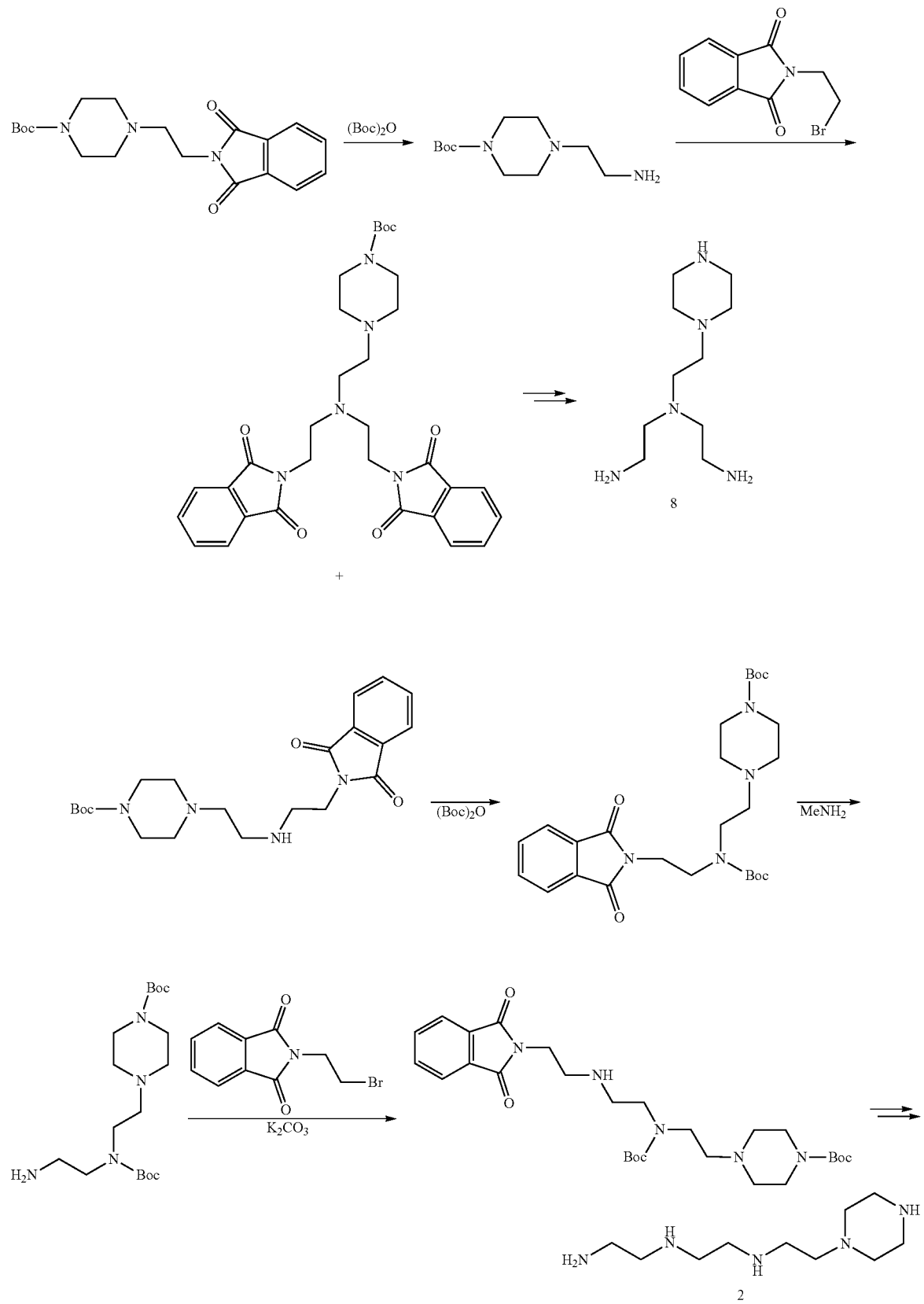

Amines 2 and 8 can be prepared according to Reaction Scheme 2. Both may be prepared from a common starting material, 4-(t-butoxycarbonyl)-1-(2-(phthalimido)ethyl)-piperazine.

Multigram quantities of 2 and 8 were prepared according to Scheme 2.

Amine 1 can be prepared according to Scheme 3, starting from 1-(2-amino ethyl)piperazine.

Scheme 3

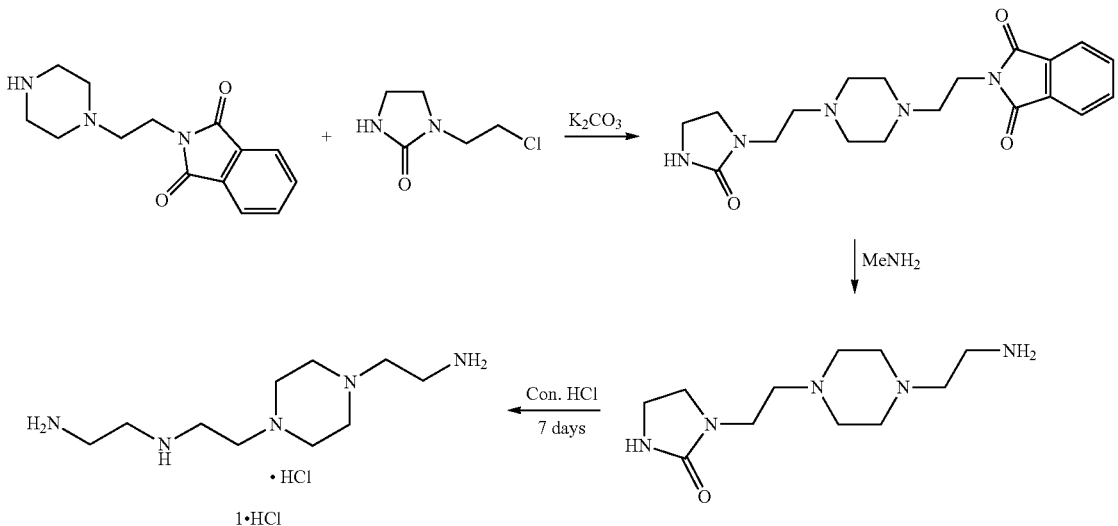

Alternatively, Scheme 4 illustrates preparation of 1 from 1-(2-(phthalimido)ethyl)piperazine:

Scheme 4

The method of Scheme 4 was scaled to produce 1 on the multigram scale. The final step can alternatively be performed with a base, such as KOH, instead of an acid, such as HCl. The reaction may proceed more rapidly under basic conditions.

In another variation, 1 can be prepared in a fashion similar to that shown in Scheme 3, but using different reducing conditions, as shown in Scheme 5.

Scheme 5

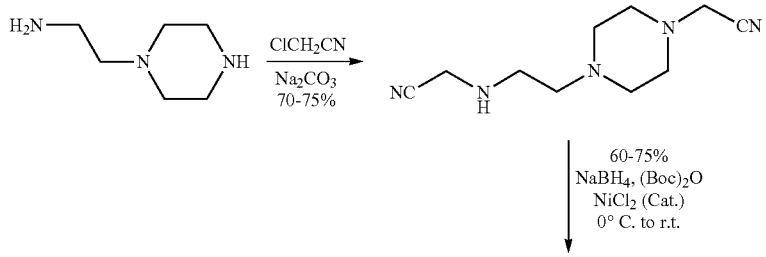

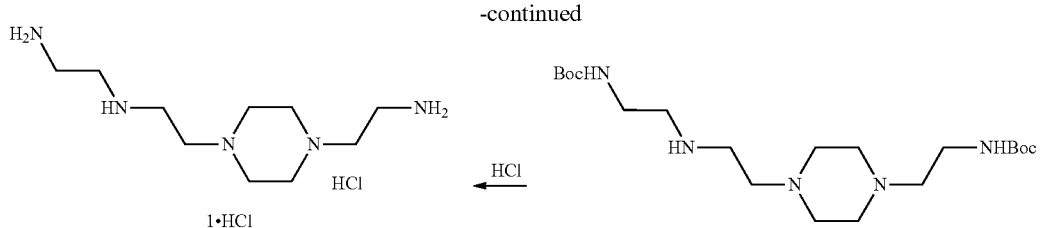

Advantageously, the method of Scheme 5 can be more easily scaled than the methods of Scheme 3 or Scheme 4; the reaction conditions are very mild, only a catalytic (10 mol %) amount of nickel(II)chloride is needed, and isolation and purification of the product are straightforward. This procedure was scaled to produce multigram quantities of 1.

Epoxide 3 (n=9) can be resolved to afford a desired optical isomer (e.g., (R)-7) in high enantiomeric excess. For example, 3 (n=9) can be resolved using a Jacobsen catalyst as illustrated in Scheme 6.

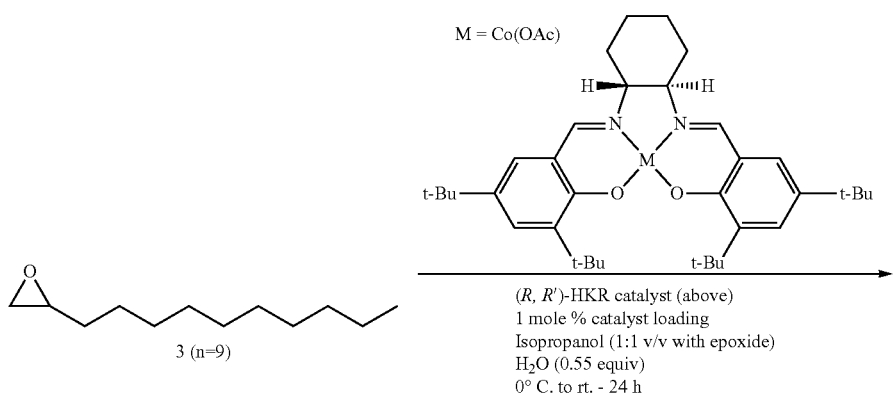

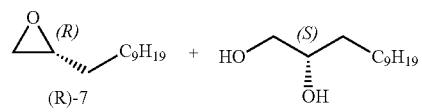

This reaction was carried out on a multigram (e.g., 300 g) scale.

Amino lipid (R)-6 was prepared from 1 and (R)-7 on a multigram (e.g., >16 g) scale. The reaction product was further purified by column chromatography; the resulting material was apparently pure when assayed by TLC. However, a number of minor products were also present. The minor products (see Scheme 7) arose from reactions in which the epoxide ring opening occurred on the more-hindered carbon, resulting in primary alcohols.

Scheme 7
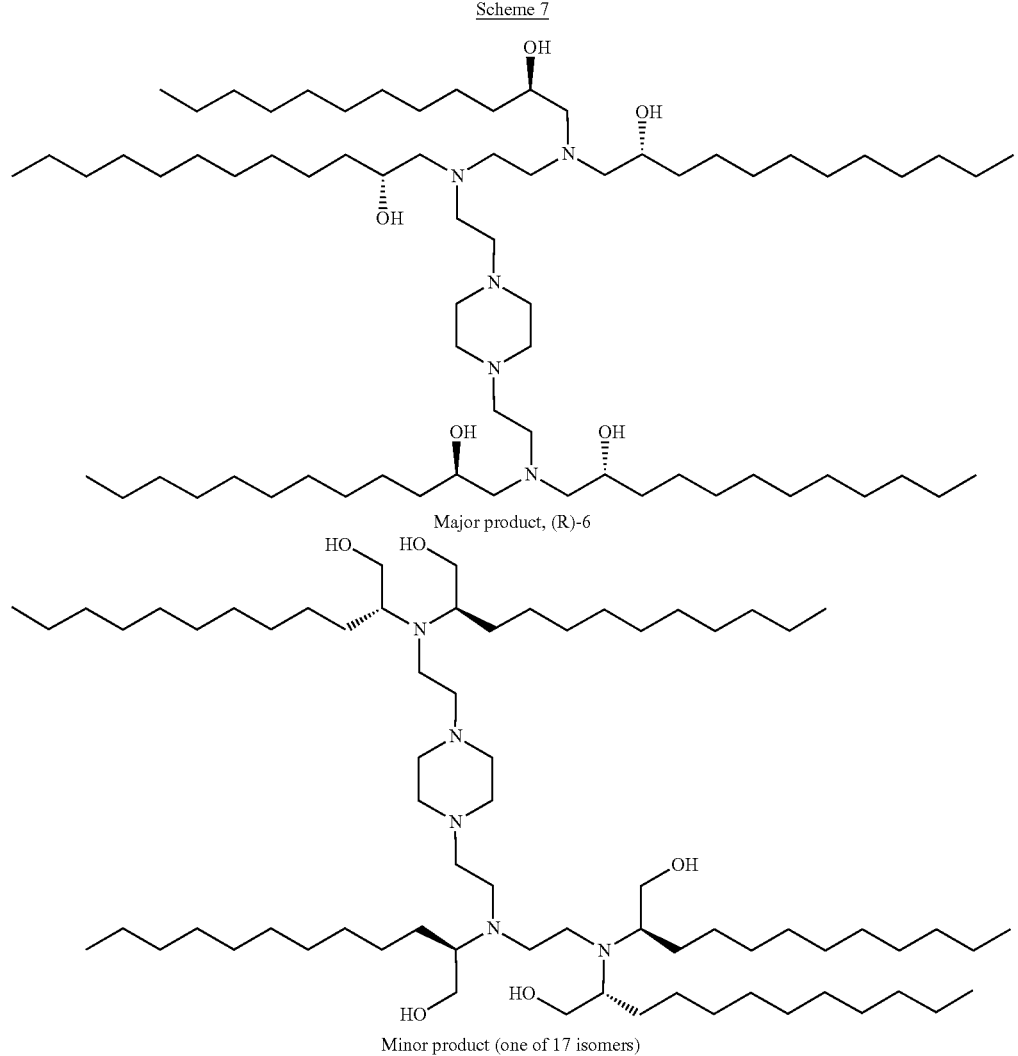
The minor products were substantially separated from the major product upon treatment with a solid-support trityl chloride reagent (Scheme 8), which reacted selectively with (and thus immobilized) primary alcohols.
Scheme 8
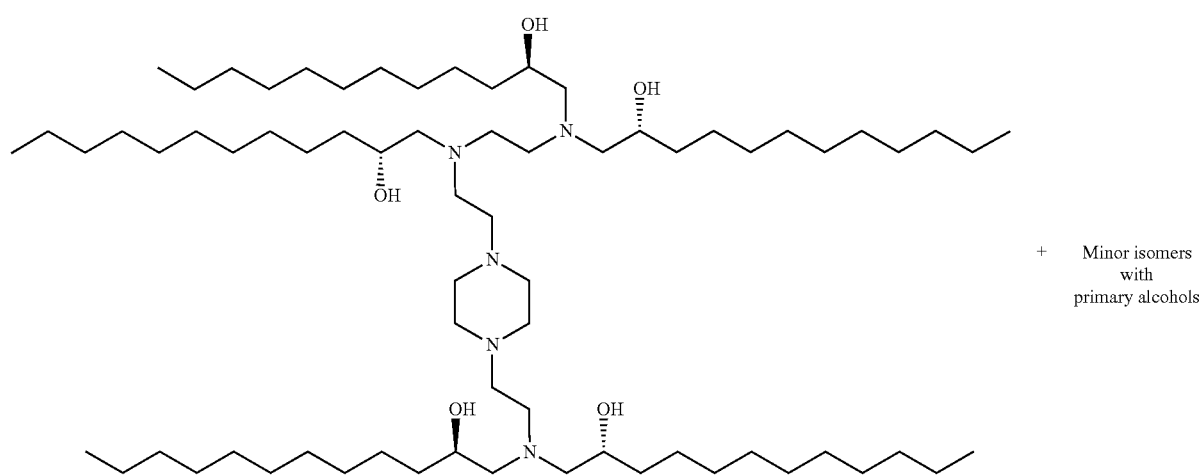
+ Minor isomers with primary alcohols

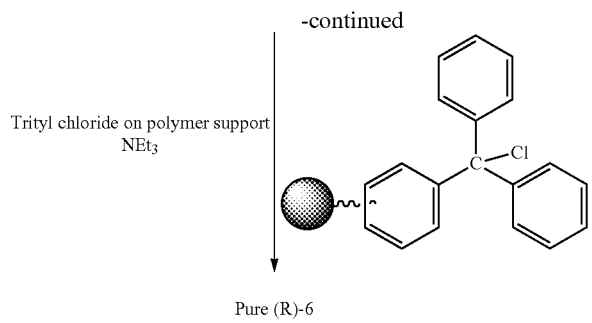

Another approach to stereocontrolled amino lipids can involve stereopure alpha-hydroxy aldehydes, which can be used in place of epoxides in the reaction with amines such as 1. When using the alpha-hydroxy aldehydes, the reaction with amines such as 1 takes place under reducing conditions. Scheme 9 illustrates a stereocontrolled synthesis of protected alpha-hydroxy aldehyde 10 starting from an alpha-olefin.

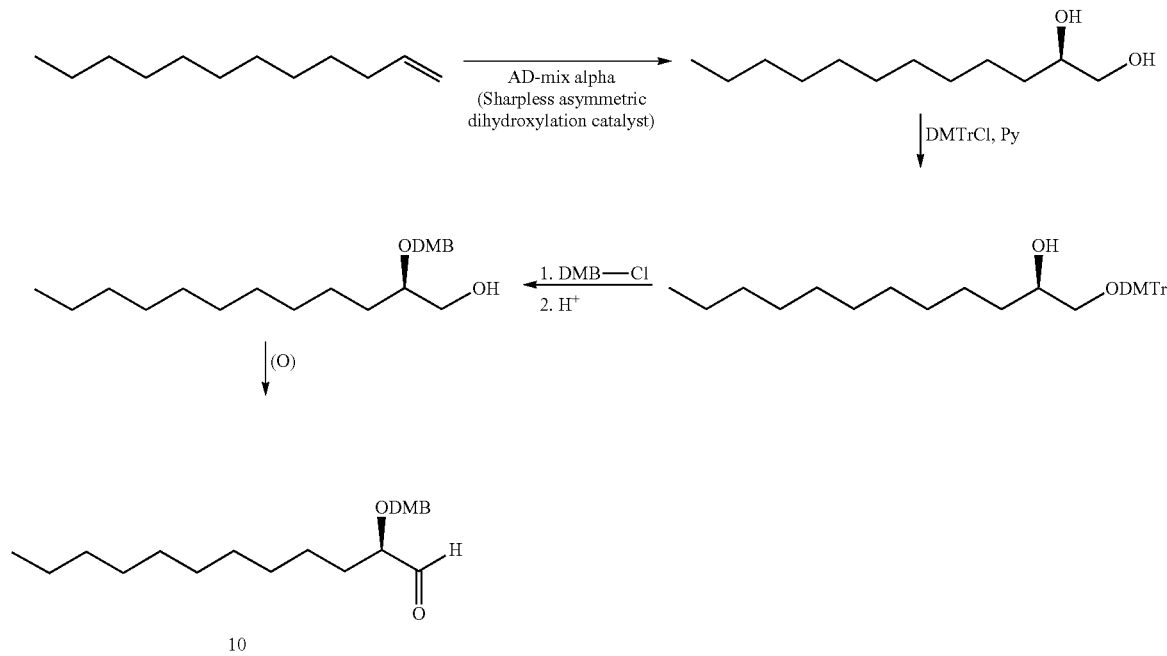

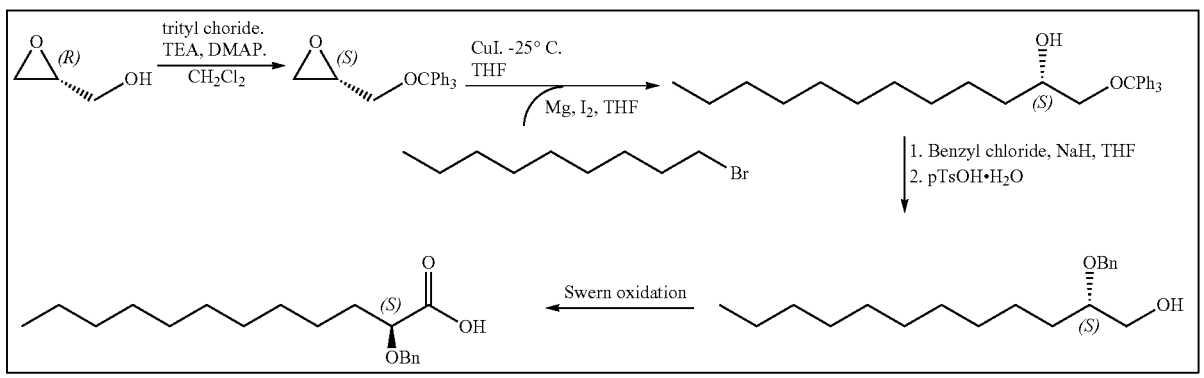

To produce stereocontrolled amino lipid such as (R)-6, amine 1 is allowed to react with a protected alpha-hydroxy aldehyde having the desired stereochemistry in the presence of a reducing agent, for example, Na(OAc)$_3$BH in AcOH.

The amino lipids are of the invention are cationic lipids. As used herein, the term "amino lipid" is meant to include those lipids having one or two fatty acid or fatty alkyl chains and an amino head group (including an alkylamino or dialkylamino group) that may be protonated to form a cationic lipid at physiological pH.

Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are preferred. Other scaffolds can also be used to separate the amino group and the fatty acid or fatty alkyl portion of the amino lipid. Suitable scaffolds are known to those of skill in the art.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain embodiments, protonatable lipids according to the invention have a pKa of the protonatable group in the range of about 4 to about 11. Most preferred is pKa of about 4 to about 7, because these lipids will be cationic at a lower pH formulation stage, while particles will be largely (though not completely) surface neutralized at physiological pH around pH 7.4. One of the benefits of this pKa is that at least some nucleic acid associated with the outside surface of the particle will lose its electrostatic interaction at physiological pH and be removed by simple dialysis; thus greatly reducing the particle's susceptibility to clearance.

Lipid Particles

The agents and/or amino lipids for testing in the liver or endothelium (e.g., in the heart, the liver, the lung, the kidney, the hypothalamus or the skeletal muscle) screening model featured herein can be formulated in lipid particles. Lipid particles include, but are not limited to, liposomes. As used herein, a liposome is a structure having lipid-containing membranes enclosing an aqueous interior. Liposomes may have one or more lipid membranes. The invention contemplates both single-layered liposomes, which are referred to as unilamellar, and multi-layered liposomes, which are referred to as multilamellar. When complexed with nucleic acids, lipid particles may also be lipoplexes, which are composed of cationic lipid bilayers sandwiched between DNA layers, as described, e.g., in Felgner, *Scientific American*.

Lipid particles may further include one or more additional lipids and/or other components such as cholesterol. Other lipids may be included in the liposome compositions for a variety of purposes, such as to prevent lipid oxidation or to attach ligands onto the liposome surface. Any of a number of lipids may be present, including amphipathic, neutral, cationic, and anionic lipids. Such lipids can be used alone or in combination. Specific examples of additional lipid components that may be present are described below.

Additional components that may be present in a lipid particle include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

A lipid particle can include one or more of a second amino lipid or cationic lipid, a neutral lipid, a sterol, and a lipid selected to reduce aggregation of lipid particles during formation, which may result from steric stabilization of particles which prevents charge-induced aggregation during formation.

Examples of lipids suitable for conjugation to nucleic acid agents that can be used in the liver or endothelium (e.g., heart, the liver, the lung, the kidney, the hypothalamus or the skeletal muscle) screening model are polyethylene glycol (PEG)-modified lipids, monosialoganglioside Gm1, and polyamide oligomers ("PAO") such as (described in U.S. Pat. No. 6,320,017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mePEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a T112 less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be preferable for the nucleic acid-lipid particle to exhibit a longer plasma circulation lifetime and hence the PEG-modified lipid will possess relatively longer lipid anchors. Exemplary lipid anchors include those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the invention are DOPE, DSPC, POPC, or any related phosphatidylcholine. The neutral lipids useful in the invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Other cationic lipids, which carry a net positive charge at about physiological pH, in addition to those specifically described above, may also be included in lipid particles of the invention. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), and N-(1, 2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

Anionic lipids suitable for use in lipid particles of the invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids are included in lipid particles of the invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the lipid particles of the invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. Exemplary lipid anchors include those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons.

By the time the lipid particle is suitably distributed in the body, it has lost sufficient cloaking agent so as to be fusogenic. With other signal events, it is desirable to choose a signal that is associated with the disease site or target cell, such as increased temperature at a site of inflammation.

A lipid particle conjugated to a nucleic acid agent can also include a targeting moiety, e.g., a targeting moiety that is specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can include the entire protein or fragments thereof. Targeting mechanisms generally require that the targeting agents be positioned on the surface of the lipid particle in such a manner that the targeting moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fl (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci. (USA)*, 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 Methods in Enzymology 111-119 (Academic Press, Inc. 1987)). Other targeting methods include the biotin-avidin system.

Therapeutic Agent-Lipid Particle Compositions and Formulations

The invention includes compositions comprising a lipid particle of the invention and an active agent, wherein the active agent is associated with the lipid particle. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free DNA. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, CA). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

Nucleic Acid-Lipid Particles

In certain embodiments, lipid particles of the invention are associated with a nucleic acid, resulting in a nucleic acid-lipid particle. In particular embodiments, the nucleic acid is fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucletoides of the invention are 20-50 nucleotides in length.

In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides.

Nucleic acids of the invention may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, both single-stranded, double-stranded, and triple-stranded, may range in length from about 10 to about 50 nucleotides, from about 20 o about 50 nucleotides, from about 15 to about 30 nucleotides, from about 20 to about 30 nucleotides in length.

In particular embodiments, an oligonucleotide (or a strand thereof) of the invention specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions as compared to the region of a gene or mRNA sequence that it is targeting or to which it specifically hybridizes.

RNA Interference Nucleic Acids

In particular embodiments, nucleic acid-lipid particles of the invention are associated with RNA interference (RNAi) molecules. RNA interference methods using RNAi molecules may be used to disrupt the expression of a gene or polynucleotide of interest. In the last 5 years small interfering RNA (siRNA) has essentially replaced antisense ODN and ribozymes as the next generation of targeted oligonucleotide drugs under development. SiRNAs are RNA duplexes normally 21-30 nucleotides long that can associate with a cytoplasmic multi-protein complex known as RNAi-induced silencing complex (RISC). RISC loaded with siRNA mediates the degradation of homologous mRNA transcripts, therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., Nature Reviews 6:443-453 (2007).

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S. and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded polynucleotides comprising two separate strands, i.e. a sense strand and an antisense strand, e.g., small interfering RNA (siRNA); polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

RNA interference (RNAi) may be used to specifically inhibit expression of target polynucleotides. Double-stranded RNA-mediated suppression of gene and nucleic acid expression may be accomplished according to the invention by introducing dsRNA, siRNA or shRNA into cells or organisms. SiRNA may be double-stranded RNA, or a hybrid molecule comprising both RNA and DNA, e.g., one RNA strand and one DNA strand. It has been demonstrated that the direct introduction of siRNAs to a cell can trigger RNAi in mammalian cells (Elshabir, S. M., et al. Nature 411:494-498 (2001)). Furthermore, suppression in mammalian cells occurred at the RNA level and was specific for the targeted genes, with a strong correlation between RNA and protein suppression (Caplen, N. et al., Proc. Natl. Acad. Sci. USA 98:9746-9747 (2001)). In addition, it was shown that a wide variety of cell lines, including HeLa S3, COS7, 293, NIH/3T3, A549, HT-29, CHO—KI and MCF-7 cells, are susceptible to some level of siRNA silencing (Brown, D. et al. TechNotes 9(1):1-7, available on the worldwide web at www.dot.ambion.dot.com/techlib/tn/91/912.html (9/1/02)).

RNAi molecules targeting specific polynucleotides can be readily prepared according to procedures known in the art. Structural characteristics of effective siRNA molecules have been identified. Elshabir, S. M. et al. (2001) Nature 411: 494-498 and Elshabir, S. M. et al. (2001), EMBO 20:6877-6888. Accordingly, one of skill in the art would understand that a wide variety of different siRNA molecules may be used to target a specific gene or transcript. In certain embodiments, siRNA molecules according to the invention are double-stranded and 16-30 or 18-25 nucleotides in length, including each integer in between. In one embodiment, an siRNA is 21 nucleotides in length. In certain embodiments, siRNAs have 0-7 nucleotide 3' overhangs or 0-4 nucleotide 5' overhangs. In one embodiment, an siRNA molecule has a two nucleotide 3' overhang. In one embodiment, an siRNA is 21 nucleotides in length with two nucleotide 3' overhangs (i.e. they contain a 19 nucleotide complementary region between the sense and antisense strands). In certain embodiments, the overhangs are UU or dTdT 3' overhangs.

Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications. However, in preferred embodiments, the entire strand of the siRNA is not made with either 2' deoxy or 2'-O-modified bases.

In another embodiment, the invention provides a cell including a vector for inhibiting the expression of a gene in a cell. The vector includes a regulatory sequence operably linked to a nucleotide sequence that encodes at least one strand of one of the dsRNA of the invention.

In one embodiment, siRNA target sites are selected by scanning the target mRNA transcript sequence for the occurrence of AA dinucleotide sequences. Each AA dinucleotide sequence in combination with the 3' adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir, S. et al. Nature 411:494-498 (2001); Elshabir, S. et al. EMBO J. 20:6877-6888 (2001)). In addition, potential target sites may be compared to an appropriate genome database, such as BLASTN 2.0.5, available on the NCBI server at www.ncbi.nlm, and potential target sequences with significant homology to other coding sequences eliminated.

In particular embodiments, short hairpin RNAs constitute the nucleic acid component of nucleic acid-lipid particles of the invention. Short Hairpin RNA (shRNA) is a form of hairpin RNA capable of sequence-specifically reducing expression of a target gene. Short hairpin RNAs may offer an advantage over siRNAs in suppressing gene expression, as they are generally more stable and less susceptible to degradation in the cellular environment. It has been established that such short hairpin RNA-mediated gene silencing works in a variety of normal and cancer cell lines, and in mammalian cells, including mouse and human cells. Paddison, P. et al., Genes Dev. 16(8):948-58 (2002). Furthermore, transgenic cell lines bearing chromosomal genes that code for engineered shRNAs have been generated. These cells are able to constitutively synthesize shRNAs, thereby facilitating long-lasting or constitutive gene silencing that may be passed on to progeny cells. Paddison, P. et al., Proc. Natl. Acad. Sci. USA 99(3):1443-1448 (2002).

ShRNAs contain a stem loop structure. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. ShRNA molecules may contain mismatches, for example G-U mismatches between the two strands of the shRNA stem without decreasing potency. In fact, in certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, since they do not appear to be critical for shRNA function, although they may be present (Paddison et al. (2002) Genes & Dev. 16(8):948-58).

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs.RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also on the worldwide web at microrna.dot.sanger.dot.ac.dot.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence. In the case of antisense RNA, they prevent translation of complementary RNA strands by binding to it. Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal GABA A receptor and human EGF (Jaskulski et al., Science. 1988 Jun. 10; 240(4858):1544-6; Vasanthakumar and Ahmed, Cancer Commun. 1989; 1(4):225-32; Penis et al., Brain Res Mol Brain Res. 1998 Jun. 15; 57(2):310-20; U.S. Pat. Nos. 5,801,154; 5,789,573; 5,718,709 and 5,610,288). Furthermore, antisense constructs have also been described that inhibit and can be used to treat a variety of abnormal cellular proliferations, e.g. cancer (U.S. Pat. Nos. 5,747,470; 5,591,317 and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, T m, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Ribozymes

According to another embodiment of the invention, nucleic acid-lipid particles are associated with ribozymes. Ribozymes are RNA-protein complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or Neurospora VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Additional specific nucleic acid sequences of oligonucleotides (ODNs) suitable for use in the compositions and methods of the invention are described in U.S. Patent Appln. 60/379,343, U.S. patent application Ser. No. 09/649,527, Int. Publ. WO 02/069369, Int. Publ. No. WO 01/15726, U.S. Pat. No. 6,406,705, and Raney et al., Journal of Pharmacology and Experimental Therapeutics, 298:1185-1192 (2001). In certain embodiments, ODNs used in the compositions and methods of the invention have a phosphodiester ("PO")

backbone or a phosphorothioate ("PS") backbone, and/or at least one methylated cytosine residue in a CpG motif.

Nucleic Acid Modifications

In the 1990's DNA-based antisense oligodeoxynucleotides (ODN) and ribozymes (RNA) represented an exciting new paradigm for drug design and development, but their application in vivo was prevented by endo- and exo-nuclease activity as well as a lack of successful intracellular delivery. The degradation issue was effectively overcome following extensive research into chemical modifications that prevented the oligonucleotide (oligo) drugs from being recognized by nuclease enzymes but did not inhibit their mechanism of action. This research was so successful that antisense ODN drugs in development today remain intact in vivo for days compared to minutes for unmodified molecules (Kurreck, J. 2003. Antisense technologies. Improvement through novel chemical modifications. Eur J Biochem 270:1628-44). However, intracellular delivery and mechanism of action issues have so far limited antisense ODN and ribozymes from becoming clinical products.

RNA duplexes are inherently more stable to nucleases than single stranded DNA or RNA, and unlike antisense ODN, unmodified siRNA show good activity once they access the cytoplasm. Even so, the chemical modifications developed to stabilize antisense ODN and ribozymes have also been systematically applied to siRNA to determine how much chemical modification can be tolerated and if pharmacokinetic and pharmacodynamic activity can be enhanced. RNA interference by siRNA duplexes requires an antisense and sense strand, which have different functions. Both are necessary to enable the siRNA to enter RISC, but once loaded the two strands separate and the sense strand is degraded whereas the antisense strand remains to guide RISC to the target mRNA. Entry into RISC is a process that is structurally less stringent than the recognition and cleavage of the target mRNA. Consequently, many different chemical modifications of the sense strand are possible, but only limited changes are tolerated by the antisense strand (Zhang et al., 2006).

As is known in the art, a nucleoside is a base-sugar combination. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

The nucleic acid that is used in a lipid-nucleic acid particle according to this invention includes any form of nucleic acid that is known. Thus, the nucleic acid may be a modified nucleic acid of the type used previously to enhance nuclease resistance and serum stability. Surprisingly, however, acceptable therapeutic products can also be prepared using the method of the invention to formulate lipid-nucleic acid particles from nucleic acids that have no modification to the phosphodiester linkages of natural nucleic acid polymers, and the use of unmodified phosphodiester nucleic acids (i.e., nucleic acids in which all of the linkages are phosphodiester linkages) is a preferred embodiment of the invention.

Backbone Modifications

Antisense, siRNA and other oligonucleotides useful in this invention include, but are not limited to, oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphoroselenate, methylphosphonate, or O-alkyl phosphotriester linkages, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Particular non-limiting examples of particular nucleic acid modifications that may be present in a nucleic acid according to the invention are shown in Table 2.

Various salts, mixed salts and free acid forms are also included. Representative United States patents that teach the preparation of the above linkages include, but are not limited to, U.S. Pat. Nos. 3,687,808; 4,469,863; 4,476,301; 5,177,196; 5,188,897; 5,264,423; 5,276,019; 5,278,302; 5,286,717; 5,399,676; 5,405,939; 5,453,496; 5,455,233; 5,466,677; 5,476,925; 5,536,821; 5,541,306; 5,550,111; 5,563,253; 5,571,799; 5,587,361; and In certain embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, e.g., those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that describe the above oligonucleosides include, but are not limited to, U.S. Pat. Nos. 5,034,506; 5,166,315; 5,214,134; 5,216,141; 5,235,033; 5,264,562; 5,264,564; 5,405,938; 5,466,677; 5,470,967; 5,489,677; 5,541,307; 5,561,225; 5,596,086; 5,610,289; 5,602,240; 5,608,046; 5,610,289; 5,618,704; 5,623,070; 5,633,360; 5,677,437; and 5,677,439.

The phosphorothioate backbone modification (Table 3, #1), where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, J., *Eur. J. Biochem.* 270:1628-44, 2003). However, PS oligos are known to avidly associate non-specifically with proteins resulting in toxicity, especially upon i.v. administration. Therefore, the PS modification is usually restricted to one or two bases at the 3' and ends. The boranophosphate linker (Table 3, #2) is a recent modification that is apparently more stable than PS, enhances siRNA activity and has low toxicity (Hall et al., Nucleic Acids Res. 32:5991-6000, 2004).

TABLE 3
Chemical Modifications Applied to siRNA and Other Nucleic Acids
| # | Abbreviation | Name | Modification Site | Structure |
|---|---|---|---|---|
| 1 | PS | Phosphorothioate | Backbone | 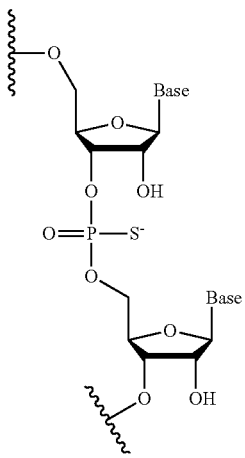 |
| 2 | PB | Boranophosphate | Backbone | 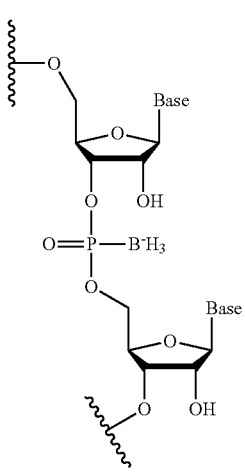 |
| 3 | N3-MU | N3-methyl-uridine | Base | 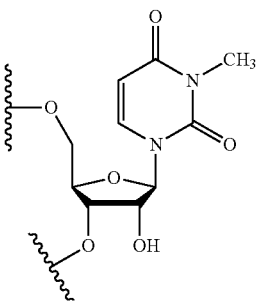 |
| 4 | 5'-BU | 5'-bromo-uracil | Base | 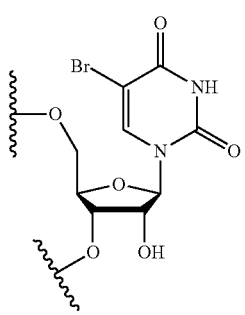 |

TABLE 3-continued
Chemical Modifications Applied to siRNA and Other Nucleic Acids
| # | Abbreviation | Name | Modification Site | Structure |
|---|---|---|---|---|
| 5 | 5'-IU | 5'-iodo-uracil | Base | 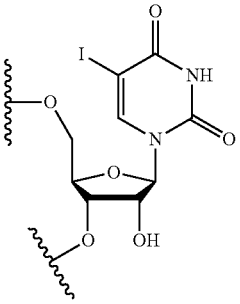 |
| 6 | 2,6-DP | 2,6-diaminopurine | Base | 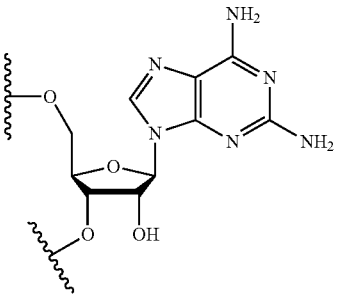 |
| 7 | 2'-F | 2'-Fluoro | Sugar | 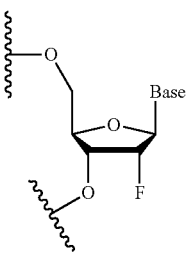 |
| 8 | 2'-OME | 2''-O-methyl | Sugar | 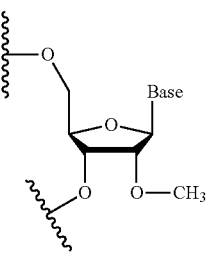 |
| 9 | 2'-O—MOE | 2'-O-(2-methoxylethyl) | Sugar | 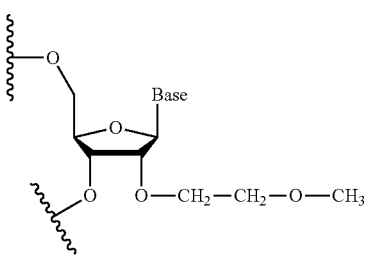 |

TABLE 3-continued

Chemical Modifications Applied to siRNA and Other Nucleic Acids

| # | Abbreviation | Name | Modification Site | Structure |
|---|---|---|---|---|
| 10 | 2'-DNP | 2'-O-(2,4-dinitrophenyl) | Sugar | 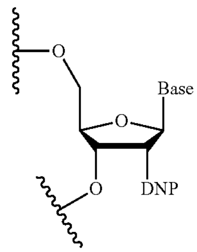 |
| 11 | LNA | Locked Nucleic Acid (methylene bridge connecting the 2'-oxygen with the 4'-carbon of the ribose ring) | Sugar | 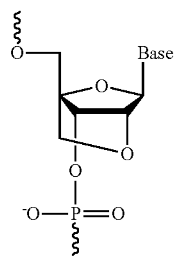 |
| 12 | 2'-Amino | 2'-Amino | Sugar | 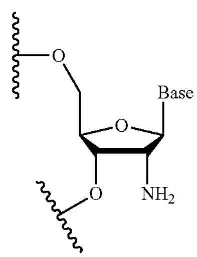 |
| 13 | 2'-Deoxy | 2'-Deoxy | Sugar | 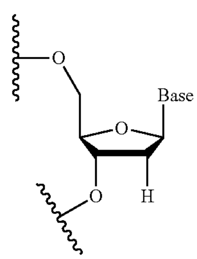 |
| 14 | 4'-thio | 4'-thio-ribonucleotide | Sugar | 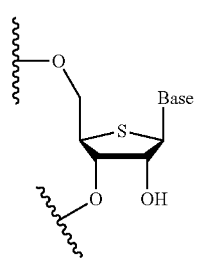 |

Other useful nucleic acids derivatives include those nucleic acids molecules in which the bridging oxygen atoms (those forming the phosphoester linkages) have been replaced with —S—, —NH—, —CH2— and the like. In certain embodiments, the alterations to the antisense, siRNA, or other nucleic acids used will not completely affect the negative charges associated with the nucleic acids. Thus, the invention contemplates the use of antisense, siRNA, and other nucleic acids in which a portion of the linkages are replaced with, for example, the neutral methyl phosphonate or phosphoramidate linkages. When neutral linkages are used, in certain embodiments, less than 80% of the nucleic acid linkages are so substituted, or less than 50% of the linkages are so substituted.

Base Modifications

Base modifications are less common than those to the backbone and sugar. The modifications shown in 0.3-6 all appear to stabilize siRNA against nucleases and have little effect on activity (Zhang, H. Y., Du, Q., Wahlestedt, C., Liang, Z. 2006. RNA Interference with chemically modified siRNA. *Curr Top Med Chem* 6:893-900).

Accordingly, oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Certain nucleobases are particularly useful for increasing the binding affinity of the oligomeric compounds of the invention, including 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications* 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. No. 3,687,808, as well as U.S. Pat. Nos. 4,845,205; 5,130,302; 5,175,273; 5,367,066; 5,432,272; 5,457,187; 5,459,255; 5,484,908; 5,525,711; 5,552,540; 5,587,469; 5,594,121, 5,596,091; 5,614,617; and Sugar Modifications Most modifications on the sugar group occur at the 2'-OH of the RNA sugar ring, which provides a convenient chemically reactive site (Manoharan, M. 2004. RNA interference and chemically modified small interfering RNAs. *Curr Opin Chem Biol* 8:570-9; Zhang, H. Y., Du, Q., Wahlestedt, C., Liang, Z. 2006. RNA Interference with chemically modified siRNA. *Curr Top Med Chem* 6:893-900). The 2'-F and 2'-OME (0.7 and 8) are common and both increase stability, the 2'-OME modification does not reduce activity as long as it is restricted to less than 4 nucleotides per strand (Holen, T., Amarzguioui, M., Babaie, E., Prydz, H. 2003. Similar behaviour of single-strand and double-strand siRNAs suggests they act through a common RNAi pathway. *Nucleic Acids Res* 31:2401-7). The 2'-O-MOE (0.9) is most effective in siRNA when modified bases are restricted to the middle region of the molecule (Prakash, T. P., Allerson, C. R., Dande, P., Vickers, T. A., Sioufi, N., Jarres, R., Baker, B. F., Swayze, E. E., Griffey, R. H., Bhat, B. 2005. Positional effect of chemical modifications on short interference RNA activity in mammalian cells. *J Med Chem* 48:4247-53). Other modifications found to stabilize siRNA without loss of activity are shown in 0.10-14.

Modified oligonucleotides may also contain one or more substituted sugar moieties. For example, the invention includes oligonucleotides that comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $No_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486-504), i.e., an alkoxyalkoxy group. Other modifications include 2'-dimethylaminooxyethoxy, i.e., a $O(CH_2)_2ON(CH_3)_2$ group, also known as 2'-DMAOE, and 2'-dimethyl-aminoethoxyethoxy (2'-DMAEOE).

Additional modifications include 2'-methoxy (2'-O—$CH_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach preparation of such modified sugars structures include, but are not limited to, U.S. Pat. Nos. 4,981,957; 5,118,800; 5,319,080; 5,359,044; 5,446,137; 5,466,786; 5,514,785; 5,519,134; 5,567,811; 5,576,427; 5,597,909; 5,610,300; 5,627,053; 5,639,873; 5,646,265; 5,658,873; and 5,700,920.

In other oligonucleotide mimetics, both the sugar and the internucleoside linkage, i.e., the backbone, of the nucleotide units are replaced with novel groups, although the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719, 262. Further teaching of PNA compounds can be found in Nielsen et al. (Science, 1991, 254, 1497-1500).

Particular embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— (referred to as a methylene (methylimino) or MMI backbone) —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester backbone is represented as —O—P—O—CH$_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Chimeric Oligonucleotides

It is not necessary for all positions in a given compound to be uniformly modified, and in fact more than one of the aforementioned modifications may be incorporated in a single compound or even at a single nucleoside within an oligonucleotide. Certain preferred oligonucleotides of this invention are chimeric oligonucleotides. "Chimeric oligonucleotides" or "chimeras," in the context of this invention, are oligonucleotides that contain two or more chemically distinct regions, each made up of at least one nucleotide. These oligonucleotides typically contain at least one region of modified nucleotides that confers one or more beneficial properties (such as, e,g., increased nuclease resistance, increased uptake into cells, increased binding affinity for the RNA target) and a region that is a substrate for RNase H cleavage.

In one embodiment, a chimeric oligonucleotide comprises at least one region modified to increase target binding affinity. Affinity of an oligonucleotide for its target is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In one embodiment, the region of the oligonucleotide which is modified to increase target mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance oligonucleotide inhibition of target gene expression.

In another embodiment, a chimeric oligonucletoide comprises a region that acts as a substrate for RNAse H. Of course, it is understood that oligonucleotides may include any combination of the various modifications described herein Another modification of the oligonucleotides of the invention involves chemically linking to the oligonucleotide one or more moieties or conjugates which enhance the activity, cellular distribution or cellular uptake of the oligonucleotide. Such conjugates and methods of preparing the same are known in the art.

Those skilled in the art will realize that for in vivo utility, such as therapeutic efficacy, a reasonable rule of thumb is that if a thioated version of the sequence works in the free form, that encapsulated particles of the same sequence, of any chemistry, will also be efficacious. Encapsulated particles may also have a broader range of in vivo utilities, showing efficacy in conditions and models not known to be otherwise responsive to antisense therapy. Those skilled in the art know that applying this invention they may find old models which now respond to antisense therapy. Further, they may revisit discarded antisense sequences or chemistries and find efficacy by employing the invention.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide including a nucleotide bearing such replacement moiety. For example, without limitation, a nucleotide including inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences including such replacement moieties are embodiments of the invention.

By "Factor VII" as used herein is meant a Factor VII mRNA, protein, peptide, or polypeptide. The term "Factor VII" is also known in the art as AI132620, Cf7, Coagulation factor VII precursor, coagulation factor VII, FVII, Serum prothrombin conversion accelerator, FVII coagulation protein, and eptacog alfa.

As used herein, "target sequence" refers to a contiguous portion of the nucleotide sequence of an mRNA molecule formed during the transcription of the gene, including mRNA that is a product of RNA processing of a primary transcription product.

As used herein, the term "strand including a sequence" refers to an oligonucleotide including a chain of nucleotides that is described by the sequence referred to using the standard nucleotide nomenclature.

As used herein, and unless otherwise indicated, the term "complementary," when used in the context of a nucleotide pair, means a classic Watson-Crick pair, i.e., GC, AT, or AU. It also extends to classic Watson-Crick pairings where one or both of the nuclotides has been modified as described herein, e.g., by a ribose modification or a phosphate backbone modification. It can also include pairing with an inosine or other entity that does not substantially alter the base pairing properties.

As used herein, and unless otherwise indicated, the term "complementary," when used to describe a first nucleotide sequence in relation to a second nucleotide sequence, refers to the ability of an oligonucleotide or polynucleotide including the first nucleotide sequence to hybridize and form a duplex structure under certain conditions with an oligonucleotide or polynucleotide including the second nucleotide sequence, as will be understood by the skilled person. Complementarity can include, full complementarity, substantial complementarity, and sufficient complementarity to allow hybridization under physiological conditions, e.g, under physiologically relevant conditions as may be encountered inside an organism. Full complementarity refers to complementarity, as defined above for an individual pair, at all of the pairs of the first and second sequence. When a sequence is "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. Substantial complementarity can also be defined as hybridization under stringent conditions, where stringent conditions may include: 400 mM NaCl, 40 mM PIPES pH 6.4, 1 mM EDTA, 50° C. or 70° C. for 12-16 hours followed by washing. The skilled person will be able to determine the set of conditions most appropriate for a test of complementarity of two sequences in accordance with the ultimate application of the hybridized nucleotides.

However, where two oligonucleotides are designed to form, upon hybridization, one or more single stranded overhangs, such overhangs shall not be regarded as mismatches with regard to the determination of complementarity. For example, a dsRNA including one oligonucleotide 21 nucleotides in length and another oligonucleotide 23 nucleotides in length, wherein the longer oligonucleotide includes a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary", "substantially complementary" and sufficient complementarity to allow hybridization under physiological conditions, e.g, under physiologically relevant conditions as may be encountered inside an organism, may be used herein with respect to the base matching between the sense strand and the antisense strand of a dsRNA, or between the antisense strand of a dsRNA and a target sequence, as will be understood from the context of their use.

As used herein, a polynucleotide which is "complementary, e.g., substantially complementary to at least part of" a messenger RNA (mRNA) refers to a polynucleotide which is complementary, e.g., substantially complementary, to a contiguous portion of the mRNA of interest (e.g., encoding Factor VII). For example, a polynucleotide is complementary to at least a part of a Factor VII mRNA if the sequence is substantially complementary to a non-interrupted portion of an mRNA encoding Factor VII.

The term "double-stranded RNA" or "dsRNA", as used herein, refers to a ribonucleic acid molecule, or complex of ribonucleic acid molecules, having a duplex structure including two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker." The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as a "small inhibitory RNA," "siRNA," "siRNA agent," "iRNA agent" or "RNAi agent."

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of," in as far as they refer to the Factor VII gene, herein refer to the at least partial suppression of the expression of the Factor VII gene, as manifested by a reduction of the amount of mRNA from the Factor VII gene which may be isolated from a first cell or group of cells in which the Factor VII gene is transcribed and which has or have been treated such that the expression of the Factor VII gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Factor VII gene transcription, e.g. the amount of protein encoded by the Factor VII gene which is secreted by a cell, or the number of cells displaying a certain phenotype, e.g apoptosis. In principle, Factor VII gene silencing may be determined in any cell expressing the target, either constitutively or by genomic engineering, and by any appropriate assay. However, when a reference is needed in order to determine whether a given siRNA inhibits the expression of the Factor VII gene by a certain degree and therefore is encompassed by the instant invention, the assays provided in the Examples below shall serve as such reference.

For example, in certain instances, expression of the Factor VII gene is suppressed by at least about 20%, 25%, 35%, 40% or 50% by administration of the double-stranded oligonucleotide of the invention. In one embodiment, the Factor VII gene is suppressed by at least about 60%, 70%, or 80% by administration of the double-stranded oligonucleotide of the invention. In a more preferred embodiment, the Factor VII gene is suppressed by at least about 85%, 90%, or 95% by administration of the double-stranded oligonucleotide of the invention.

The terms "treat," "treatment," and the like, refer to relief from or alleviation of a disease or disorder. In the context of the invention insofar as it relates to any of the other conditions recited herein below (e.g., a Factor VII-mediated condition other than a thrombotic disorder), the terms "treat," "treatment," and the like mean to relieve or alleviate at least one symptom associated with such condition, or to slow or reverse the progression of such condition.

A "therapeutically relevant" composition can alleviate a disease or disorder, or a symptom of a disease or disorder when administered at an appropriate dose.

As used herein, the term "Factor VII-mediated condition or disease" and related terms and phrases refer to a condition or disorder characterized by inappropriate, e.g., greater than normal, Factor VII activity. Inappropriate Factor VII functional activity might arise as the result of Factor VII expression in cells which normally do not express Factor VII, or increased Factor VII expression (leading to, e.g., a symptom of a viral hemorrhagic fever, or a thrombus). A Factor VII-mediated condition or disease may be completely or partially mediated by inappropriate Factor VII functional activity. However, a Factor VII-mediated condition or disease is one in which modulation of Factor VII results in some effect on the underlying condition or disorder (e.g., a Factor VII inhibitor results in some improvement in patient well-being in at least some patients).

A "hemorrhagic fever" includes a combination of illnesses caused by a viral infection. Fever and gastrointestinal symptoms are typically followed by capillary hemorrhaging.

A "coagulopathy" is any defect in the blood clotting mechanism of a subject.

As used herein, a "thrombotic disorder" is any disorder, preferably resulting from unwanted FVII expression, including any disorder characterized by unwanted blood coagulation.

As used herein, the phrases "therapeutically effective amount" and "prophylactically effective amount" refer to an amount that provides a therapeutic benefit in the treatment, prevention, or management of a viral hemorrhagic fever, or an overt symptom of such disorder, e.g., hemorraging, fever, weakness, muscle pain, headache, inflammation, or circulatory shock. The specific amount that is therapeutically effective can be readily determined by ordinary medical practitioner, and may vary depending on factors known in the art, such as, e.g. the type of thrombotic disorder, the patient's history and age, the stage of the disease, and the administration of other agents.

As used herein, a "pharmaceutical composition" includes a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

Characteristic of Nucleic Acid-Lipid Particles

In certain embodiments, the invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) drug to lipid ratio; (2) encapsulation efficiency; and (3) particle size. High drug to lipid rations, high encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be on a mole per mole basis or on a weight per weight basis, or on a weight per mole basis. For final, administration-ready compositions, the nucleic acid:lipid ratio is calculated after dialysis, chromatography and/or enzyme (e.g., nuclease) digestion has been employed to remove as much of the external nucleic acid as possible;

Encapsulation efficiency refers to the drug to lipid ratio of the starting mixture divided by the drug to lipid ratio of the final, administration competent composition. This is a measure of relative efficiency. For a measure of absolute efficiency, the total amount of nucleic acid added to the starting mixture that ends up in the administration competent composition, can also be calculated. The amount of lipid lost during the formulation process may also be calculated. Efficiency is a measure of the wastage and expense of the formulation; and Size indicates the size (diameter) of the particles formed. Size distribution may be determined using quasi-elastic light scattering (QELS) on a Nicomp Model 370 sub-micron particle sizer. Particles under 200 nm are preferred for distribution to neo-vascularized (leaky) tissues, such as neoplasms and sites of inflammation.

Methods of Preparing Lipid Particles

The methods and compositions of the invention make use of certain cationic lipids, the synthesis, preparation and characterization of which is described below and in the accompanying Examples. In addition, the present invention provides methods of preparing lipid particles, including those associated with a therapeutic agent, e.g., a nucleic acid. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 3 wt % to about 25 wt %, preferably 5 to 15 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

As described above, several of these cationic lipids are amino lipids that are charged at a pH below the $pK_a$ of the amino group and substantially neutral at a pH above the $pK_a$. These cationic lipids are termed titratable cationic lipids and can be used in the compositions of the invention using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the composition of nucleic acid-lipid particles are provided in U.S. Pat. Nos. 6,287,591 and 6,858,225, incorporated herein by reference.

It is further noted that the vesicles formed in this manner provide compositions of uniform vesicle size with high content of nucleic acids. Additionally, the vesicles have a size range of from about 30 to about 150 nm, more preferably about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g. pH 7.5) the surface of the lipid particle or liposome is neutralized, allowing any external nucleic acid to be removed. More detailed information on the formulation process is provided in various publications (e.g., U.S. Pat. Nos. 6,287,591 and 6,858,225).

In view of the above, the present invention provides methods of preparing lipid/nucleic acid compositions. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

In certain embodiments, the mixture of lipids includes at least two lipid components: a first amino lipid component of the present invention that is selected from among lipids which have a pKa such that the lipid is cationic at pH below the pKa and neutral at pH above the pKa, and a second lipid component that is selected from among lipids that prevent particle aggregation during lipid-nucleic acid particle formation. In particular embodiments, the amino lipid is a novel cationic lipid of the present invention.

In preparing the nucleic acid-lipid particles of the invention, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567).

In accordance with the invention, the lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. Nos. 6,287,591 and 6,858,225). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of composition produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods of the present invention further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the pKa of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the pKa of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Method of Use

The lipid particles of the invention may be used to deliver a therapeutic agent to a cell, in vitro or in vivo. In particular embodiments, the therapeutic agent is a nucleic acid, which is delivered to a cell using a nucleic acid-lipid particles of the invention. While the following description o various methods of using the lipid particles and related pharmaceutical compositions of the invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the invention provides methods for introducing a nucleic acid into a cell. Preferred nucleic acids for introduction into cells are siRNA, immune-stimulating oligonucleotides, plasmids, antisense and ribozymes. These methods may be carried out by contacting the particles or compositions of the invention with the cells for a period of time sufficient for intracellular delivery to Occur.

The compositions of the invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 μmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2\times10^4$ cells/mL. The concentration of the suspension added to the cells is preferably of from about 0.01 to 20 μg/mL, more preferably about 1 μg/mL.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions of the invention include introduction of antisense oligonucleotides in cells (see, Bennett, et al., *Mol. Pharm.* 41:1023-1033 (1992)).

Alternatively, the compositions of the invention can also be used for deliver of nucleic acids to cells in vivo, using methods which are known to those of skill in the art. With respect to application of the invention for delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278-281 (1989)) or by direct injection at the site of disease (Culver, Human Gene Therapy, Mary-Ann Liebert, Inc., Publishers, New York. pp. 70-71 (1994)).

The methods of the invention may be practiced in a variety of hosts. Preferred hosts include mammalian species, such as humans, non-human primates, dogs, cats, cattle, horses, sheep, and the like.

Dosages for the lipid-therapeutic agent particles of the invention will depend on the ratio of therapeutic agent to lipid and the administrating physician's opinion based on age, weight, and condition of the patient.

In one embodiment, the invention provides a method of modulating the expression of a target polynucleotide or polypeptide. These methods generally comprise contacting a cell with a lipid particle of the invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value. For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polynucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In one particular embodiment, the invention provides a method of modulating the expression of a polypeptide by a cell, comprising providing to a cell a lipid particle that consists of or consists essentially of a cationic lipid of formula (I) (e.g., a lipid of formula (II), (III), (IV), (V) or (VI)), a neutral lipid, a sterol, a PEG of PEG-modified lipid, e.g., in a molar ratio of about 35-65% of cationic lipid of formula (I), 3-12% of the neutral lipid, 15-45% of the sterol, and 0.5-10% of the PEG or PEG-modified lipid, wherein the lipid particle is associated with a nucleic acid capable of modulating the expression of the polypeptide. In particular embodiments, the molar lipid ratio is approximately 60/7.5/31/1.5 or 57.5/7.5/31.5/3.5 (mol % LIPID I/DSPC/Chol/PEG-DMG). In particular embodiments, the molar ratio is approximately 50/10/38.5/1.5 (mol % LIPID V/DSPC/Chol/PEG-DMG) or approximately 50/10/38.5/1.5 (mol % LIPID VI/DSPC/Chol/PEG-DSG). In another group of embodiments, the neutral lipid in these compositions is replaced with DPPC, POPC, DOPE or SM. In another group of embodiments, the PEG or PEG-modified lipid is PEG-DSG.

In particular embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the invention provides a method of treating a disease or disorder characterized by overexpression of a polypeptide in a subject, comprising providing to the subject a pharmaceutical composition of the invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of Lipid A, DSPC, Chol and PEG-DMG, PEG-C-DOMG or PEG-DMA, e.g., in a molar ratio of about 35-65% of cationic lipid of formula (I) (e.g., a lipid of formula (II), (III), (IV), (V) or (VI)), 3-12% of the neutral lipid, 15-45% of the sterol, and 0.5-10% of the PEG or PEG-modified lipid PEG-DMG, PEG-C-DOMG or PEG-DMA, wherein the lipid particle is associated with the therapeutic nucleic acid. In particular embodiments, the molar lipid ratio is approximately 60/7.5/31/1.5 or 57.5/7.5/31.5/3.5 (mol % LIPID I/DSPC/Chol/PEG-DMG). In particular embodiments, the molar ratio is approximately 50/10/38.5/1.5 (mol % LIPID V/DSPC/Chol/PEG-DMG) or approximately 50/10/38.5/1.5 (mol % LIPID VI/DSPC/Chol/PEG-DSG). In another group of embodiments, the neutral lipid in these compositions is replaced with DPPC, POPC, DOPE or SM. In another group of embodiments, the PEG or PEG-modified lipid is PEG-DSG.

In another related embodiment, the invention includes a method of treating a disease or disorder characterized by underexpression of a polypeptide in a subject, comprising providing to the subject a pharmaceutical composition of the invention, wherein the therapeutic agent is a plasmid that encodes the polypeptide or a functional variant or fragment thereof.

The invention further provides a method of inducing an immune response in a subject, comprising providing to the subject the pharmaceutical composition of the invention, wherein the therapeutic agent is an immunostimulatory oligonucleotide. In certain embodiments, the immune response is a humoral or mucosal immune response consists of or consists essentially of Lipid A, DSPC, Chol and PEG-DMG, PEG-C-DOMG or PEG-DMA, e.g., in a molar ratio of about 35-65% of cationic lipid of formula (I) (e.g., a lipid of formula (II), (III), (IV), (V) or (VI)), 3-12% of the neutral lipid, 15-45% of the sterol, and 0.5-10% of the PEG or PEG-modified lipid PEG-DMG, PEG-C-DOMG or PEG-DMA, wherein the lipid particle is associated with the therapeutic nucleic acid. In particular embodiments, the molar lipid ratio is approximately 60/7.5/31/1.5 or 57.5/7.5/31.5/3.5 (mol % LIPID I/DSPC/Chol/PEG-DMG). In particular embodiments, the molar ratio is approximately 50/10/38.5/1.5 (mol % LIPID V/DSPC/Chol/PEG-DMG) or approximately 50/10/38.5/1.5 (mol % LIPID VI/DSPC/Chol/PEG-DSG). In another group of embodiments, the neutral lipid in these compositions is replaced with DPPC, POPC, DOPE or SM. In another group of embodiments, the PEG or PEG-modified lipid is PEG-DSG.

In further embodiments, the pharmaceutical composition is provided to the subject in combination with a vaccine or antigen. Thus, the invention itself provides vaccines comprising a lipid particle of the invention, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasite.

A variety of tumor antigens, infections agent antigens, and antigens associated with other disease are well known in the art and examples of these are described in references cited herein. Examples of antigens suitable for use in the invention include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and rubella antigens. In one embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of skill in the art will know of other antigens suitable for use in the invention.

Tumor-associated antigens suitable for use in the subject invention include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESOT, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas species*, and *Salmonella* species. Specific examples of infectious bacteria include but are not limited to: *Helicobacter pyloris, Borelia burgdorferi, Legionella pneumophilia, Mycobacteria* sps (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus infuenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

Additional examples of pathogens include, but are not limited to, infectious fungi that infect mammals, and more particularly humans. Examples of infectious fingi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (i.e., protists) include *Toxoplasma gondii*.

Pharmaceutical Compositions

In one embodiment, the invention provides pharmaceutical compositions comprising a nucleic acid agent identified by the liver screening model described herein. The composition includes the agent, e.g., a dsRNA, and a pharmaceutically acceptable carrier. The pharmaceutical composition is useful for treating a disease or disorder associated with the expression or activity of the gene. Such pharmaceutical compositions are formulated based on the mode of delivery. One example is compositions that are formulated for systemic administration via parenteral delivery.

Pharmaceutical compositions including the identified agent are administered in dosages sufficient to inhibit expression of the target gene, e.g., the Factor VII gene. In general, a suitable dose of dsRNA agent will be in the range of 0.01 to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for vaginal delivery of agents, such as could be used with the agents of the invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

In particular embodiments, pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical compositions can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the lipid-therapeutic agent (e.g., nucleic acid) particels of the invention may include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation. Rather, it may also provide a means for increasing circulation lifetime and increasing the delivery of the lipid-nucleic acid composition to the target tissues.

The invention also provides lipid-therapeutic agent compositions in kit form. The kit will typically be comprised of a container that is compartmentalized for holding the various elements of the kit. The kit will contain the particles or pharmaceutical compositions of the invention, preferably in dehydrated or concentrated form, with instructions for their rehydration or dilution and administration. In certain embodiments, the particles comprise the active agent, while in other embodiments, they do not.

The pharmaceutical compositions containing an agent identified by the liver screening model may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal), oral or parenteral. Administration may also be designed to result in preferential localization to particular tissues through local delivery, e.g. by direct intraarticular injection into joints, by rectal administration for direct delivery to the gut and intestines, by intravaginal administration for delivery to the cervix and vagina, by intravitreal administration for delivery to the eye. Parenteral administration includes intravenous, intraarterial, intraarticular, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the dsRNAs of the invention are in admixture with a topical delivery component, such as a lipid, liposome, fatty acid, fatty acid ester, steroid, chelating agent or surfactant. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). DsRNAs of the invention may be encapsulated within liposomes or may form complexes thereto, in particular to cationic liposomes. Alternatively, dsRNAs may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which dsRNAs of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. DsRNAs of the invention may be delivered orally, in granular form including sprayed dried particles, or complexed to form micro or nanoparticles. DsRNA complexing agents include polyamino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions include, but are not limited to, solutions, emulsions, and liposome-containing compositions. These compositions may be generated from a variety of components that include, but are not limited to, preformed liquids, self-emulsifying solids and self-emulsifying semi-solids.

The pharmaceutical compositions, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the compositions are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions of the invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the invention This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

EXAMPLES

The following examples are offered to illustrate, but not to limit the claimed invention.

Example 1: In Vivo Rodent Factor VII Silencing Experiments

C57BL/6 Mice (Charles River Labs, MA) and Sprague-Dawley rats (Charles River Labs, MA) received either saline or formulated siRNA via tail vein injection at a volume of 0.01 mL/g. At various time points after administration, serum samples were collected by retroorbital bleed. Serum levels of Factor VII protein were determined in samples using a chromogenic assay (Biophen FVII, Aniara Corporation, OH). To determine liver mRNA levels of Factor VII, animals were sacrificed and livers were harvested and snap frozen in liquid nitrogen. Tissue lysates were prepared from the frozen tissues and liver mRNA levels of Factor VII were quantified using a branched DNA assay (QuantiGene Assay, Panomics, CA).

Example 2: Regulation of Mammalian Gene Expression Using Nucleic Acid-Lipid Particles Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining sirna-mediated downregulation of hepatocyte-derived proteins, as well as monitoring plasma concentrations and tissue distribution of the nucleic acid lipid particles and siRNA.
Factor VII Knockdown in Mice FVII activity was evaluated in FVII siRNA-treated animals at 24 hours after intravenous (bolus) injection in C57BL/6 mice. FVII was measured using a commercially available kit for determining protein levels in serum or tissue, following the manufacturer's instructions at a microplate scale. FVII reduction was determined against untreated control mice, and the results were expressed as % Residual FVII. Four dose levels (2, 5, 12.5, 25 mg/kg FVII siRNA) were used in the initial screen of each novel liposome composition, and this dosing was expanded in subsequent studies based on the results obtained in the initial screen.
Determination of Tolerability The tolerability of each novel liposomal siRNA composition was evaluated by monitoring weight change, cageside observations, clinical chemistry and, in some instances, hematology. Animal weights were recorded prior to treatment and at 24 hours after treatment. Data was recorded as % Change in Body Weight. In addition to body weight measurements, a full clinical chemistry panel, including liver function markers, was obtained at each dose level (2, 5, 12.5 and 25 mg/kg siRNA) at 24 hours post-injection using an aliquot of the serum collected for FVII analysis. Samples were sent to the Central Laboratory for Veterinarians (Langley, BC) for analysis. In some instances, additional mice were included in the treatment group to allow collection of whole blood for hematology analysis.
Determination of Therapeutic Index Therapeutic index (TI) is an arbitrary parameter generated by comparing measures of toxicity and activity. For these studies, TI was determined as:

TI=MTD (maximum tolerated dose)/$ED_{50}$ (dose for 50% FVII knockdown)

The MTD for these studies was set as the lowest dose causing >7% decrease in body weight and a >200-fold increase in alanine aminotransferase (ALT), a clinical chemistry marker with good specificity for liver damage in rodents. The ED 50 was determined from FVII dose-activity curves.

Example 3: General Protocol for the Extrusion Method

Lipids (Lipid (I), (II), (III), (IV), (V) or (VI): DSPC: cholesterol:DMG-PEG) are solubilized and mixed in ethanol according to the desired molar ratio. Liposomes are formed by an ethanol injection method where mixed lipids are added to sodium acetate buffer at pH 5.2. This results in the spontaneous formation of liposomes in 35% ethanol. The liposomes are extruded through a 0.08 µm polycarbonate membrane at least 2 times. A stock siRNA solution was prepared in sodium acetate and 35% ethanol and was added to the liposome to load. The siRNA-liposome solution was incubated at 37° C. for 30 min and, subsequently, diluted. Ethanol was removed and exchanged to PBS buffer by dialysis or tangential flow filtration.

Example 4: General Protocol for the In-Line Mixing Method

Individual and separate stock solutions are prepared—one containing lipid and the other siRNA. Lipid stock containing Lipid (I), (II), (III), (IV), (V) or (VI); DSPC:cholesterol: PEG lipid is prepared by solubilized in 90% ethanol. The remaining 10% is low pH citrate buffer. The concentration of the lipid stock is 4 mg/mL. The pH of this citrate buffer can range between pH 3-5, depending on the type of fusogenic lipid employed. The siRNA is also solubilized in citrate buffer at a concentration of 4 mg/mL. For small scale, 5 mL of each stock solution is prepared.

Stock solutions are completely clear and lipids must be completely solubilized before combining with siRNA. Therefore stock solutions may be heated to completely solubilize the lipids. The siRNAs used in the process may be unmodified oligonucleotides or modified and may be conjugated with lipophilic moieties such as cholesterol.

The individual stocks are combined by pumping each solution to a T-junction. A dual-head Watson-Marlow pump is used to simultaneously control the start and stop of the two streams. A 1.6 mm polypropylene tubing is further downsized to a 0.8 mm tubing in order to increase the linear flow rate. The polypropylene line (ID=0.8 mm) are attached to either side of a T-junction. The polypropylene T has a linear edge of 1.6 mm for a resultant volume of 4.1 mm 3. Each of the large ends (1.6 mm) of polypropylene line is placed into test tubes containing either solubilized lipid stock or solubilized siRNA. After the T-junction a single tubing is placed where the combined stream will emit. The tubing is then extending into a container with 2x volume of PBS. The PBS is rapidly stirring. The flow rate for the pump is at a setting of 300 rpm or 110 mL/min. Ethanol is removed and exchanged for PBS by dialysis. The lipid compositions are then concentrated using centrifugation or diafiltration to an appropriate working concentration.

Example 5: Efficacy of Compositions with Various Lipid Ratios

Various lipid ratios were tested as shown in the table below. Included are Lipid T ("T"), Cholesterol ("C") and PEG-lipid (PEG-DMG). The relative molar percentages of the components are listed below. Therefore, "T50-C40-P10" contains 50 mol % of Lipid T, 40 mol % of cholesterol, and 10 mol % of PEG-DMG.
The siRNA duplex used was AD-1661 targeting the Factor VII gene (FVII):

| DUPLEX NAME | strand | oligoSeq |
|---|---|---|
| AD-1661 | sense | GGAUfCfAUfCfUfCfAAGUfCfUfUfACfdTsdT |
| | antis | GUfAAGACfUfUfGAGAUfGAUfCfCfdTsdT |

Experimental Plan
Animals C57BL/6
Total 57
siRNA 1661

| Group | Group size | Conc. (mg/mL) | Inj Vol. (uL/g) | Dose (mg/kg) | Vehicle |
|---|---|---|---|---|---|
| 1 | 3 | | 10 | 0.00 | PBS |
| 2 | 3 | 0.005 | 10 | 0.050 | T50-C40-P10 |
| 3 | 3 | 0.001 | 10 | 0.010 | T50-C40-P10 |
| 4 | 3 | 0.000 | 10 | 0.002 | T50-C40-P10 |
| 5 | 3 | 0.005 | 10 | 0.050 | T60-C30-P10 |
| 6 | 3 | 0.001 | 10 | 0.010 | T60-C30-P10 |
| 7 | 3 | 0.000 | 10 | 0.002 | T60-C30-P10 |
| 8 | 3 | 0.005 | 10 | 0.050 | T55-C40-P5 |
| 9 | 3 | 0.001 | 10 | 0.010 | T55-C40-P5 |
| 10 | 3 | 0.000 | 10 | 0.002 | T55-C40-P5 |
| 11 | 3 | 0.005 | 10 | 0.050 | T65-C40-P5 |
| 12 | 3 | 0.001 | 10 | 0.010 | T65-C40-P5 |
| 13 | 3 | 0.000 | 10 | 0.002 | T65-C40-P5 |
| 14 | 3 | 0.005 | 10 | 0.050 | T40-D10-C40-P10 |
| 15 | 3 | 0.001 | 10 | 0.010 | T40-D10-C40-P10 |
| 16 | 3 | 0.000 | 10 | 0.002 | T40-D10-C40-P10 |
| 17 | 3 | 0.005 | 10 | 0.050 | T50-D7.5-C37.5-P5 |
| 18 | 3 | 0.001 | 10 | 0.010 | T50-D7.5-C37.5-P5 |
| 19 | 3 | 0.000 | 10 | 0.002 | T50-D7.5-C37.5-P5 |

Result (FIG. 1)

| | Normalized results | | | Average | Stdev |
|---|---|---|---|---|---|
| PBS | 1.0777 | 0.8956 | 1.0267 | 1.0000 | 0.0940 |
| T50-C40-P10 | 0.0130 | 0.0282 | 0.0413 | 0.0275 | 0.0142 |
| | 0.1673 | 0.2415 | 0.3961 | 0.2683 | 0.1167 |
| | 0.7941 | 0.6029 | 0.6279 | 0.6750 | 0.1039 |
| T60-C30-P10 | 0.0155 | 0.0210 | 0.0115 | 0.0160 | 0.0048 |
| | 0.1984 | 0.1737 | 0.2282 | 0.2001 | 0.0273 |
| | 0.7082 | 0.7646 | 0.6351 | 0.7026 | 0.0649 |
| T55-C40-P5 | 0.0727 | 0.0425 | 0.0885 | 0.0679 | 0.0234 |
| | 0.3301 | 0.5261 | 0.4033 | 0.4198 | 0.0990 |
| | 0.7570 | 0.7983 | 0.7479 | 0.7677 | 0.0269 |
| T65-C40-P5 | 0.0348 | 0.0756 | 0.0308 | 0.0470 | 0.0248 |
| | 0.3034 | 0.3036 | 0.5193 | 0.3754 | 0.1246 |
| | 0.5293 | 0.5894 | 0.5610 | 0.5599 | 0.0300 |
| T40-D10-C40-P10 | 0.0827 | 0.1229 | 0.1694 | 0.1250 | 0.0434 |
| | 0.5354 | 0.6237 | 0.6473 | 0.6021 | 0.0590 |
| | 1.1071 | 0.6696 | 0.8280 | 0.8682 | 0.2215 |
| T50-D7.5-C37.5-P5 | 0.1257 | 0.0687 | 0.0650 | 0.0865 | 0.0340 |
| | 0.2956 | 0.6145 | 0.5443 | 0.4848 | 0.1676 |
| | 0.7589 | 0.7758 | 0.7661 | 0.7669 | 0.0084 |

Example 6: Efficacy of In-Line Mixed Compositions in Mice

Experimental Plan
Animals C57BL/6
Total 21
SiRNA 1661

| Group | Group size | Conc. (mg/mL) | Inj Vol. (uL/g) | Dose (mg/kg) | Vehicle |
|---|---|---|---|---|---|
| 1 | 3 | | 10 | 0.00 | PBS |
| 2 | 3 | 0.001 | 10 | 0.010 | T60-D7.5-C31-P1.5 IL [0.4] |
| 3 | 3 | 0.000 | 10 | 0.002 | T60-D7.5-C31-P1.5 IL [0.4] |
| 4 | 3 | 0.001 | 10 | 0.010 | T60-D7.5-C31-P1.5 IL 12.5:1 lipid:siRNA |
| 5 | 3 | 0.000 | 10 | 0.002 | T60-D7.5-C31-P1.5 IL 12.5:1 lipid:siRNA |
| 6 | 3 | 0.001 | 10 | 0.010 | T50-D10-C38.5-P1.5 IL |
| 7 | 3 | 0.000 | 10 | 0.002 | T50-D10-C38.5-P1.5 IL |

Figure 2:
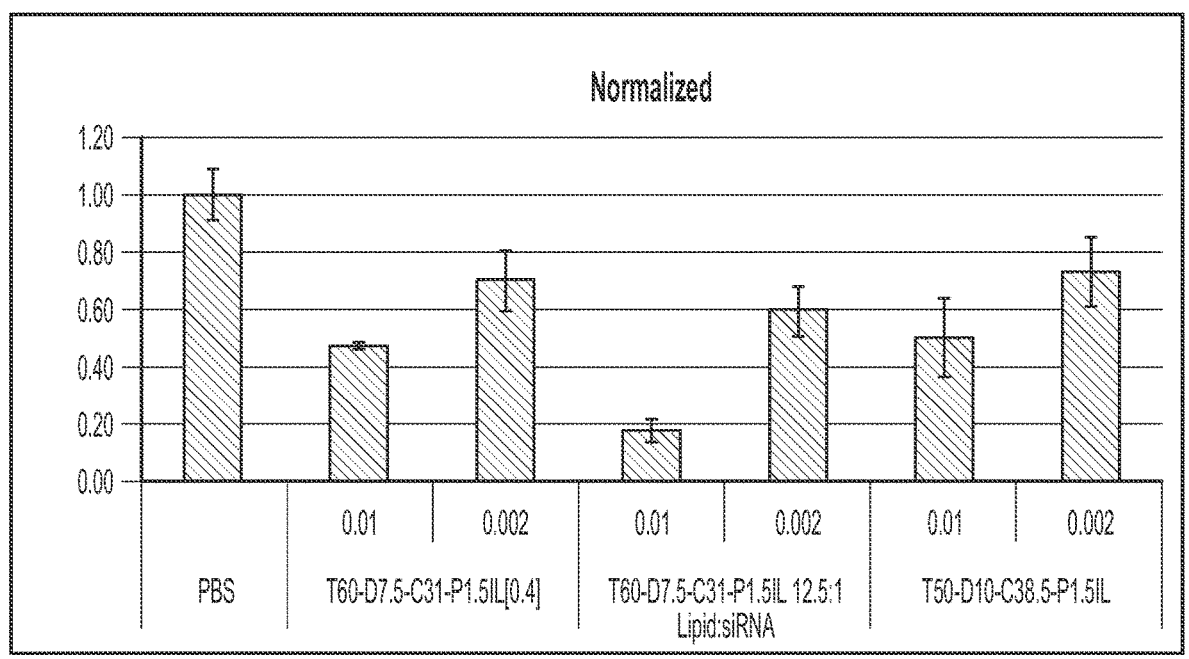
FIG. 2 is a graph showing the effect on body weight change with various lipid ratios.

Result (FIG. 2)

| Group | | FVII protein Inhibition | | | Normalized Inhibition | | |
|---|---|---|---|---|---|---|---|
| | mg/kg | AVE. | SD | % | AVE. | SD | % |
| PBS | | 1.17 | 0.10 | −17 | 1.00 | 0.08 | 0 |
| T60-D7.5-C31-P1.5 IL [0.4] | 0.01 | 0.55 | 0.01 | 45 | 0.47 | 0.01 | 53 |
| | 0.002 | 0.82 | 0.12 | 18 | 0.70 | 0.10 | 30 |
| T60-D7.5-C31-P1.5 IL 12.5:1 lipid:siRNA | 0.01 | 0.21 | 0.05 | 80 | 0.18 | 0.04 | 82 |
| | 0.002 | 0.69 | 0.10 | 31 | 0.59 | 0.09 | 41 |
| T50-D10-C38.5-P1.5 IL | 0.01 | 0.59 | 0.16 | 41 | 0.50 | 0.14 | 50 |
| | 0.002 | 0.85 | 0.14 | 15 | 0.73 | 0.12 | 27 |

Example 7: Efficacy of In-Line Mixed (IL) Compositions in Mice with Various Liposomal Compositions Experimental Plan
Animals C57BL/6
Total 39
siRNA 1661

| Group | Group size | Conc. (mg/mL) | Inj Vol. (uL/g) | Dose (mg/kg) | Vehicle |
|---|---|---|---|---|---|
| 1 | 3 | | 10 | 0.00 | PBS |
| 2 | 3 | 0.0050 | 10 | 0.050 | IL 60-7.5-31-1.5 10 mM citrate pH 3 |
| 3 | 3 | 0.0010 | 10 | 0.010 | IL 60-7.5-31-1.5 10 mM citrate pH 3 |
| 4 | 3 | 0.0002 | 10 | 0.002 | IL 60-7.5-31-1.5 10 mM citrate pH 3 |
| 5 | 3 | 0.0050 | 10 | 0.050 | IL 50-10-38.5-1.5 |
| 6 | 3 | 0.0010 | 10 | 0.010 | IL 50-10-38.5-1.5 |
| 7 | 3 | 0.0002 | 10 | 0.002 | IL 50-10-38.5-1.5 |
| 8 | 3 | 0.0050 | 10 | 0.050 | IL 60-38.5-1.5 |
| 9 | 3 | 0.0010 | 10 | 0.010 | IL 60-38.5-1.5 |
| 10 | 3 | 0.0002 | 10 | 0.002 | IL 60-38.5-1.5 |
| 11 | 3 | 0.0050 | 10 | 0.050 | IL 40-20-38.5-1.5 |

-continued

Experimental Plan
Animals C57BL/6
Total 39
siRNA 1661

| Group | Group size | Conc. (mg/mL) | Inj Vol. (uL/g) | Dose (mg/kg) | Vehicle |
|---|---|---|---|---|---|
| 10 | 3 | 0.0010 | 10 | 0.010 | IL 40-20-38.5-1.5 |
| 11 | 3 | 0.0002 | 10 | 0.002 | IL 40-20-38.5-1.5 |

Figure 3:
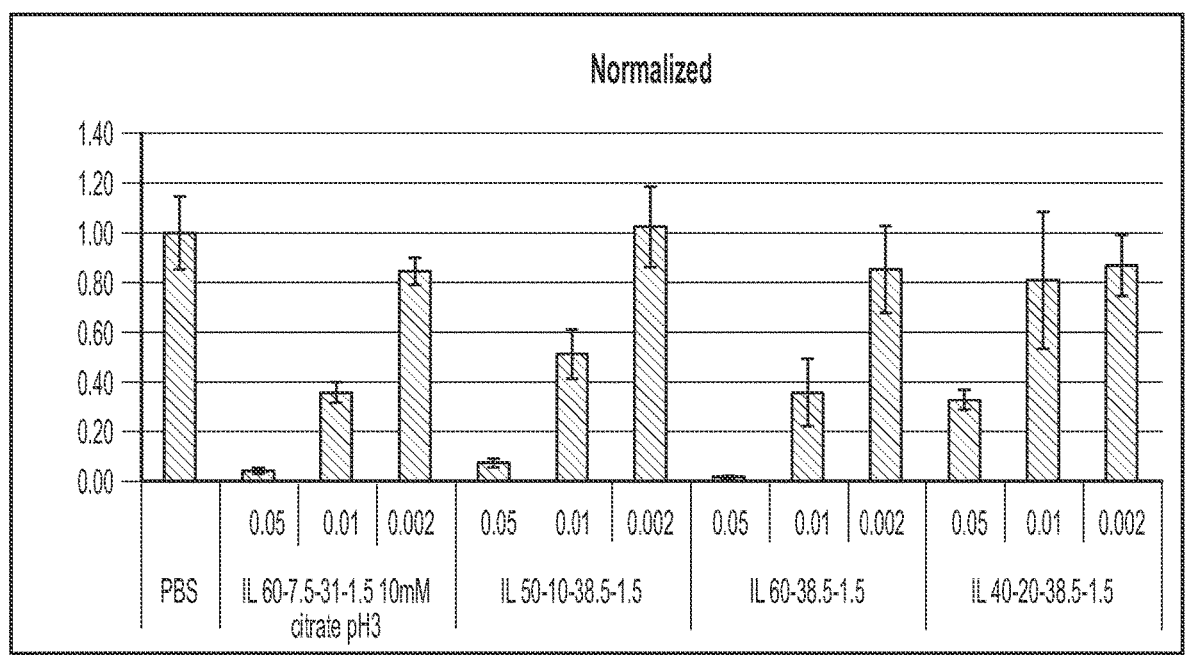
FIG. 3 is a graph illustrating the relative FVII protein with different amount of cationic lipid (I) and low PEG lipid.

Result (FIG. 3)

| Group | | FVII protein Inhibition | | | Normalized Inhibition | | |
|---|---|---|---|---|---|---|---|
| | mg/kg | AVE. | SD | % | AVE. | SD | % |
| PBS | | 0.88 | 0.13 | 12 | 1.00 | 0.14 | 0 |
| IL 60-7.5-31-1.5 | 0.05 | 0.04 | 0.01 | 96 | 0.05 | 0.01 | 95 |
| | 0.01 | 0.32 | 0.04 | 68 | 0.36 | 0.04 | 64 |
| 10 mM citrate pH 3 | 0.002 | 0.74 | 0.05 | 26 | 0.84 | 0.06 | 16 |
| IL 50-10-38.5-1.5 | 0.05 | 0.07 | 0.02 | 93 | 0.08 | 0.02 | 92 |
| | 0.01 | 0.45 | 0.09 | 55 | 0.51 | 0.10 | 49 |
| | 0.002 | 0.89 | 0.15 | 11 | 1.02 | 0.17 | -2 |
| IL 60-38.5-1.5 | 0.05 | 0.02 | 0.00 | 98 | 0.02 | 0.00 | 98 |
| | 0.01 | 0.32 | 0.12 | 68 | 0.36 | 0.13 | 64 |
| | 0.002 | 0.75 | 0.15 | 25 | 0.86 | 0.17 | 14 |
| IL 40-20-38.5-1.5 | 0.05 | 0.29 | 0.04 | 71 | 0.33 | 0.05 | 67 |
| | 0.01 | 0.71 | 0.24 | 29 | 0.81 | 0.28 | 19 |
| | 0.002 | 0.76 | 0.11 | 24 | 0.87 | 0.12 | 13 |

Example 8: Efficacy of IL Compositions in Mice with Various PEG and Neutral Lipids The effect of modifying PEG chain length or neutral lipids was examined. For neutral lipids, DOPC (dioleoyl-phosphatidylcholine) or DMPC (dimyristoylphosphatidylcholine) were tested. mPEG2000 conjugated lipids with either a C10 or C18 chain length were also tested at 1.5 mol %. Where indicated below with "IL", particles were generated using an in-line mixing method.

Experimental Plan
Animals C57BL/6
Total 57
siRNA 1661

| Group | Group size | Conc. (mg/mL) | Inj Vol. (uL/g) | Dose (mg/kg) | Vehicle |
|---|---|---|---|---|---|
| 1 | 3 | | 10 | 0.00 | PBS |
| 2 | 3 | 0.0050 | 10 | 0.050 | 50-10-38.5-1.5 |
| 3 | 3 | 0.0010 | 10 | 0.010 | 50-10-38.5-1.5 |
| 4 | 3 | 0.0002 | 10 | 0.002 | 50-10-38.5-1.5 |
| 5 | 3 | 0.0050 | 10 | 0.050 | IL 45-15-38.5-1.5 (DOPC) |
| 6 | 3 | 0.0010 | 10 | 0.010 | IL 45-15-38.5-1.5 (DOPC) |
| 7 | 3 | 0.0002 | 10 | 0.002 | IL 45-15-38.5-1.5 (DOPC) |
| 8 | 3 | 0.0050 | 10 | 0.050 | IL 45-15-38.5-1.5 (DMPC) |
| 9 | 3 | 0.0010 | 10 | 0.010 | IL 45-15-38.5-1.5 (DMPC) |
| 10 | 3 | 0.0002 | 10 | 0.002 | IL 45-15-38.5-1.5 (DMPC) |
| 11 | 3 | 0.0050 | 10 | 0.050 | IL 45-15-38.5-1.5 |
| 12 | 3 | 0.0010 | 10 | 0.010 | IL 45-15-38.5-1.5 |
| 13 | 3 | 0.0002 | 10 | 0.002 | IL 45-15-38.5-1.5 |
| 14 | 3 | 0.0050 | 10 | 0.050 | 50-10-38.5-1.5 (C10PEG) |
| 15 | 3 | 0.0010 | 10 | 0.010 | 50-10-38.5-1.5 (C10PEG) |
| 16 | 3 | 0.0002 | 10 | 0.002 | 50-10-38.5-1.5 (C10PEG) |
| 17 | 3 | 0.0050 | 10 | 0.050 | 50-10-38.5-1.5 (C18PEG) |
| 18 | 3 | 0.0010 | 10 | 0.010 | 50-10-38.5-1.5 (C18PEG) |
| 19 | 3 | 0.0002 | 10 | 0.002 | 50-10-38.5-1.5 (C18PEG) |

Figure 4:
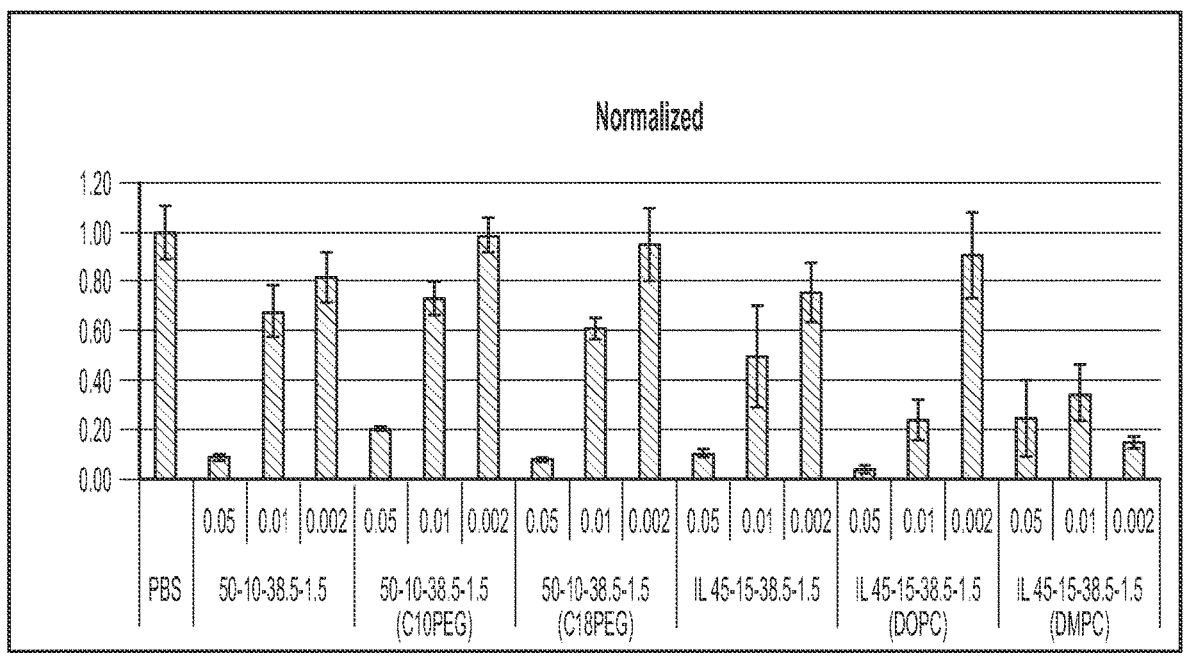
FIG. 4 is a graph showing the effect on body weight change with different amount of cationic lipid (I) and low PEG lipid.

Result: (FIG. 4)

| Group | | FVII protein Inhibition | | | Normalized Inhibition | | |
|---|---|---|---|---|---|---|---|
| | mg/kg | AVE. | SD | % | AVE. | SD | % |
| PBS | | 1.33 | 0.14 | -33 | 1.00 | 0.11 | 0 |
| 50-10-38.5-1.5 | 0.05 | 0.12 | 0.02 | 88 | 0.09 | 0.02 | 91 |
| | 0.01 | 0.90 | 0.13 | 10 | 0.68 | 0.10 | 32 |
| | 0.002 | 1.09 | 0.13 | -9 | 0.82 | 0.10 | 18 |
| 50-10-38.5-1.5 (C10PEG) | 0.05 | 0.28 | 0.01 | 72 | 0.21 | 0.01 | 79 |
| | 0.01 | 0.98 | 0.08 | 2 | 0.73 | 0.06 | 27 |
| | 0.002 | 1.32 | 0.09 | -32 | 0.99 | 0.07 | 1 |
| 50-10-38.5-1.5 (C18PEG) | 0.05 | 0.11 | 0.01 | 89 | 0.08 | 0.01 | 92 |
| | 0.01 | 0.81 | 0.06 | 19 | 0.61 | 0.04 | 39 |
| | 0.002 | 1.26 | 0.20 | -26 | 0.95 | 0.15 | 5 |
| IL 45-15-38.5-1.5 | 0.05 | 0.14 | 0.02 | 86 | 0.10 | 0.01 | 90 |
| | 0.01 | 0.67 | 0.27 | 33 | 0.50 | 0.20 | 50 |
| | 0.002 | 1.01 | 0.16 | -1 | 0.76 | 0.12 | 24 |
| IL 45-15-38.5-1.5 (DOPC) | 0.05 | 0.06 | 0.02 | 94 | 0.04 | 0.01 | 96 |
| | 0.01 | 0.32 | 0.11 | 68 | 0.24 | 0.08 | 76 |
| | 0.002 | 1.21 | 0.23 | -21 | 0.91 | 0.17 | 9 |
| IL 45-15-38.5-1.5 (DMPC) | 0.05 | 0.33 | 0.20 | 67 | 0.25 | 0.15 | 75 |
| | 0.01 | 0.46 | 0.15 | 54 | 0.35 | 0.11 | 65 |
| | 0.002 | 0.20 | 0.02 | 80 | 0.15 | 0.02 | 85 |

Example 9: Dose Response of AF12 in Mice

C57BL/6 mice (Charles River Labs, MA) and Sprague-Dawley rats (Charles River Labs, MA) received either saline or formulated siRNA via tail vein injection at a volume of 0.01 mL/g. At various time points after administration, serum samples were collected by retroorbital bleed. Serum levels of Factor VII protein were determined in samples using a chromogenic assay (Biophen FVII, Aniara Corporation, OH). To determine liver mRNA levels of Factor VII, animals were sacrificed and livers were harvested and snap frozen in liquid nitrogen. Tissue lysates were prepared from the frozen tissues and liver mRNA levels of Factor VII were quantified using a branched DNA assay (QuantiGene Assay, Panomics, CA).

Figure 6:
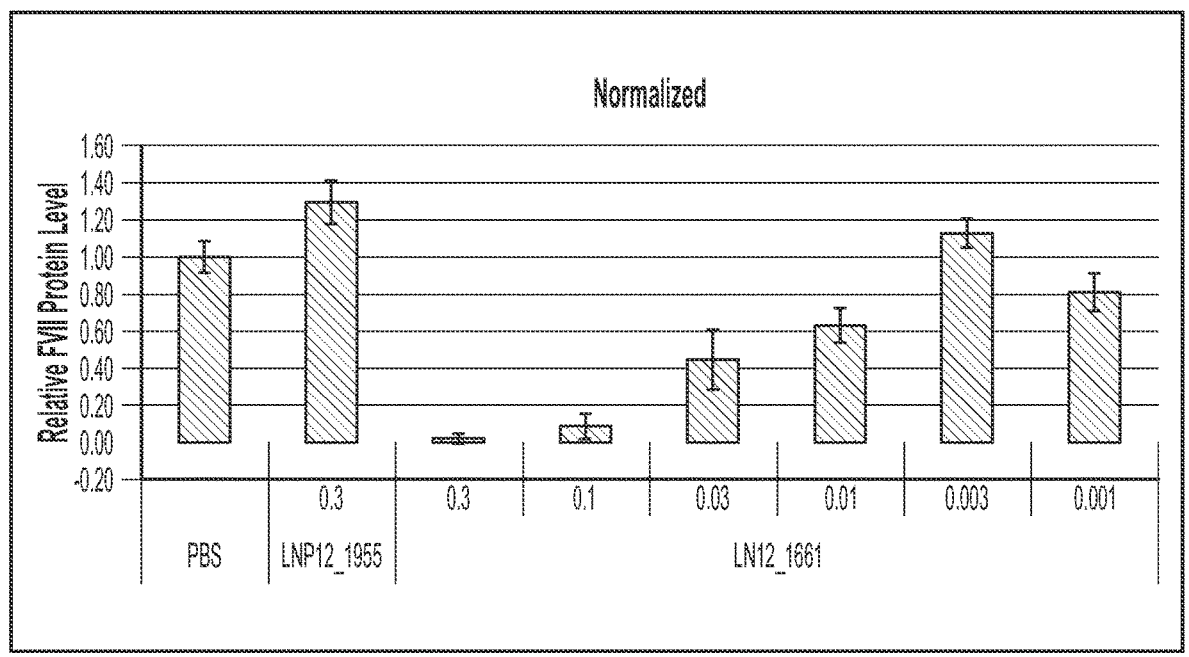
FIG. 6 is a graph illustrating the dose dependence response of FVII in various AF12 containing liposome compositions.

In vivo experiments were performed using liposome compositions comprising various concentrations of AF12 in the liposome composition. The AF12 dose response was tested from 0.001 mg/kg to 0.3 mg/kg using the standard Factor VII (FVII) siRNA duplex 1661. These results were compared with Luciferase control (duplex 1955) as shown in FIG. 6. Five animals were used for each of the eight groups per genotype in the experiment for a total of 40 animals. As shown in FIG. 6, increasing dose of the liposome composition generally produced an increase in the amount of knockdown of FVII.

Experimental Plan
Animals C57BL6
Total 40

| Group | Group size | Target | siRNA | Conc. (mg/mL) | Inj Vol. (uL/g) | Dose (mg/kg) | Vehicle/ Formulation |
|---|---|---|---|---|---|---|---|
| 1 | 5 | Luc | 1955 |  | 10 |  | PBS |
| 2 | 5 | FVII | 1661 | 0.03 | 10 | 0.300 | AF12 |
| 3 | 5 | FVII | 1661 | 0.03 | 10 | 0.300 | AF12 |
| 4 | 5 | FVII | 1661 | 0.01 | 10 | 0.100 | AF12 |
| 5 | 5 | FVII | 1661 | 0.003 | 10 | 0.030 | AF12 |
| 6 | 5 | FVII | 1661 | 0.001 | 10 | 0.010 | AF12 |
| 7 | 5 | FVII | 1661 | 0.0003 | 10 | 0.003 | AF12 |
| 8 | 5 | FVII | 1661 | 0.0001 | 10 | 0.001 | AF12 |

Example 10: Efficacy of AF12 Liposome Compositions in ApoE KO Mice

To further examine the role of ApoE in efficacy of various AF12 liposome compositions were administered containing the AD-1661 siRNA composition, at various concentrations.

Figure 7:
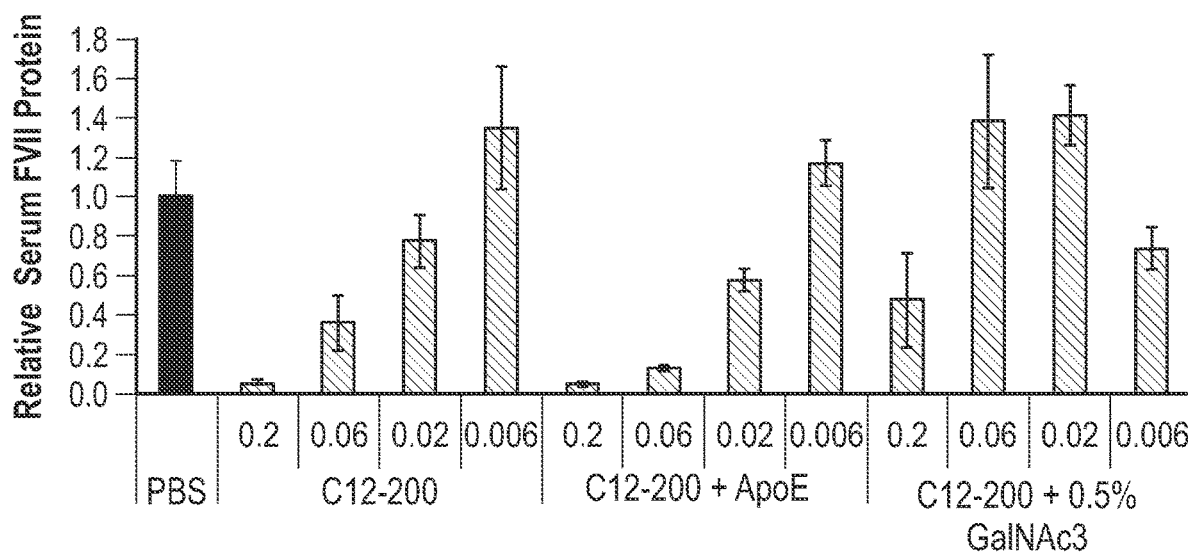
FIG. 7 is a graph illustrating the dose response of ApoE containing and GalNAc3 containing liposome compositions in ApoE knockout mice.

In vivo experiments were performed using liposome compositions comprising ApoE or N-acetyl galactosamine (GalNAc) conjugated lipids. GalNAc was chosen as a possible targeting ligand as it is known that the GalNAc receptor is thought to be highly expressed in the liver. A study was therefore performed using C57BL/6 and ApoE knockout mice essentially as described in Example 6 to test the efficacy of the AF12 formulations further comprising various concentrations of GalNAc3-PEG-DSG lipids. In all experiments, the total amount of PEG-conjugated lipids was kept constant (e.g., where 0.5% mol of GalNAc3-PEG is added, the corresponding amount of PEG-DMG was decreased by 0.5% mol to keep the total PEG-lipid at 1.5% mol). As shown in FIG. 7, addition of ApoE to the liposome composition has little to no effect on the dose response of the AF12 containing liposome composition. The GalNAc3 containing compositions appear to be slightly less effective in knocking down FVII.

Experimental Plan
Animals ApoE KO mice
Total 39

| Group | Group size | Target | siRNA | Conc. (mg/mL) | Inj Vol. (uL/g) | Dose (mg/kg) | Vehicle |
|---|---|---|---|---|---|---|---|
| 1 | 3 |  |  |  | 10 |  | C12-200BS |
| 2 | 3 | FVII | 1661 | 0.02 | 10 | 0.200 | AF12 |
| 3 | 3 | FVII | 1661 | 0.006 | 10 | 0.060 |  |
| 4 | 3 | FVII | 1661 | 0.002 | 10 | 0.020 |  |
| 5 | 3 | FVII | 1661 | 0.0006 | 10 | 0.006 |  |
| 6 | 3 | FVII | 1661 | 0.020 | 10 | 0.200 | C12-200 w ApoE |
| 7 | 3 | FVII | 1661 | 0.006 | 10 | 0.060 |  |
| 8 | 3 | FVII | 1661 | 0.002 | 10 | 0.020 | AF12 |
| 9 | 3 | FVII | 1661 | 0.0006 | 10 | 0.006 |  |
| 10 | 3 | FVII | 1661 | 0.020 | 10 | 0.200 | C12-200 w 0.5% GalNAc3-PEG-Lipid |
| 11 | 3 | FVII | 1661 | 0.006 | 10 | 0.060 |  |
| 12 | 3 | FVII | 1661 | 0.002 | 10 | 0.020 |  |
| 13 | 3 | FVII | 1661 | 0.0006 | 10 | 0.006 |  |

Example 11: AF12 Tested in WT and ApoE Mice and in WT and LDLR Knockout Mice To examine the ApoE dependence of various AF12 liposome compositions, efficacy of these liposome compositions in LDLR (LDL receptor) deficient mice were evaluated. Dimished efficacy of the liposome compositions in LDLR deficient mice would suggest ApoE dependence. AF12 liposome compositions in wildtype and LDLR KO mice were administered containing the AD-1661 siRNA composition, at various concentrations as illustrated below. The first group received PBS as a negative control.

| Group | Mice | Target | siRNA | Conc. (mg/mL) | Inj vol (ul) | Dose (mg/kg) | Vehicle |
|---|---|---|---|---|---|---|---|
| 1 | C57Bl/6 | Luc |  |  | 10 |  | PBS |
| 2 | C57Bl/6 | FVII | 1661 | 0.03 | 10 | 0.300 | AF12 |
| 3 | C57Bl/6 | FVII | 1661 | 0.03 | 10 | 0.300 | AF12 |
| 4 | C57Bl/6 | FVII | 1661 | 0.01 | 10 | 0.100 | AF12 |
| 5 | C57Bl/6 | FVII |  | 0.003 | 10 | 0.030 | AF12 |
| 6 | C57Bl/6 | FVII | 1661 | 0.001 | 10 | 0.010 | AF12 |
| 7 | C57Bl/6 | FVII | 1661 | 0.0003 | 10 | 0.003 | AF12 |
| 8 | LDLR KO |  |  |  | 10 |  | PBS |
| 9 | LDLR KO | Luc | 1955 | 0.03 | 10 | 0.300 | AF12 |
| 10 | LDLR KO | FVII | 1661 | 0.03 | 10 | 0.300 | AF12 |
| 11 | LDLR KO | FVII | 1661 | 0.01 | 10 | 0.100 | AF12 |
| 12 | LDLR KO | FVII | 1661 | 0.003 | 10 | 0.030 | AF12 |
| 13 | LDLR KO | FVII | 1661 | 0.001 | 10 | 0.010 | AF12 |
| 14 | LDLR KO | FVII | 1661 | 0.0003 | 10 | 0.003 | AF12 |

Figure 8:
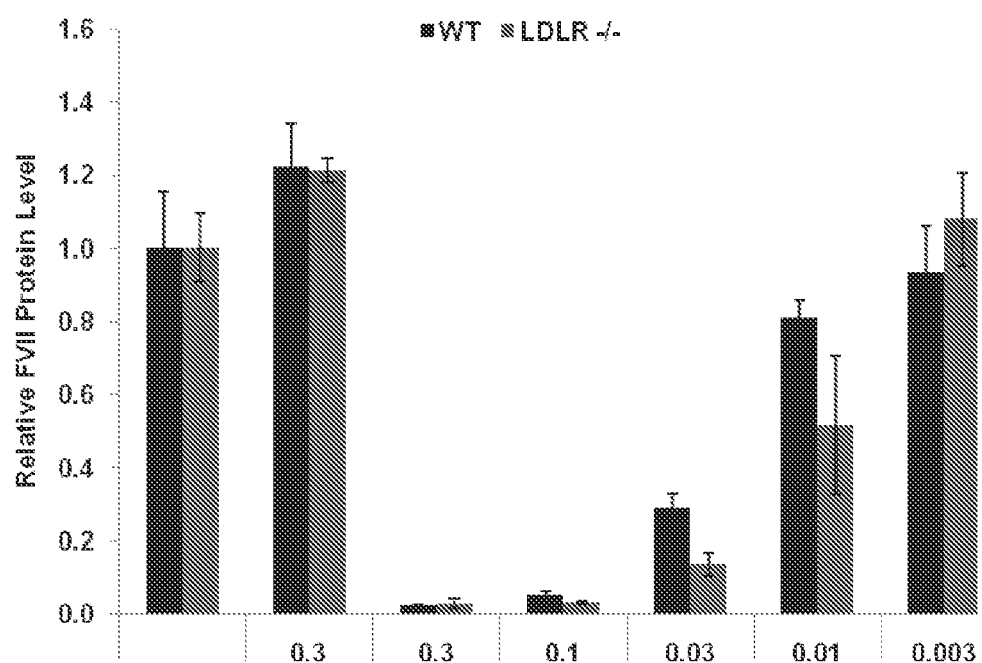
FIG. 8 is a graph illustrating the relative FVII protein level with different amounts of AF12 in WT (C57Bl/6) and LDLR KO mice.

The results are depicted in FIG. 8, which show similar to increased efficacy in LDLR (LDL receptor) deficient mice, which suggest these liposome compositions are not ApoE dependent.

Example 12: Effect of ApoE or GalNAc Lipids on Efficacy of AF12 in ApoE Deficient Mice To examine the effect of AF12 compositions on ApoE deficient mice, various concentrations of AF12 was administered in the presence of either ApoE or with a GalNAc targeting lipid as detailed below.

Experimental Plan
Animals ApoE KO mice
Total 45

| Group | Group size | Target | siRNA | Conc. (mg/mL) | Inj Vol. (uL/g) | Dose (mg/kg) | Vehicle |
|---|---|---|---|---|---|---|---|
| 1 | 3 |  |  |  | 10 |  | PBS |
| 2 | 3 | FVII | 1661 | 0.02 | 10 | 0.200 | AF12 |
| 3 | 3 | FVII | 1661 | 0.006 | 10 | 0.060 |  |
| 4 | 3 | FVII | 1661 | 0.002 | 10 | 0.020 |  |
| 5 | 3 | FVII | 1661 | 0.0006 | 10 | 0.006 |  |
| 6 | 3 | FVII | 1661 | 0.020 | 10 | 0.200 | AF12 w/ApoE |
| 7 | 3 | FVII | 1661 | 0.006 | 10 | 0.060 |  |
| 8 | 3 | FVII | 1661 | 0.002 | 10 | 0.020 |  |
| 9 | 3 | FVII | 1661 | 0.0006 | 10 | 0.006 |  |
| 10 | 3 | FVII | 1661 | 0.020 | 10 | 0.200 | AF12 w/0.5% GalNAc |
| 11 | 3 | FVII | 1661 | 0.006 | 10 | 0.060 |  |
| 12 | 3 | FVII | 1661 | 0.002 | 10 | 0.020 |  |
| 13 | 3 | FVII | 1661 | 0.0006 | 10 | 0.006 |  |

Experimental Plan
Animals ApoE KO mice
Total 45

| Group | Group size | Target | siRNA | Conc. (mg/mL) | Inj Vol. (uL/g) | Dose (mg/kg) | Vehicle |
|---|---|---|---|---|---|---|---|
| 14 | 3 | FVII | 1661 | 0.0300 | 10 | 0.300 | 5% PEDDSG w 0.5% GalNAc |
| 15 | 3 | FVII | 1661 | 0.0100 | 10 | 0.100 | 5% PEDDSG w 0.5% GalNAc |

Figure 9A:
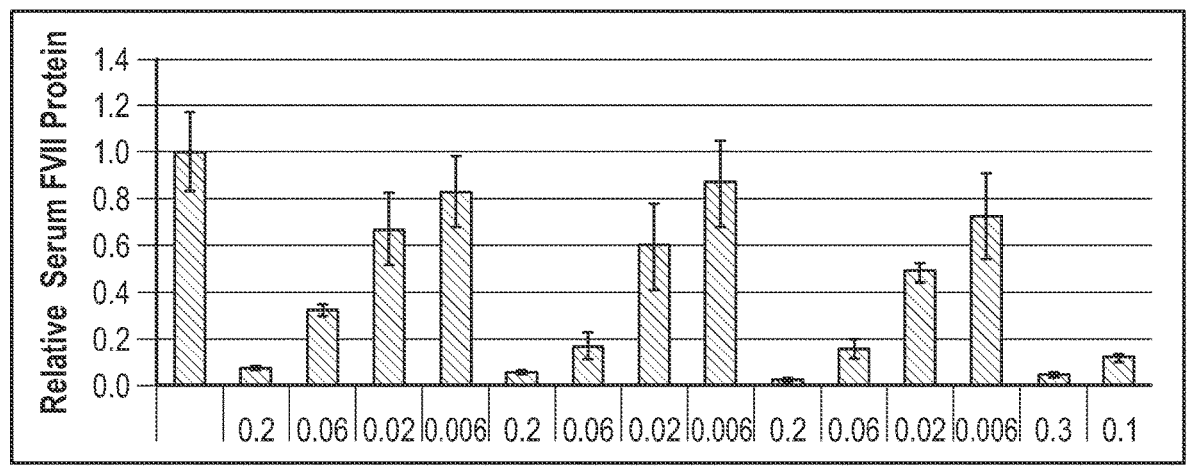
FIG. 9a is a graph illustrating the relative FVII protein level with different amounts of AF12 in ApoE and GalNAc3 containing compositions in ApoE KO mice.
Figure 9B:
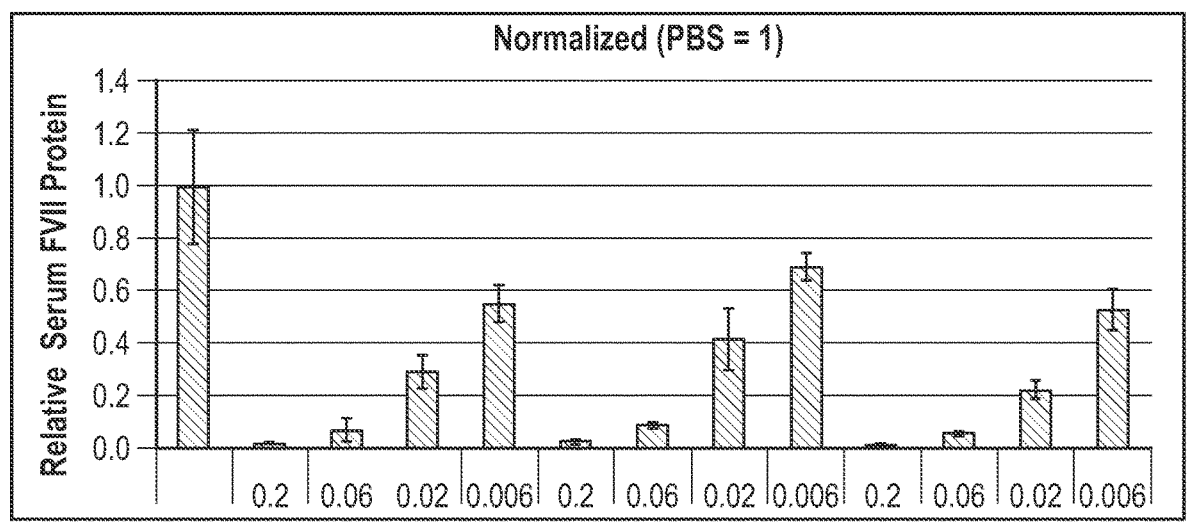
FIG. 9b is a normalized graph illustrating the relative FVII protein level with different amounts of AF12 in ApoE and GalNAc3 containing compositions in wild type mice.

As shown in FIGS. 9a and 9b, little to no difference was observed in the efficacy of the liposome compositions in the ApoE knock out and wild type mice. This was observed both with the ApoE containing liposome compositions as well as the GalNAc3 containing compositions. FIG. 9a depicts the dose response in the ApoE knock out mice whereas FIG. 9b depicts the dose response in wild type mice.

Example 13: Tie2 Silencing with a Formulation Containing Lipid T

To test delivery of nucleic acids using the formulations described herein, an endothelial specific marker, TEK tyrosine kinase was chosen. siRNA duplex AD-27430 targeting Tie2 or luciferase ("Luc") having the following sequence were formulated with AF-012 or AF-011:

| duplexName | target | strand | oligoName | oligoSeq |
|---|---|---|---|---|
| AD-27430.1 | TEK | sense | A-62836.1 | GAAGAuGcAGuGAuuuAcAdTsdT |
|  | TEK | antis | A-62837.1 | UGuAAAUcACUGcAUCUUCdTsdT |

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine |
| C | Cytidine |
| G | Guanosine |
| T | Thymidine |
| U | Uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

Mice were administered the formulations according to a "high dose" or a "low dose" protocol as described below.

In the high dose protocol, mice were administered two doses of PBS, lipid formulated siRNAs targeting Tie2, or lipid formulated siRNAs targeting luciferase (n=5 per group) as described in the table.

Pretreatment/High Dose (Two Injections)

| Lipid Formulation | Day 1 | Day 2 | Day 4 |
|---|---|---|---|
| AF-012: Lipid T/DSPC/Chol/PEG-DMG 50/10/38.5/1.5 | 0.6 mg/kg | 2.0 mg/kg | Sac'd |
| AF-011: Lipid M/DSPC/Chol/PEG-DMG 50/10/38.5/1.5 | 1.0 mg/kg | 2.0 mg/kg | Sac'd |

In the "low dose" experiment, mice were administered a single dose of lipid formulated siRNAs targeting Tie2 (N=4) or lipid formulated siRNAs targeting luciferase (n=1 for AF-012 only) as described in the table below.

Low Dose (Single Injection)

| Lipid Formulation | Day 1 | Day 2 | Day 4 |
|---|---|---|---|
| AF-012: Lipid T/DSPC/Chol/PEG-DMG 50/10/38.5/1.5 |  | 0.6 mg/kg | Sac'd |
| AF-011: Lipid M/DSPC/Chol/PEG-DMG 50/10/38.5/1.5 | 0.6 mg/kg |  | Sac'd |

As shown in the below tables, siRNAs formulated with AF-012 caused effective silencing in endothelium in different vascular beds, including the liver, lung, heart, and kidney. No silencing was observed with AF-011 formulations, which did not contain Lipid T.

Results from High Dose Experiments.

mRNA Level of Tie2 Normalized to GAPDH, VE-Cadherin, or VEGFR-2

| HIGH DOSE (0.6 + 2.0 mg/kg) | Tie2/GAPDH | Tie2/VE-Cadherin | Tie2/VEGFR-2 | Average |
|---|---|---|---|---|
| Liver | 71% (78%) | 78% (85%) | 88% (82%) | 78% |
| Lung | ND | 50% | 42% | 46% |
| Skeletal Muscle* | (58%) | ND | ND | (58%) |
| Heart | 76% | 69% | 74% | 73% |
| Kidney | 40% | (65%) | ND | 52% |
| Hipothalamus | 0% |  |  |  |

Results from Low Dose Experiments.

| LOW DOSE (0.6 mg/kg) | Tie2/GAPDH | Tie2/VE-Cadherin | Tie2/VEGFR-2 | Average |
|---|---|---|---|---|
| Liver | 64% (78%) | 59% (65%) | 82% (84%) | 68% |
| Lung | ND | 0% | 0% | 0% |

The results are summarized in FIGS. 10A-15. FIGS. 10A to 10C show the knockdown (KD) of Tie2 expression in the heart, as compared to GAPDH (FIG. 10A), VEFG Receptor 2 (VEGFR2) (FIG. 10B), and Ve-Cadherin (FIG. 10C) expression. The Tie2 siRNA only silenced Tie2 when the siRNA was packaged with the AF-012 formulation, and not when the siRNA was packaged with the AF-011 formulation.

FIGS. 11A, 11B and 12A show the knockdown (KD) of Tie2 expression in the liver by siRNA formulated with AF-012 (FIGS. 11A and 12A), but not AF-011 (FIG. 11B). The high doses are represented as 2.0 (these treatments received 0.6 and 2.0 mg/kg); the low doses are represented as 0.6 (received 0.6 mg/kg)

An increase in VEGFR2 expression in the liver was also observed in response to administration of the Tie2 siRNA (FIG. 12B).

Figure 14A:
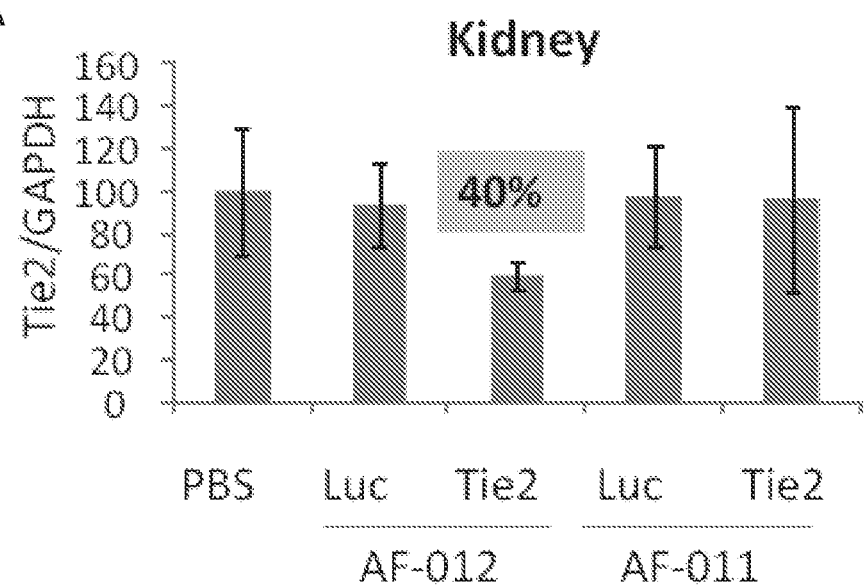
FIGS. 14A and 14B are graphs illustrating the KD of Tie2 expression in the kidney (FIG. 14A) and the skeletal muscle (FIG. 14B) when the siRNAs were formulated with AF-012, but not when formulated with AF-011.
Figure 14B:
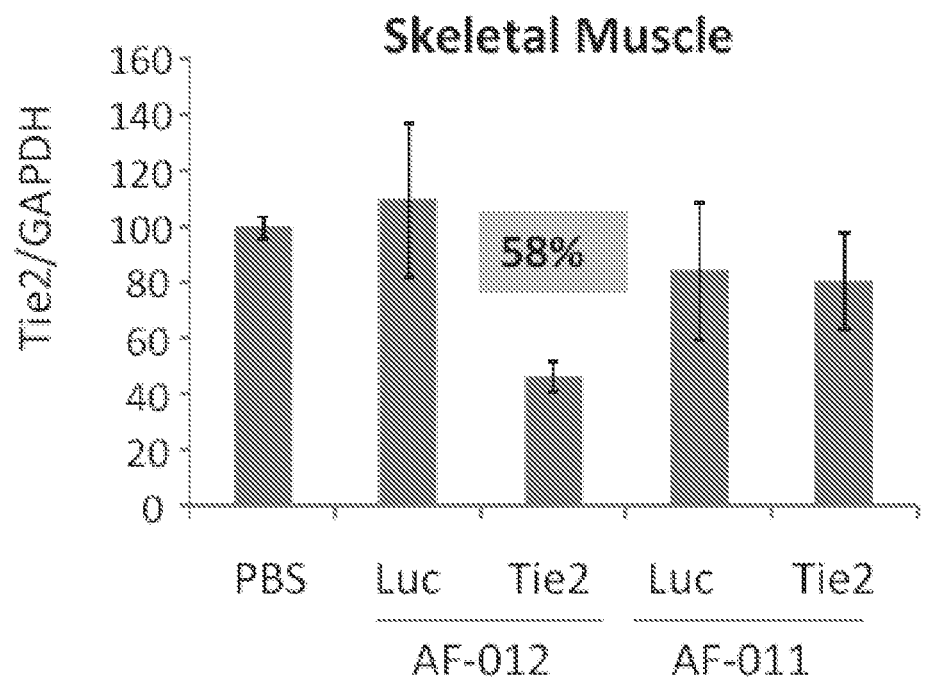

FIGS. 13A and 13B show KD of Tie2 expression in the lung by siRNA formulated with AF-012. Tie2 expression was compared with VE-Cadherin (FIG. 13A) and VEGFR-2 (FIG. 13B) expression. FIGS. 14A and 14B knocked down Tie2 expression in the kidney and skeletal muscle, respectively, when the siRNAs were formulated with AF-012, but not when formulated with AF-011.

Figure 15:
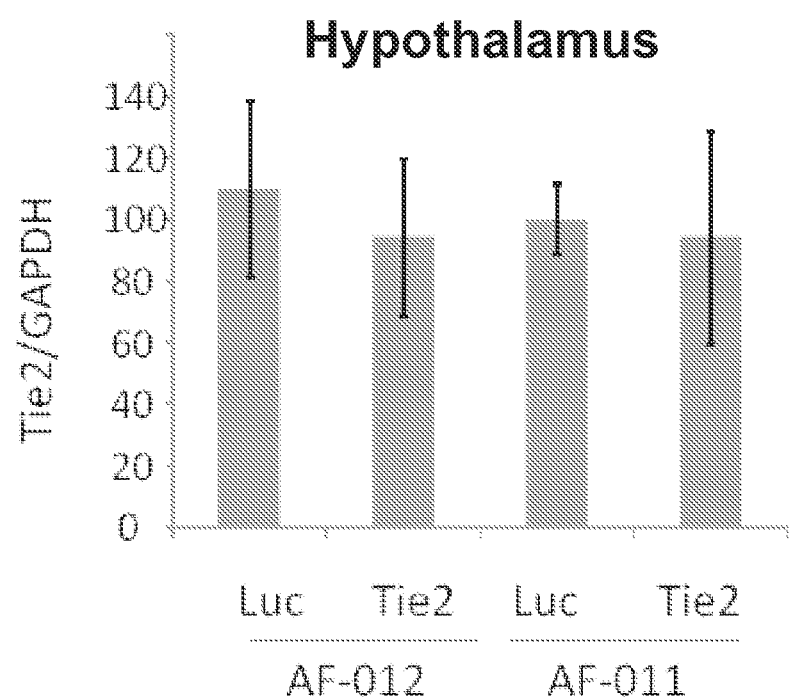
FIG. 15 is a graph showing that Tie2 siRNA did not KD gene expression in the hypothalamus when the siRNA was formulated with AF-012 or with AF-011.

FIG. 15 is a graph showing that Tie2 siRNA did not KD gene expression in the hypothalamus when the siRNA was formulated with AF-012 or with AF-011.

These results indicated that the lipid T-containing liposomes are particulary well-suited for siRNAs that are to be targeted for gene silencing in endothelial tissues.

Figure 16A:
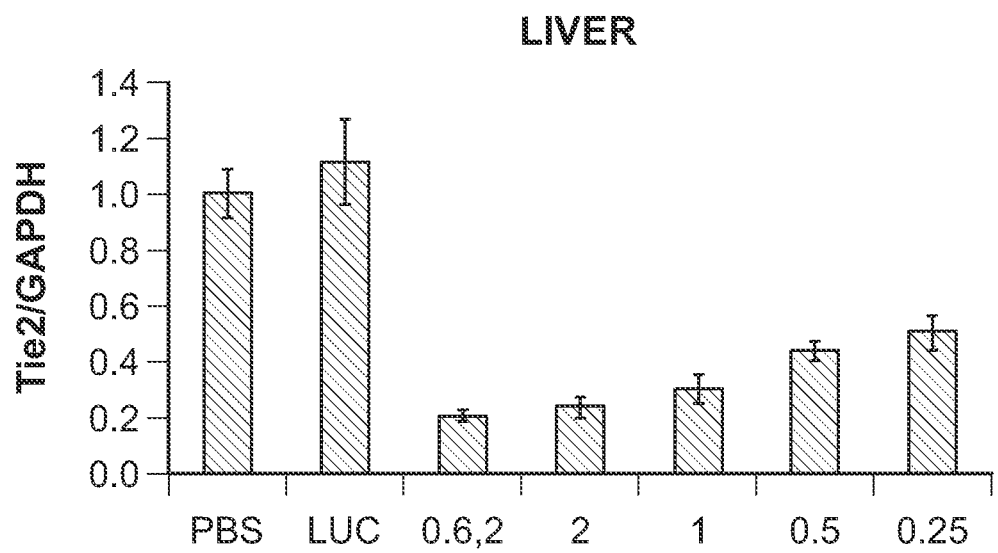
FIGS. 16A-B show the dose dependent knockdown of Tie2 expression in the liver and skeletal muscle, respectively.
Figure 16B:
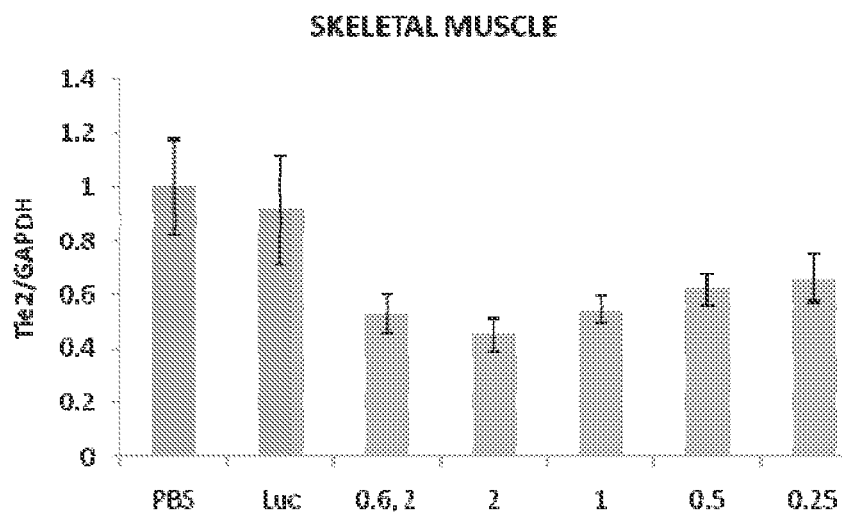
Figure 17A:
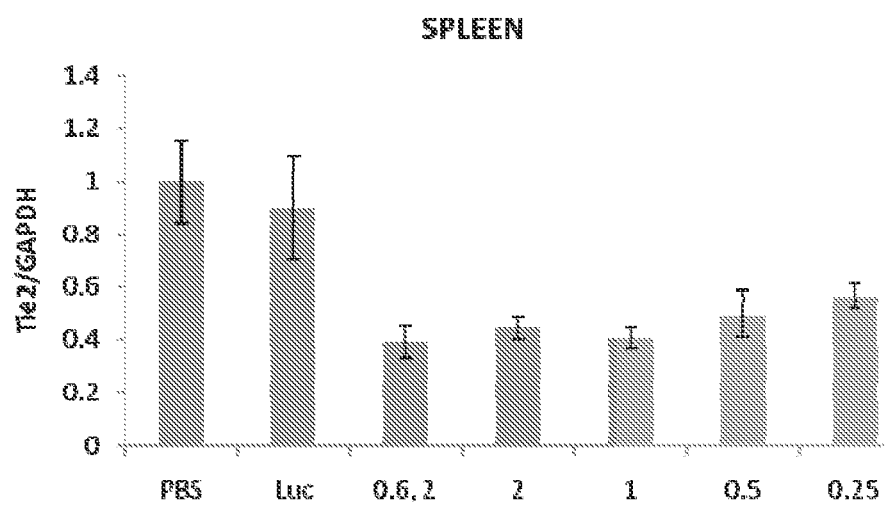
FIGS. 17A-B show the dose dependent Tie2 knockdown in the spleen and heart, respectively.
Figure 17B:
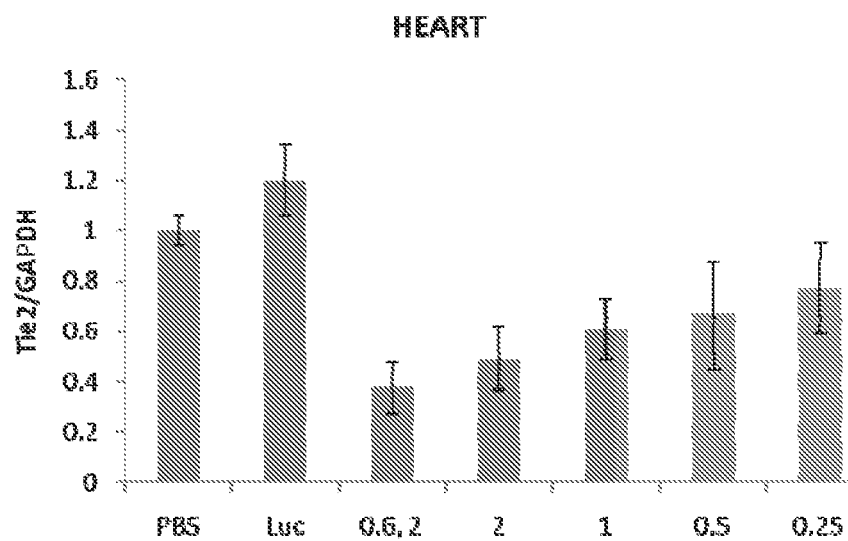
Figure 18A:
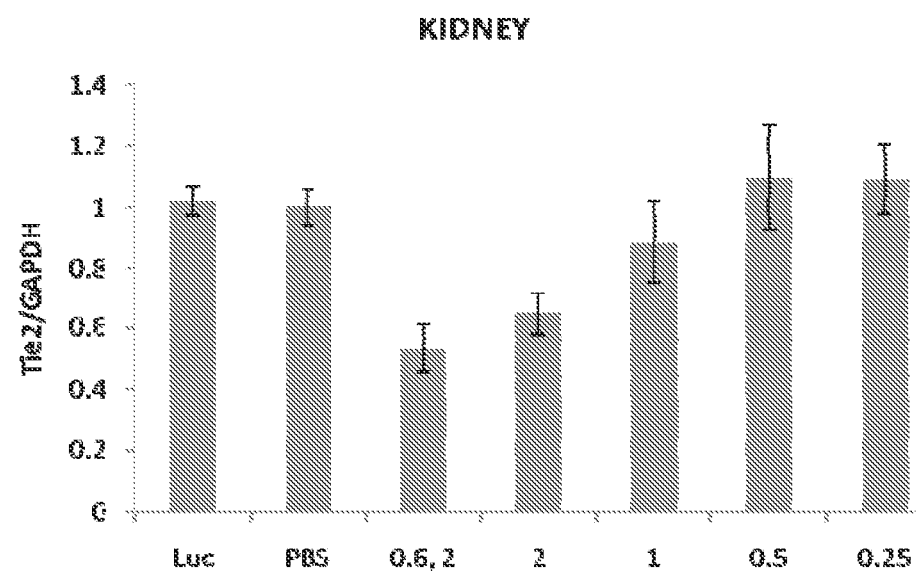
FIGS. 18A-B show Kidney and Fat tissue knockdown of Tie2 at different doses, respectively.
Figure 18B:
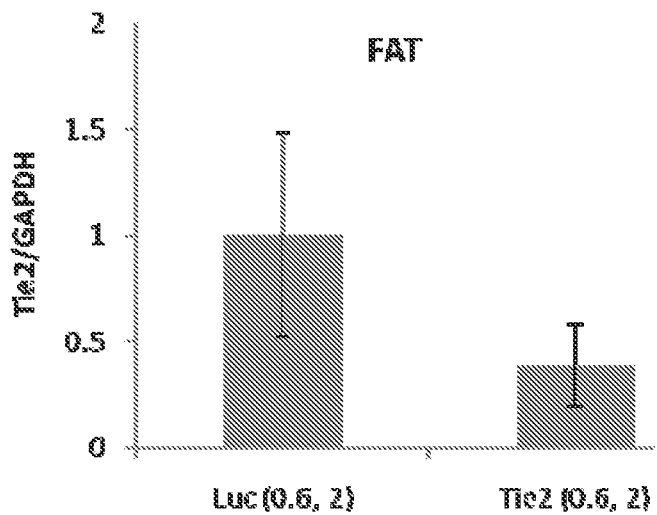

A sepate dose-response experiment was conducted. In brief, 7 groups of C57B16 females (at 5 mice per group) were administered with 0.25 mg/kg, 0.5 mg/kg, 1.0 mg/kg, 2.0 mg/kg, and 0.6 mg/kg (at Day−1)+2.0 mg/kg (at Day 0). Tissues and organs were harvested 72 hrs later and Tie2 levels were measured in these tissues. FIGS. 16A-B show the dose dependent knockdown of Tie2 expression in the liver and skeletal muscle, respectively. FIGS. 17A-B show Tie2 knockdown in the spleen and heart, respectively. FIGS. 18A-B show Kidney and Fat tissue knockdown of Tie2 at different doses, respectively.

Example 14: Lipid Composition Incorporating Multiple Different siRNAs

As a result of the relatively wide therapeutic window afforded by the formulations described herein, the possibility of silencing multiple genes in the liver with a single i.v. administration was tested. It could be envisioned that the ability to regulate multiple genes may provide a powerful therapeutic approach to diseases in which multiple gene targets have already been identified. To investigate the feasibility of this approach, siRNA sequences against liver targets of possible therapeutic interest, Factor VII, ApoB, PCSK9, Xbp1, SORT1, TTR1, TTC39B, ITGbl, ApoC3, and Rab5c were pooled and formulated with particles comprising the TechG1 lipid.

In multiple the gene silencing study Factor VII, ApoB, PCSK9, Xbp1, SORT1, TTR1, TTC39B, ITGbl, ApoC3, and Rab5c mRNA levels were assessed in livers harvested from mice dosed with a formulation containing a pool of 10 siRNAs or control unrelated siRNA targeting luciferase in a formulation comprising the TechG1 lipid. The lipid particle (AF12) comprised the following components (in molar %): TechG1:DSPC:Chol:PEG-DMG (50 mol %:10 mol %:38.5 mol %:1.5 mol %): formulated at a lipid: siRNA ratio of approximately 11.

Figure 5:
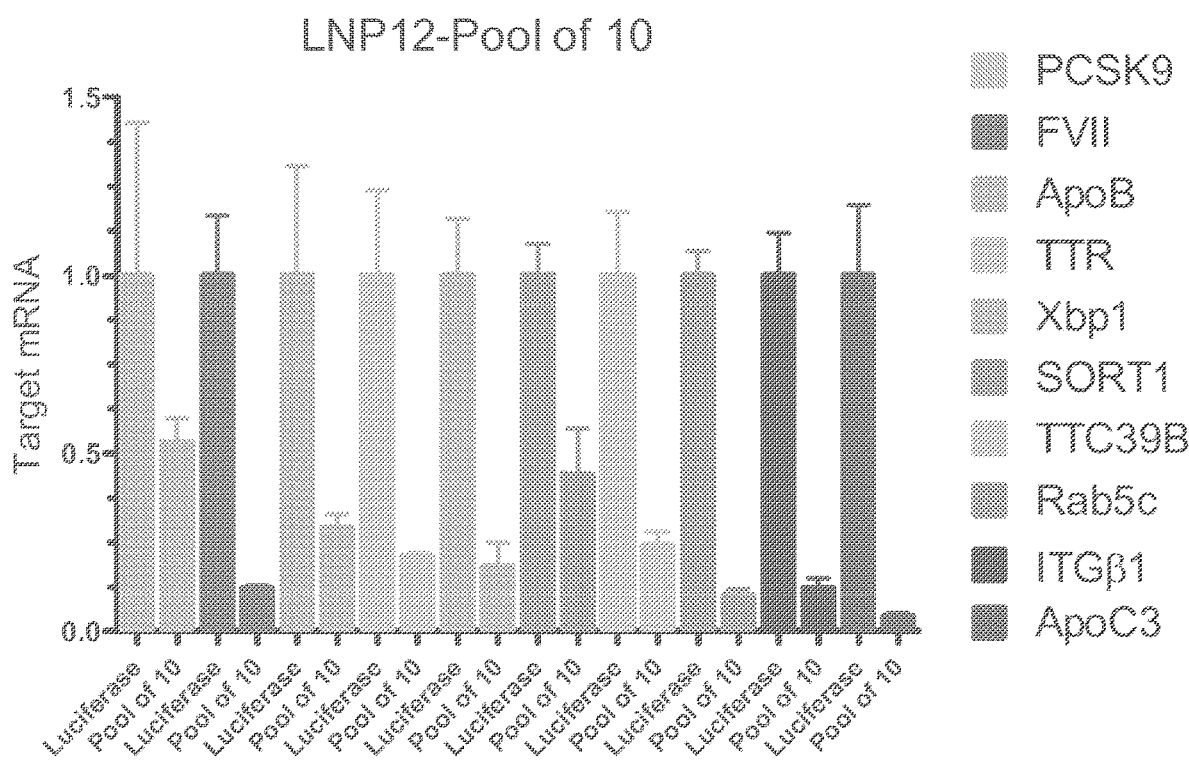
FIG. 5 is a graph showing the effect of a lipid composition comprising 10 different siRNAs on 10 different hepatic mRNAs.

48 hrs after a single tail vein injection of mice at a dose 0.1 mg/kg for each siRNA, expression of these target genes was analyzed at the mRNA level. Briefly, frozen liver tissue was ground and tissue lysates were prepared. mRNA levels of these genes normalized to those of GAPDH were determined in the lysates by using a branched DNA assay (QuantiGene Reagent System, Panomics). Target/GAPDH levels in mice treated with the pool of 10 siRNAs as described herein were plotted after normalization to the corresponding Target/GAPDH levels in mice treated with the same formulation but containing the Luciferase control siRNA. Silencing effects were investigated by dosage of each siRNA from 0.1 mg/kg. Significant silencing of all ten genes was observed at a dose of 0.1 mg/kg per siRNA (1 mg/kg total siRNA dose) (FIG. 5).

Silencing all ten genes simultaneously, as shown herein, demonstrates for the first time that multiple genes involved in similar or divergent signaling pathways could be modulated with a single administration of a single drug product. For example, simultaneous silencing of several different targets in the liver may allow for novel strategies to treat multi-factoral diseases such as metabolic syndrome, cancer, or infectious disease where multiple genes and pathways have been implicated. To our knowledge, this is the first report of the simultaneous siRNA-mediated silencing of ten hepatic targets in vivo. Given the potency of delivery using the lipids described herein, it is hypothesized that even more genes could be simultaneously silenced by a pooled siRNA product. From a therapeutic standpoint, this could enable more complex therapeutic approaches, where multiple targets achieve an enhanced therapeutic effect. For example, this strategy may be particularly useful in treating viral infections such as Hepatitis C in which rapidly evolving viral genomes have proven elusive to single siRNAs targeting a single site of the viral genome. This multi-target approach could also prove useful in regulation of low density lipoprotein levels and treatment of diseases such as cancer, in which multiple genes have already been implicated.

As such, disclosed herein are lipid compositions which comprise more than one nucleic acid composition (e.g., siRNA). In some embodiments, the lipid compositions comprises two or more different nucleic acid compositions. In some embodiments, the lipid composition comprises five or more different nucleic acid compositions. In some embodiments, the lipid composition comprises ten or more differents nucleic acid compositions. In some embodiment, the lipid composition comprises twenty or more different nucleic acid compositions. The different nucleic acid compositions can target the same target gene. In another embodiment, the different nucleic acid compositions can target distinct target genes. The target genes may be components of a same biological pathway (e.g., immune response such as an antiviral response, apoptosis, cholesterol metabolism), or may be components of distinct biological pathways. The target genes can include a gene that is not from the subject (e.g., a viral gene). In one embodiment, the lipid composition comprises at least one cationic lipid described herein. The lipid composition can further comprise a PEG- or PEG-modified lipid. In another embodiment, the lipid composition further comprises a sterol (e.g., cholesterol). In still another embodiment, the lipid composition further comprises a neutral lipid.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description is by way of example only.

What is claimed is:

1. A lipid of formula (I):

formula (I)

or a salt thereof, wherein, $X^a$ and $X^b$, for each occurrence, is independently $C_{1-6}$ alkylene;

n is 0, 1, 2, 3, 4, or 5;

A, for each occurrence, is $NR_2$ or a cyclic moiety optionally substituted with 1-3 R;

B is NR or a cyclic moiety optionally substituted with 1-2 R;
each R is independently H, alkyl,

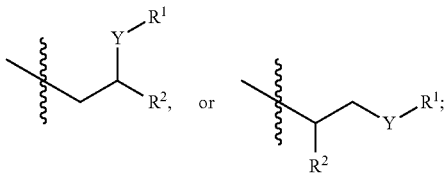

provided that at least one R is

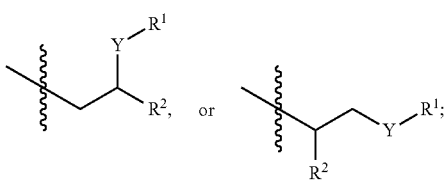

$R^1$, for each occurrence, is independently H, $R^3$,

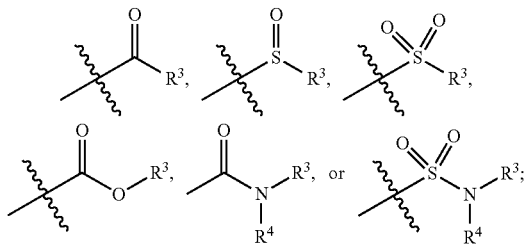

$R^2$, for each occurrence, is independently, alkyl, alkenyl, alkynyl, heteroalkyl, heteroalkenyl, or heteroalkynyl;
$R^3$, for each occurrence, is independently, alkyl, alkenyl, alkynyl, heteroalkyl, heteroalkenyl, or heteroalkynyl;
Y, for each occurrence, is O;
$R^4$, for each occurrence is independently H alkyl, alkenyl, alkynyl, heteroalkyl, heteroalkenyl, or heteroalkynyl.

2. The lipid of claim 1, wherein n is 1 or 2.
3. The lipid of claim 1, wherein A for each occurrence is $NR_2$.
4. The lipid of claim 1, wherein B is a cyclic moiety.
5. The lipid of claim 1, wherein B is a nitrogen containing cyclic moiety.
6. The lipid of claim 1, wherein B is piperidinyl or piperizinyl moiety.

7. The lipid of claim 1, wherein each R is independently

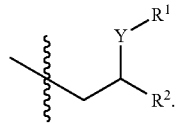

8. The lipid of claim 1, wherein $R^1$, for each occurrence, is H.
9. The lipid of claim 1, wherein $R^2$, for each occurrence, is independently alkyl.
10. The lipid of claim 1, wherein $R^2$, for each occurrence, is independently, alkenyl.
11. The lipid of claim 1, wherein n is 1 or 2; A is $NR_2$; B is NR or a cyclic moiety; $R^1$ is H; $R^2$ is independently alkyl or alkenyl; Y is O; and R is

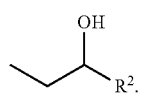

12. The lipid of claim 1, wherein n is 1; A is $NR_2$; B is a cyclic moiety; $R^1$ is H; $R^2$ is independently alkyl or alkenyl; Y is O; and R is

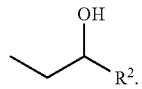

13. A composition, the composition comprising a sterol, a neutral lipid, a PEG or a PEG-modified lipid, and a lipid as described in claim 1.
14. The composition of claim 13, wherein the sterol is cholesterol.
15. The composition of claim 13, wherein the PEG or PEG-modified lipid is a PEG-modified lipid.
16. The composition of claim 13, wherein the composition is a liposome.
17. The composition of claim 13, further comprising therapeutic agent.
18. The composition of claim 17, wherein the therapeutic agent is a nucleic acid agent.
19. The composition of claim 17, wherein the therapeutic agent is siRNA.
20. The composition of claim 17, wherein the therapeutic agent is mRNA.

* * * * *